(12) United States Patent
Bilodeau et al.

(10) Patent No.: US 6,586,423 B2
(45) Date of Patent: *Jul. 1, 2003

(54) TYROSINE KINASE INHIBITORS

(75) Inventors: Mark T. Bilodeau, Lansdale, PA (US); George D. Hartman, Lansdale, PA (US); Peter J. Manley, Harleysville, PA (US); Randall W. Hungate, Newbury Park, CA (US); Leonard Rodman, New York, NY (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/061,817

(22) Filed: Feb. 1, 2002

(65) Prior Publication Data

US 2003/0064996 A1 Apr. 3, 2003

Related U.S. Application Data

(63) Continuation of application No. 09/658,680, filed on Sep. 8, 2000.
(60) Provisional application No. 60/153,348, filed on Sep. 10, 1999.

(51) Int. Cl.$^7$ .................. C07D 413/12; C07D 417/12; A61K 31/4178; A61K 31/4196; A61K 31/422

(52) U.S. Cl. ................ 514/217.04; 546/270.7; 546/193; 546/148; 546/256; 514/342; 514/318; 514/253.1; 514/307; 514/333; 514/236.8; 514/218; 514/227.5; 514/274; 544/364; 544/124; 544/58.2; 544/316; 540/597; 540/492

(58) Field of Search ............... 546/270.7, 193, 546/148, 256; 514/342, 318, 253.1, 307, 333, 236.8, 217.04, 218, 227.5, 274; 544/364, 124, 58.2, 316; 540/597, 492

(56) References Cited

U.S. PATENT DOCUMENTS

| | | | |
|---|---|---|---|
| 4,788,195 | A | 11/1988 | Torley et al. |
| 4,876,252 | A | 10/1989 | Torley et al. |
| 5,463,071 | A | 10/1995 | Himmelsbach et al. |
| 5,516,775 | A | 5/1996 | Zimmermann et al. |
| 5,521,184 | A | 5/1996 | Zimmermann |
| 5,863,924 | A | 1/1999 | Berger et al. |
| 5,952,331 | A | 9/1999 | Berger et al. |
| 5,958,934 | A | 9/1999 | Berger et al. |

FOREIGN PATENT DOCUMENTS

| | | |
|---|---|---|
| DE | 19824175 A1 | 5/1998 |
| EP | 0 564 409 A1 | 10/1993 |
| JP | 01075475 A | 3/1989 |
| JP | 07149745 A | 6/1995 |
| WO | WO 94/01423 | 1/1994 |
| WO | WO 95/09847 | 4/1995 |
| WO | WO 95/09852 | 4/1995 |
| WO | WO 93/35276 | 12/1995 |
| WO | WO 95/35275 | 12/1995 |
| WO | WO 97/19065 | 5/1997 |
| WO | WO97/44326 | 11/1997 |
| WO | WO 99/64418 | 12/1999 |
| WO | WO 99/65884 | 12/1999 |
| WO | WO 00/09495 | 2/2000 |
| WO | WO 00/12497 | 3/2000 |
| WO | WO 00/62778 | 10/2000 |

OTHER PUBLICATIONS

Mitchell et al., Inhibitors of Angiogenesis, Annual Reports in Medicinal Chemistry 27: 139–148 1992.*
Oncogene, vol. 5, pp. 519–524 (1990), by M. Shibuya, et al.
FEBS Letters, vol. 473, pp. 161–164 (2000), by M. Nakagawa, et al.
Stem Cells, vol. 12, pp. 1–6 (1994), by T. R. Burke, Jr.
Molecular Cell, vol. 4, pp. 915–924 (1999), by B. Eliceiri, et al.
Oncogene, vol. 6, pp. 1677–1683 (1991), by B. Terman, et al.
Nature Medicine, vol. 5, No. 6, pp. 623–628 (1999), by H. Gerber, et al.
Nature Biotech., vol. 17, pp. 963–968 (1999), by H. Brower.
J. of Clin. Investigation, vol. 104, No. 11, pp. 1613–1620 (1999), by N. van Bruggen, et al.
Drug News Perspect, vol. 11, No. 5, pp. 265–270 (1998), by D. A. Greenberg.
Nature, vol. 407, pp. 242–248 (2000), by G. Yancopoulos, et al.
Nature, vol. 407, pp. 249–257 (2000), by P. Carmeliet, et al.
Platelets, vol. 10, pp. 285–292 (1999), by A. Amirkhosravi, et al.
Endocrinology, Abstract, vol. 141, No. 5, pp. 1667–1674 (2000), by M. Deckers, et al.

* cited by examiner

Primary Examiner—Richard L. Raymond
Assistant Examiner—Hong Liu
(74) Attorney, Agent, or Firm—Dianne Brown; J. Antonio Garcia-Rivas; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

8 Claims, No Drawings

TYROSINE KINASE INHIBITORS

RELATED APPLICATIONS

This is a continuation, of application Ser. No. 09/658,680 filed Sep. 8, 2000.

This application claims priority under 35 U.S.C. §119(e) from U.S. Provisional Application No. 60/153,348, filed Sep. 10, 1999.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN & P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene,* 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

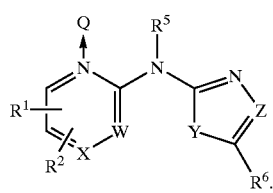

I

DETAILED DESCRIPTION OF THE INVENTION

The compounds of this invention are useful in the inhibition of kinases and are illustrated by a compound of Formula I:

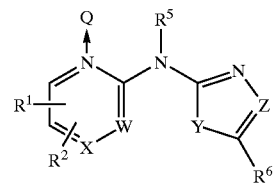

I or a pharmaceutically acceptable salt or stereoisomer thereof, wherein
  X—W is: C—C, N—C, or C—N;
  Y is: O, S or N—$R^4$;
  Z is: N or C—$R^4$;
  Q is: O or absent;
  $R^1$ and $R^2$ are independently selected from:
    1) H,
    2) $O_r(C_1$–$C_6)$perfluoroalkyl,
    3) OH,
    4) CN,
    5) halogen,
    6) $(C=O)_rO_s(C_1$–$C_{10})$alkyl,
    7) $(C=O)_rO_s(C_2$–$C_8)$cycloalkyl,
    8) $(C=O)_rO_s(C_2$–$C_{10})$alkenyl,
    9) $(C=O)_rO_s(C_2$–$C_{10})$alkynyl,
    10) $(C=O)_rO_s$aryl,
    11) $(C=O)_rO_s$heterocyclyl, or
    12) $NR^aR^b$,
      wherein r and s are independently 0 or 1, and said alkyl, cycloalkyl, alkenyl, alkynyl, aryl, and heterocyclyl is optionally substituted with one or more substituents selected from $R^7$;
  $R^4$ is H, aryl or $(C_1$–$C_6)$alkyl;
  $R^5$ is:
    1) H,
    2) $SO_2R^c$,
    3) $(C=O)_rR^c$, wherein r is 0 or 1, or
    4) $CO_2R^c$;
  $R^6$ is:
    1) aryl,
    2) CN,
    3) $(C=O)NR^aR^b$,
    4) $(C_3$–$C_8)$cycloalkyl
    5) $(C_1$–$C_{10})$alkyl,
    6) $(C_2$–$C_8)$alkenyl,
    7) $(C_2$–$C_8)$alkynyl, and
    8) heterocyclyl,
      wherein r and s are independently 0 or 1, and said aryl, cycloalkyl, alkyl, alkenyl, alkynyl and heterocyclyl optionally substituted with one or more substituents selected from $R^7$;
  $R^7$ is:
    1) $O_r(C=O)_sNR^aR^b$,
    2) $(C=O)_rO_s$aryl,
    3) $(C=O)_rO_s$-heterocyclyl,
    4) halogen,
    5) OH,
    6) oxo,
    7) $O(C_1$–$C_3)$perfluoroalkyl,
    8) $(C_1$–$C_3)$perfluoroalkyl,
    9) $(C=O)_rO_s(C_1$–$C_{10})$alkyl,
    10) CHO,
    11) $CO_2H$,
    12) CN, or
    13) $(C_3$–$C_8)$cycloalkyl, wherein r and s are independently 0 or 1, and said aryl, heterocyclyl and cycloalkyl are optionally substituted with one or more substituents selected from $R^d$;

$R^a$ and $R^b$ are independently:
1) H,
2) $(C{=}O)_r(C_1{-}C_{10})$alkyl,
3) $(C{=}O)_r(C_3{-}C_6)$cycloalkyl,
4) $S(O)_2R^c$,
5) $(C{=}O)_r$heterocyclyl,
6) $(C{=}O)_r$aryl, or
7) $CO_2R^c$, wherein r is 0 or 1 and said alkyl, cycloalkyl, heterocyclyl, and aryl optionally substituted with one or more substituents selected from $R^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^d$;

$R^c$ is $(C_1{-}C_6)$alkyl, $(C_3{-}C_6)$cycloalkyl, aryl, or heterocyclyl; and $R^d$ is selected from:
1) $(C{=}O)_rO_s(C_1{-}C_{10})$alkyl, wherein r and s are independently 0 or 1, optionally substituted with up to three substituents selected from OH, $(C_1{-}C_6)$alkoxy, halogen, CN, oxo, $N(R^e)_2$ and $S(O)_2R^c$,
2) $O_r(C_1{-}C_3)$perfluoroalkyl,
3) $(C_0{-}C_6)$alkylene-$S(O)_mR^c$, wherein m is 0, 1, or 2,
4) oxo,
5) OH,
6) halo,
7) CN,
8) $(C_3{-}C_6)$cycloalkyl, optionally substituted with up to three substituents selected from OH, $(C_1{-}C_6)$alkoxy, halogen, CN, oxo, $N(R^e)_2$ and $S(O)_2R^c$,
9) $(C_0{-}C_6)$alkylene-aryl, optionally substituted with up to three substituents selected from $R^e$,
10) $(C_0{-}C_6)$alkylene-heterocyclyl, optionally substituted with up to three substituents selected from $R^e$,
11) $(C_0{-}C_6)$alkylene-$N(R^e)_2$,
12) $C(O)R^c$,
13) $CO_2R^c$,
14) $C(O)H$, and
15) $CO_2H$; and $R^e$ is H, $(C_1{-}C_6)$alkyl, aryl, heterocyclyl, $(C_3{-}C_6)$cycloalkyl or $S(O)_2R^c$.

Another embodiment of the present invention is a compound of Formula I, as described above, or a pharmaceutically acceptable salt or stereoisomer thereof, wherein X—W is: C—C, N—C, or C—N;
Y is: O, S or N—$R^4$;
Z is: N or C—$R^4$;
Q is: O or absent;
$R^1$ is:
1) $O_r(C_1{-}C_6)$perfluoroalkyl,
2) OH,
3) CN,
4) halogen,
5) $(C{=}O)_rO_s(C_1{-}C_{10})$alkyl,
6) $(C{=}O)_rO_s(C_2{-}C_8)$cycloalkyl,
7) $(C{=}O)_rO_s(C_2{-}C_{10})$alkenyl,
8) $(C{=}O)_rO_s(C_2{-}C_{10})$alkynyl,
9) $(C{=}O)_rO_s$aryl,
10) $(C{=}O)_rO_s$heterocyclyl, or
11) $NR^aR^b$, wherein r and s are independently 0 or 1, and said alkyl, cycloalkyl, alkenyl, alkynyl, aryl, and heterocyclyl is optionally substituted with one or more substituents selected from $R^7$;

$R^2$ is $R^1$ or H;
$R^4$ is H, aryl or $(C_1{-}C_6)$alkyl;
$R^5$ is:
1) H,
2) $SO_2R^c$,
3) $(C{=}O)_rR^c$, wherein r is 0 or 1, or
4) $CO_2R^c$;

$R^6$ is CN or $(C{=}O)NR^aR^b$;
$R^7$ is:
1) $O_r(C{=}O)_sNR^aR^b$,
2) $(C{=}O)_rO_s$aryl,
3) $(C{=}O)_rO_s$-heterocyclyl,
4) halogen,
5) OH,
6) oxo,
7) $O(C_1{-}C_3)$perfluoroalkyl,
8) $(C_1{-}C_3)$perfluoroalkyl,
9) $(C{=}O)_rO_s(C_1{-}C_{10})$alkyl,
10) CHO,
11) $CO_2H$,
12) CN, or
13) $(C_3{-}C_8)$cycloalkyl, wherein r and s are independently 0 or 1, and said aryl, heterocyclyl and cycloalkyl are optionally substituted with one or more substituents selected from $R^d$;

$R^a$ and $R^b$ are independently:
1) H,
2) $(C{=}O)_r(C_1{-}C_{10})$alkyl,
3) $(C{=}O)_r(C_3{-}C_6)$cycloalkyl,
4) $S(O)_2R^c$,
5) $(C{=}O)_r$heterocyclyl,
6) $(C{=}O)_r$aryl, or
7) $CO_2R^c$, wherein r is 0 or 1 and said alkyl, cycloalkyl, heterocyclyl, and aryl optionally substituted with one or more substituents selected from $R^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^d$;

$R^c$ is $(C_1{-}C_6)$alkyl, $(C_3{-}C_6)$cycloalkyl, aryl, or heterocyclyl; and $R^d$ is selected from:
1) $(C{=}O)_rO_s(C_1{-}C_{10})$alkyl, wherein r and s are independently 0 or 1, optionally substituted with up to three substituents selected from OH, $(C_1{-}C_6)$alkoxy, halogen, CN, oxo, $N(R^e)_2$ and $S(O)_2R^c$, 2) $O_r(C_1-C_3)$perfluoroalkyl,
3) $(C_0-C_6)$alkylene-$S(O)_m R^c$, wherein m is 0, 1, or 2,
4) oxo,
5) OH,
6) halo,
7) CN,
8) $(C_3-C_6)$cycloalkyl, optionally substituted with up to three substituents selected from OH, $(C_1-C_6)$alkoxy, halogen, CN, oxo, $N(R^e)_2$ and $S(O)_2 R^c$,
9) $(C_0-C_6)$alkylene-aryl, optionally substituted with up to three substituents selected from $R^e$,
10) $(C_0-C_6)$alkylene-heterocyclyl, optionally substituted with up to three substituents selected from $R^e$,
11) $(C_0-C_6)$alkylene-$N(R^e)_2$,
12) $C(O)R^c$,
13) $CO_2 R^c$,
14) C(O)H, and
15) $CO_2$H; and $R^e$ is H, $(C_1-C_6)$alkyl, aryl, heterocyclyl, $(C_3-C_6)$cycloalkyl or $S(O)_2 R^c$.

Yet another embodiment of the invention is the compound described directly above wherein Z is C—$R^4$, Y is S, X—W is C—C, and Q is absent.

Also included within the scope of the claims is the compound above wherein $R^1$ is:
1) $O_r(C_1-C_6)$perfluoroalkyl,
2) OH,
3) CN,
4) halogen,
5) $(C=O)_r O_s(C_1-C_6)$alkyl,
6) $(C=O)_r O_s(C_2-C_6)$cycloalkyl,
7) $(C=O)_r O_s(C_2-C_6)$alkenyl,
8) $(C=O)_r O_s(C_2-C_6)$alkynyl,
9) $(C=O)_r O_s$aryl,
10) $(C=O)_r O_s$heterocyclyl, or
11) $NR^a R^b$,
wherein r and s are independently 0 or 1, and said alkyl, cycloalkyl, alkenyl, alkynyl, aryl, and heterocyclyl is optionally substituted with one, two or three substituents selected from $R^7$;

$R^2$ is $R^1$ or H;
$R^4$ is H or $(C_1-C_6)$alkyl;
$R^5$ is:
1) H,
2) $SO_2 R^c$,
3) $(C=O)_r R^c$, wherein r is 0 or 1, or
4) $CO_2 R^c$;
$R^6$ is CN;
$R^7$ is:
1) $O_r(C=O)_s NR^a R^b$,
2) $(C=O)_r O_s$aryl,
3) $(C=O)_r O_s$-heterocyclyl,
4) halogen,
5) OH,
6) oxo,
7) $O(C_1-C_3)$perfluoroalkyl,
8) $(C_1-C_3)$perfluoroalkyl,
9) $(C=O)_r O_s(C_1-C_6)$alkyl,
10) CHO,
11) $CO_2$H,
12) CN, or
13) $(C_3-C_6)$cycloalkyl, wherein r and s are independently 0 or 1, and said aryl, heterocyclyl and cycloalkyl are optionally substituted with one, two or three substituents selected from $R^d$;

$R^a$ and $R^b$ are independently:
1) H,
2) $(C=O)_r(C_1-C_6)$alkyl,
3) $(C=O)_r(C_3-C_6)$cycloalkyl,
4) $S(O)_2 R^c$,
5) $(C=O)_r$heterocyclyl,
6) $(C=O)_r$aryl, or
7) $CO_2 R^c$,
wherein r is 0 or 1 and said alkyl, cycloalkyl, heterocyclyl, and aryl optionally substituted with one, two or three substituents selected from $R^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one, two or three substituents selected from $R^d$;

$R^c$ is $(C_1-C_6)$alkyl, $(C_3-C_6)$cycloalkyl, or aryl; and
$R^d$ is selected from:
1) $(C=O)_r O_s(C_1-C_6)$alkyl, wherein r and s are independently 0 or 1, optionally substituted with up to three substituents selected from OH, $(C_1-C_6)$alkoxy, halogen, CN, oxo, $N(R^e)_2$ and $S(O)_2 R^c$,
2) $O_r(C_1-C_3)$perfluoroalkyl,
3) $(C_0-C_6)$alkylene-$S(O)_m R^c$, wherein m is 0, 1, or 2,
4) oxo,
5) OH,
6) halo,
7) CN,
8) $(C_3-C_6)$cycloalkyl, optionally substituted with up to three substituents selected from OH, $(C_1-C_6)$alkoxy, halogen, CN, oxo and $S(O)_2 R^c$,
9) $(C_0-C_6)$alkylene-aryl, optionally substituted with up to three substituents selected from $R^e$,
10) $(C_0-C_6)$alkylene-heterocyclyl, optionally substituted with up to three substituents selected from $R^e$,
11) $(C_0-C_6)$alkylene-$N(R^e)_2$,
12) $C(O)R^c$,
13) $CO_2 R^c$,
14) C(O)H, and
15) $CO_2$H; and $R^e$ is H, $(C_1-C_6)$alkyl, aryl, heterocyclyl, $(C_3-C_6)$cycloalkyl or $S(O)_2 R^c$.

A further embodiment is the compound described above wherein $R^1$ is $(C_1-C_{10})$alkylene-$NR^a R^b$, optionally substituted with one or two substituents selected from $R^7$;

$R^2$ is H, CN, halogen, $(C_1-C_6)$alkyl, or $(C_1-C_6)$alkyloxy;
$R^4$ is H or $(C_1-C_6)$alkyl;
$R^5$ is H, $(C_1-C_6)$alkyl, $CO_2(C_1-C_6)$alkyl, or $CO(C_1-C_6)$alkyl;
$R^6$ is CN;
$R^7$ is selected from:
1) $O_r(C=O)_s NR^a R^b$,
2) $(C=O)_r O_s$aryl, 3) (C=O)$_r$O$_s$-heterocyclyl,
4) halogen,
5) OH,
6) oxo,
7) O(C$_1$-C$_3$)perfluoroalkyl,
8) (C$_1$-C$_3$)perfluoroalkyl, and
9) (C=O)$_r$O$_s$(C$_1$-C$_6$)alkyl,
10) CHO,
11) CO$_2$H,
12) CN,
13) (C$_3$-C$_6$)cycloalkyl,
  wherein r and s are independently 0 or 1, and said aryl, heterocyclyl and cycloalkyl are optionally substituted with one or two substituents selected from R$^d$;
R$^a$ and R$^b$ are independently selected from:
  1) H,
  2) (C=O)$_r$(C$_1$-C$_6$)alkyl,
  3) (C=O)$_r$(C$_3$-C$_6$)cycloalkyl,
  4) S(O)$_2$R$^c$,
  5) (C=O)$_r$heterocyclyl,
  6) (C=O)$_r$aryl, and
  7) CO$_2$R$^c$,
    wherein r is 0 or 1 and said alkyl, cycloalkyl, heterocyclyl, and aryl optionally substituted with one to three substituents selected from R$^d$, or
R$^a$ and R$^b$ are taken together with the nitrogen to which they are attached to form a monocyclic or bicyclic heterocycle with 5–7 members in each ring and optionally containing, in addition to the nitrogen, one additional heteroatom selected from N, O and S, said monocyclic or bicyclic heterocycle optionally substituted with one or two substituents selected from R$^d$;
R$^c$ is (C$_1$-C$_6$)alkyl, (C$_3$-C$_6$)cycloalkyl, or aryl; and R$^d$ is selected from:
  1) (C=O)$_r$O$_s$(C$_1$-C$_6$)alkyl, wherein r and s are independently 0 or 1, optionally substituted with up to three substituents selected from OH, (C$_1$-C$_6$)alkoxy, halogen, CN, oxo, N(R$^e$)$_2$ and S(O)$_2$R$^c$,
  2) O$_r$(C$_1$-C$_3$)perfluoroalkyl,
  3) (C$_0$-C$_6$)alkylene-S(O)$_m$R$^c$, wherein m is 0, 1, or 2,
  4) oxo,
  5) OH,
  6) halo,
  7) CN,
  8) (C$_3$-C$_6$)cycloalkyl, optionally substituted with up to three substituents selected from OH, (C$_1$-C$_6$)alkoxy, halogen, CN, oxo and S(O)$_2$R$^c$,
  9) (C$_0$-C$_6$)alkylene-aryl, optionally substituted with one or two substituents selected from R$^e$,
  10) (C$_0$-C$_6$)alkylene-heterocyclyl, optionally substituted with one or two substituents selected from R$^e$,
  11) (C$_0$-C$_6$)alkylene-N(R$^e$)$_2$,
  12) C(O)R$^e$,
  13) CO$_2$R$^c$,
  14) C(O)H, and
  15) CO$_2$H; and
R$^e$ is H, (C$_1$-C$_6$)alkyl, aryl, heterocyclyl, (C$_3$-C$_6$)cycloalkyl or S(O)$_2$R$^c$.

Another embodiment of the invention is illustrated by a compound of Formula I, as recited above, or a pharmaceutically acceptable salt or stereoisomer thereof, wherein X—W is: C—C, N—C, or C—N;
Y is: O, S, or N—R$^4$;
Z is: N or C—R$^4$;
Q is: O or absent;
R$^1$ is (C$_1$-C$_{10}$)alkyl, substituted with O$_r$(C=O)$_s$NR$^a$R$^b$, wherein r and s are independently 0 or 1, and optionally substituted with one or more substituents selected from R$^7$;
R$^2$ is selected from:
  1) H,
  2) O$_r$(C$_1$-C$_6$)perfluoroalkyl,
  3) OH,
  4) CN,
  5) halogen,
  6) (C=O)$_r$O$_s$(C$_1$-C$_{10}$)alkyl,
  7) (C=O)$_r$O$_s$(C$_2$-C$_8$)cycloalkyl,
  8) (C=O)$_r$O$_s$(C$_2$-C$_{10}$)alkenyl,
  9) (C=O)$_r$O$_s$(C$_2$-C$_{10}$)alkynyl,
  10) (C=O)$_r$O$_s$aryl,
  11) (C=O)$_r$O$_s$heterocyclyl, and
  12) NR$^a$R$^b$,
    wherein r and s are independently 0 or 1, and said alkyl, cycloalkyl, alkenyl, alkynyl, aryl, and heterocyclyl is optionally substituted with one or more substituents selected from R$^7$;
R$^4$ is H, aryl or (C$_1$-C$_6$)alkyl;
R$^5$ is selected from:
  1) H,
  2) SO$_2$R$^c$,
  3) (C=O)$_r$R$^c$, wherein r is 0 or 1, and
  4) CO$_2$R$^c$;
R$^6$ is selected from:
  1) aryl,
  2) (C$_3$-C$_8$)cycloalkyl
  3) (C$_1$-C$_{10}$)alkyl,
  4) (C$_2$-C$_8$)alkenyl,
  5) (C$_2$-C$_8$)alkynyl, and
  6) heterocyclyl,
    wherein r and s are independently 0 or 1, and said aryl, cycloalkyl, alkyl, alkenyl,alkynyl and heterocyclyl optionally substituted with one or more substituents selected from R$^7$;
R$^7$ is selected from:
  1) O$_r$(C=O)$_s$NR$^a$R$^b$,
  2) (C=O)$_r$O$_s$aryl,
  3) (C=O)$_r$O$_s$-heterocyclyl,
  4) halogen,
  5) OH,
  6) oxo,
  7) O(C$_1$-C$_3$)perfluoroalkyl,
  8) (C$_1$-C$_3$)perfluoroalkyl, and
  9) (C=O)$_r$O$_s$(C$_1$-C$_{10}$)alkyl,
  10) CHO,
  11) CO$_2$H,
  12) CN,
  13) (C$_3$-C$_8$)cycloalkyl,
    wherein r and s are independently 0 or 1, and said aryl, heterocyclyl and cycloalkyl are optionally substituted with one or more substituents selected from R$^d$;
R$^a$ and R$^b$ are independently selected from:
  1) H,
  2) (C=O)$_r$(C$_1$-C$_{10}$)alkyl,
  3) (C=O)$_r$(C$_3$-C$_6$)cycloalkyl,
  4) S(O)$_2$R$^c$,
  5) (C=O)$_r$heterocyclyl, 6) (C=O)$_r$aryl, and
7) CO$_2$R$^c$,
   wherein r is 0 or 1 and said alkyl, cycloalkyl, heterocyclyl, and aryl optionally substituted with one or more substituents selected from R$^d$, or R$^a$ and R$^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from R$^d$;

R$^c$ is (C$_1$–C$_6$)alkyl, (C$_3$–C$_6$)cycloalkyl, aryl, or heterocyclyl; and R$^d$ is selected from:
1) (C=O)$_r$O$_s$(C$_1$–C$_{10}$)alkyl, wherein r and s are independently 0 or 1, optionally substituted with up to three substituents selected from OH, (C$_1$–C$_6$)alkoxy, halogen, CN, oxo, N(R$^e$)$_2$ and S(O)$_2$R$^c$,
2) O$_r$(C$_1$–C$_3$)perfluoroalkyl,
3) (C$_0$–C$_6$)alkylene-S(O)$_m$R$^c$, wherein m is 0, 1, or 2,
4) oxo,
5) OH,
6) halo,
7) CN,
8) (C$_3$–C$_6$)cycloalkyl, optionally substituted with up to three substituents selected from OH, (C$_1$–C$_6$)alkoxy, halogen, CN, oxo, N(R$^e$)$_2$, and S(O)$_2$R$^c$,
9) (C$_0$–C$_6$)alkylene-aryl, optionally substituted with up to three substituents selected from R$^e$,
10) (C$_0$–C$_6$)alkylene-heterocyclyl, optionally substituted with up to three substituents selected from R$^e$,
11) (C$_0$–C$_6$)alkylene-N(R$^e$)$_2$,
12) C(O)R$^c$,
13) CO$_2$R$^c$,
14) C(O)H, and
15) CO$_2$H; and R$^e$ is H, (C$_1$–C$_6$)alkyl, aryl, heterocyclyl, (C$_3$–C$_6$)cycloalkyl or S(O)$_2$R$^c$.

Yet another embodiment is the compound of Formula I described immediately above wherein Z is C—R$^4$, Y is S, X—W is C—C, and Q is absent.

Also within the scope of the present invention is the compound described directly above wherein R$^1$ is (C$_1$–C$_{10}$)alkylene-NR$^a$R$^b$, optionally substituted with one or two substituents selected from R$^7$;

R$^2$ is selected from:
1) H,
2) O$_r$(C$_1$–C$_3$)perfluoroalkyl,
3) OH,
4) CN,
5) halogen,
6) (C=O)$_r$O$_s$(C$_1$–C$_6$)alkyl,
7) (C=O)$_r$O$_s$(C$_2$–C$_6$)cycloalkyl,
8) (C=O)$_r$O$_s$(C$_2$–C$_6$)alkenyl,
9) (C=O)$_r$O$_s$(C$_2$–C$_6$)alkynyl,
10) (C=O)$_r$O$_s$aryl, and
11) NR$^a$R$^b$,
   wherein r and s are independently 0 or 1, and said alkyl, cycloalkyl, alkenyl, alkynyl, and aryl is optionally substituted with one or two substituents selected from R$^7$;

R$^4$ is H or (C$_1$–C$_6$)alkyl;

R$^5$ is selected from:
1) H,
2) SO$_2$R$^c$,
3) (C=O)$_r$R$^c$, wherein r is 0 or 1, and
4) CO$_2$R$^c$;

R$^6$ is selected from:
1) aryl, wherein aryl is defined as phenyl or naphthyl,
2) (C$_3$–C$_6$)cycloalkyl
3) (C$_1$–C$_6$)alkyl,
4) (C$_2$–C$_6$)alkenyl,
5) (C$_2$–C$_6$)alkynyl, and
6) heterocyclyl,
   wherein r and s are independently 0 or 1, and said aryl, cycloalkyl, alkyl, alkenyl, alkynyl and heterocyclyl optionally substituted with one or two substituents selected from R$^7$;

R$^7$ is selected from:
1) O$_r$(C=O)$_s$NR$^a$R$^b$,
2) (C=O)$_r$O$_s$aryl,
3) (C=O)$_r$O$_s$-heterocyclyl,
4) halogen,
5) OH,
6) oxo,
7) O(C$_1$–C$_3$)perfluoroalkyl,
8) (C$_1$–C$_3$)perfluoroalkyl, and
9) (C=O)$_r$O$_s$(C$_1$–C$_6$)alkyl,
10) CHO,
11) CO$_2$H,
12) CN,
13) (C$_3$–C$_6$)cycloalkyl,
   wherein r and s are independently 0 or 1, and said aryl, heterocyclyl and cycloalkyl are optionally substituted with one, two or three substituents selected from R$^d$;

R$^a$ and R$^b$ are independently selected from:
1) H,
2) (C=O)$_r$(C$_1$–C$_6$)alkyl,
3) (C=O)$_r$(C$_3$–C$_6$)cycloalkyl,
4) S(O)$_2$R$^c$,
5) (C=O)$_r$heterocyclyl,
6) (C=O)$_r$aryl, and
7) CO$_2$R$^c$,
   wherein r is 0 or 1 and said alkyl, cycloalkyl, heterocyclyl; and aryl optionally substituted with one to three substituents selected from R$^d$, or R$^a$ and R$^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one to three substituents selected from R$^d$;

R$^c$ is (C$_1$–C$_6$)alkyl, (C$_3$–C$_6$)cycloalkyl, or aryl; and

R$^d$ is selected from:
1) (C=O)$_r$O$_s$(C$_1$–C$_6$)alkyl, wherein r and s are independently 0 or 1, optionally substituted with up to three substituents selected from OH, (C$_1$–C$_6$)alkoxy, halogen, CN, oxo, N(R$^e$)$_2$ and S(O)$_2$R$^c$,
2) O$_r$(C$_1$–C$_3$)perfluoroalkyl,
3) (C$_0$–C$_6$)alkylene-S(O)$_m$R$^c$, wherein m is 0, 1, or 2,
4) oxo,
5) OH, 6) halo,
7) CN,
8) ($C_3$–$C_6$)cycloalkyl, optionally substituted with up to three substituents selected from OH, ($C_1$–$C_6$)alkoxy, halogen, CN, oxo, N($R^e$)$_2$ and S(O)$_2$$R^c$,
9) ($C_0$–$C_6$)alkylene-aryl, optionally substituted with up to three substituents selected from $R^e$,
10) ($C_0$–$C_6$)alkylene-heterocyclyl, optionally substituted with up to three substituents selected from $R^e$,
11) ($C_0$–$C_6$)alkylene-N($R^e$)$_2$,
12) C(O)$R^c$,
13) CO$_2$$R^c$,
14) C(O)H, and
15) CO$_2$H; and
$R^e$ is H, ($C_1$–$C_6$)alkyl, aryl, heterocyclyl, ($C_3$–$C_6$) cycloalkyl or S(O)$_2$$R^c$.

A further embodiment is the compound described above wherein
$R^1$ is ($C_1$–$C_{10}$)alkylene-NR$^a$R$^b$, optionally substituted with one or two substituents selected from $R^7$;
$R^2$ is H, CN, halogen, ($C_1$–$C_6$)alkyl, or ($C_1$–$C_6$)alkyloxy;
$R^4$ is H or ($C_1$–$C_6$)alkyl;
$R^5$ is H, ($C_1$–$C_6$)alkyl, CO$_2$($C_1$–$C_6$)alkyl, or CO($C_1$–$C_6$) alkyl;
$R^6$ is phenyl, ($C_1$–$C_6$)alkyl, thienyl, naphthyl, pyrimidinyl, pyridazinyl, pyrazinyl, or pyridyl, optionally substituted with one or two substituents selected from CN, halogen, ($C_1$–$C_6$)alkyl, or ($C_1$–$C_6$)alkyloxy, CF$_3$, OH, OCF$_3$, and NR$^a$R$^b$;
$R^7$ is selected from:
1) O$_r$(C=O)$_s$NR$^a$R$^b$,
2) (C=O)$_r$O$_s$aryl,
3) (C=O)$_r$O$_s$-heterocyclyl,
4) halogen,
5) OH,
6) oxo,
7) O($C_1$–$C_3$)perfluoroalkyl,
8) ($C_1$–$C_3$)perfluoroalkyl, and
9) (C=O)$_r$O$_s$($C_1$–$C_6$)alkyl,
10) CHO,
11) CO$_2$H,
12) CN,
13) ($C_3$–$C_6$)cycloalkyl,
wherein r and s are independently 0 or 1, and said aryl, heterocyclyl and cycloalkyl are optionally substituted with one or two substituents selected from $R^d$;
$R^a$ and $R^b$ are independently selected from:
1) H,
2) (C=O)$_r$($C_1$–$C_6$)alkyl,
3) (C=O)$_r$($C_3$–$C_6$)cycloalkyl,
4) S(O)$_2$$R^c$,
5) (C=O)$_r$heterocyclyl,
6) (C=O)$_r$aryl, and
7) CO$_2$$R^c$,
wherein r is 0 or 1 and said alkyl, cycloalkyl, heterocyclyl, and aryl optionally substituted with one to three substituents selected from $R^d$, or
$R^a$ and $R^b$ are taken together with the nitrogen to which they are attached to form a monocyclic or bicyclic heterocycle with 5–7 members in each ring and optionally containing, in addition to the nitrogen, one additional heteroatom selected from N, O and S, said monocyclic or bicyclic heterocycle optionally substituted with one or two substituents selected from $R^d$;
$R^c$ is ($C_1$–$C_6$)alkyl, ($C_3$–$C_6$)cycloalkyl, or aryl; and
$R^d$ is selected from:
1) (C=O)$_r$O$_s$($C_1$–$C_6$)alkyl, wherein r and s are independently 0 or 1, optionally substituted with up to three substituents selected from OH, ($C_1$–$C_6$)alkoxy, halogen, CN, oxo, N($R^e$)$_2$ and S(O)$_2$$R^c$,
2) O$_r$($C_1$–$C_3$)perfluoroalkyl,
3) ($C_0$–$C_6$)alkylene-S(O)$_m$$R^c$, wherein m is 0, 1, or 2,
4) oxo,
5) OH,
6) halo,
7) CN,
8) ($C_3$–$C_6$)cycloalkyl, optionally substituted with up to three substituents selected from OH, ($C_1$–$C_6$)alkoxy, halogen, CN, oxo, N($R^e$)$_2$ and S(O)2$R^c$,
9) ($C_0$–$C_6$)alkylene-aryl, optionally substituted with one or two substituents selected from Re,
10) (C–$C_6$)alkylene-heterocyclyl, optionally substituted with one or two substituents selected from $R^e$,
11) ($C_0$–$C_6$)alkylene-N($R^e$)$_2$,
12) C(O)$R^c$,
13) CO$_2$$R^c$,
14) C(O)H, and
15) CO$_2$H; and
$R^e$ is H, ($C_1$–$C_6$)alkyl, aryl, heterocyclyl, ($C_3$–$C_6$) cycloalkyl or S(O)$_2$$R^c$.

And yet another embodiment is a compound selected from:
2-[4-(4-methyl-5-oxo-[1,4]diazepan-1-ylmethyl)-pyridin-2-ylamino]-thiazole-5-carbonitrile;
2-[4-(4-acetyl-piperazin-1-ylmethyl)-pyridin-2-ylamino]-thiazole-5-carbonitrile;
2-[4-(4-methanesulfonyl-piperazin-1-ylmethyl)-pyridin-2-ylamino]-thiazole-5-carbonitrile;
2-[4-(1,1-dioxo-thiomorpholin-4-ylmethyl)-pyridin-2-ylamino]-thiazole-5-carbonitrile;
2-{4-[4-(2-hydroxy-ethanoyl)-piperazin-1-ylmethyl]-pyridin-2-ylamino}-thiazole-5-carbonitrile;
N-{1-[2-(5-cyano-thiazol-2-ylamino)-pyridin4-ylmethyl]-pyrrolidin-3-yl}-methanesulfonamide;
4-({2-[(5-cyano-1,3-thiazol-2-yl)amino]-4-pyridinyl}-methyl)-N,N-dimethyl-1-piperazinecarboxamide;
2-[(4-{[(5-oxo-3-pyrrolidinyl)amino]methyl }-2-pyridinyl)amino]-1,3-thiazole-5-carbonitrile;
4-({2-[(5-cyano-1,3-thiazol-2-yl)amino]-4-pyridinyl}methyl)-1-piperazinecarboxamide;
2-[(4-{[3-(methylsulfonyl)-1-pyrrolidinyl]methyl}-2-pyridinyl)amino]-1,3-thiazole-5-carbonitrile;
2-[4-(4-methyl-3-oxo-piperazin-1-ylmethyl)-pyridin-2-ylamino]-thiazole-5-carbonitrile;
2-(4-morpholin-4-ylmethyl-pyridin-2-ylamino)-thiazole-5-carbonitrile;
2-(4-{[(piperidin-4-ylmethyl)-amino]-methyl}-pyridin-2-ylamino)-thiazole-5-carbonitrile; and
2-(4-piperazin-1-ylmethyl-pyridin-2-ylamino)-thiazole-5-carbonitrile, or a use pharmaceutically acceptable salt or N-oxide thereof.

Another embodiment is a compound selected from:
[4-(4-methanesulfonyl-piperazin-1-ylmethyl)-pyridin-2-yl]-(5-phenyl-thiazol-2-yl)-amine;

1-methyl-4-[2-(5-phenyl-thiazol-2-ylamino)-pyridin-4-ylmethyl]-piperazin-2-one;
1-{4-[2-(5-phenyl-thiazol-2-ylamino)-pyridin-4-ylmethyl]-piperazin-1-yl}-ethanone;
1-ethyl-4-[2-(5-phenyl-thiazol-2-ylamino)-pyridin-4-ylmethyl]-piperazine-2,3-dione;
(5-phenyl-thiazol-2-yl)-(4-pyrrolidin-1-ylmethyl-pyridin-2-yl)-amine;
(5-phenyl-thiazol-2-yl)-[5-(3-piperidin-1-yl-propyl)-pyridin-2-yl]-amine;
1-[2-(5-phenyl-thiazol-2-ylamino)-pyridin-4-ylmethyl]-piperidine-4-carboxylic acid;
1-[2-(5-phenyl-thiazol-2-ylamino)-pyridin-4-ylmethyl]-piperidine-3-carboxylic acid; and
1-[2-(5-phenyl-thiazol-2-ylamino)-pyridin-4-ylmethyl]-piperidine-2-carboxylic acid, or a pharmaceutically acceptable salt or N-oxide thereof.

Also included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, cioblastomas and breast carcinoma.

Also included is a method of treating or preventing a disease in which angiogenesis is implicated, which is comprised of administering to a mammal in need of such treatment a therapeutically effective amount of a compound of Formula I. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula 1. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of compound of Formula 1 is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula 1 in combination with radiation therapy and/or in combination with a compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula 1 in combination with paclitaxel or trastuzumab.

Also within the scope of the invention is a method of reducing or preventing tissue damage following a cerebral ischemic event which comprises administering a therapeutically effective amount of a compound of Formula I.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

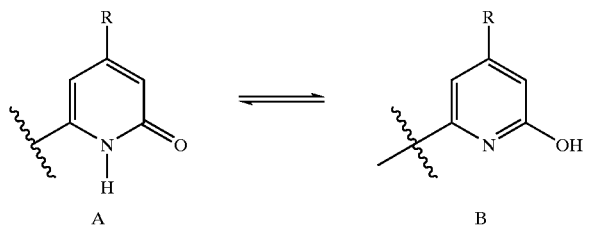

When any variable (e.g. $R^d$, $R^e$, $R^7$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched, straight-chain, and cyclic saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear, branched, or cyclic arrangement. For example, "$C_1$–$C_{10}$ alkyl" specifically includes methyl, ethyl, propyl, butyl, pentyl, hexyl, heptyl, octyl, nonyl, decyl, and so on, as well as cycloalkyls such as cyclopropyl, cycobutyl, cycopentyl, cycohexyl, tetrahydronaphthalene, methylenecylohexyl, and so on. "Alkoxy" indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$) alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The alkyl, alkenyl, alkynyl, cycloalkyl, aryl, heteroaryl and heterocyclyl substituents may be unsubstituted or unsubstituted, unless specifically defined otherwise. For example, a ($C_1$–$C_6$)alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C=O)$CH_2$CH(OH)$CH_3$, —(C=O)OH, —$CH_2$(OH)$CH_2$CH(O), and so on.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

A preferred definition of X—W is C—C. Preferably Y is O or S. More preferably Y is S. Z is preferably C—H. Preferably Q is absent. A preferred definition of $R^1$ is ($C_1$–$C_{10}$)alkylene-$NR^aR^b$. Preferably $R^2$ is H, halogen, or ($C_1$–$C_6$)alkyl. More preferably $R^2$ is H. Preferably $R^4$ is H or ($C_1$–$C_6$)alkyl. More preferably $R^4$ is H. Preferably $R^5$ is H. Preferably $R^6$ is CN, (C=O)$NR^aR^b$, phenyl, ($C_1$–$C_6$) alkyl, thienyl, naphthyl, pyrimidinyl, pyridazinyl, pyrazinyl, or pyridyl. More preferably $R^6$ is CN.

In certain instances, $R^a$ and $R^b$ are defined such that they can be taken together with the nitrogen to which they are attached to form a monocyclic or bicyclic heterocycle with 5–7 members in each ring and optionally containing, in addition to the nitrogen, one or two additional heteroatoms selected from N, O and S, said heterocycle optionally substituted with one or more substituents selected from $R^d$. Examples of the heterocycles that can thus be formed include, but are not limited to the following, keeping in mind that the heterocycle is optionally substituted with one or more substituents chosen from $R^d$:

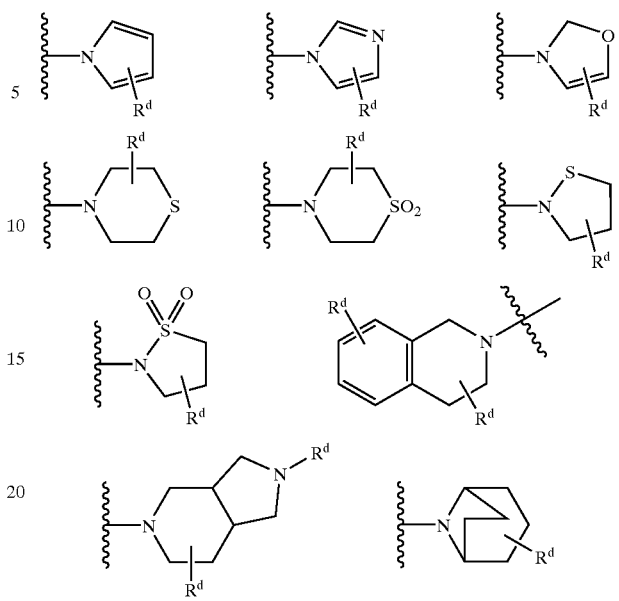

Preferably $NR^1R^b$ is chosen from the following:

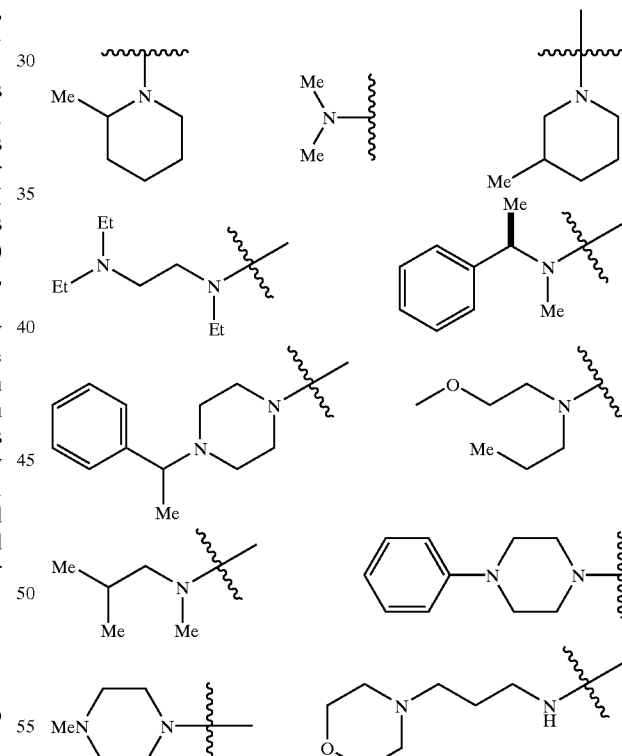

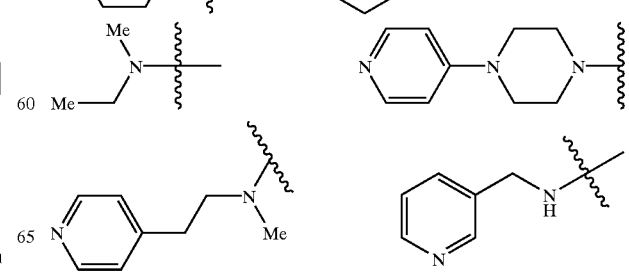

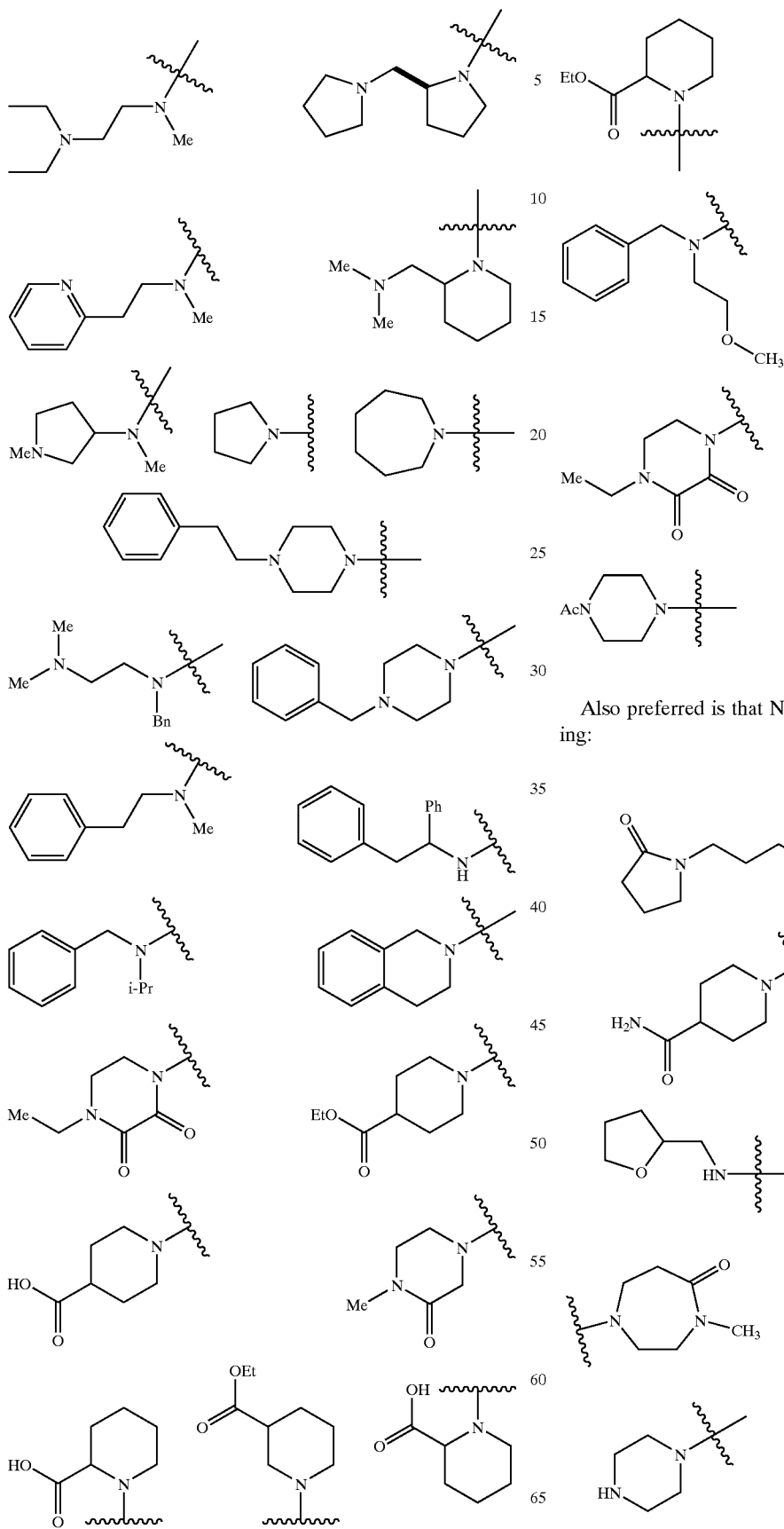
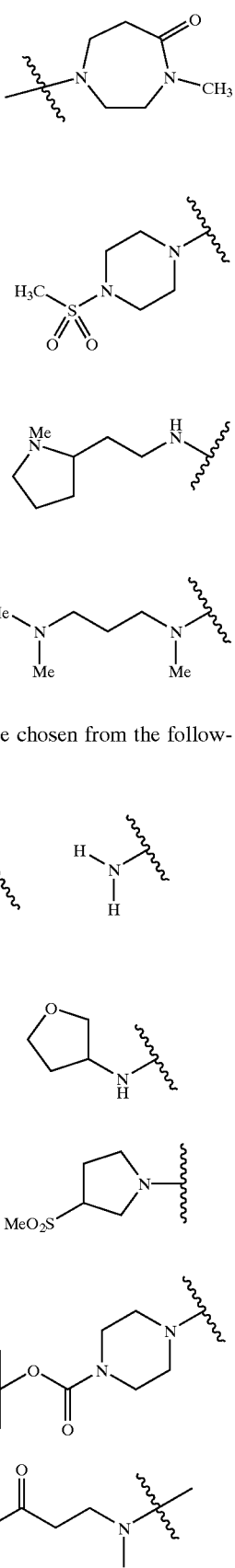
Also preferred is that $NR^aR^b$ be chosen from the following:

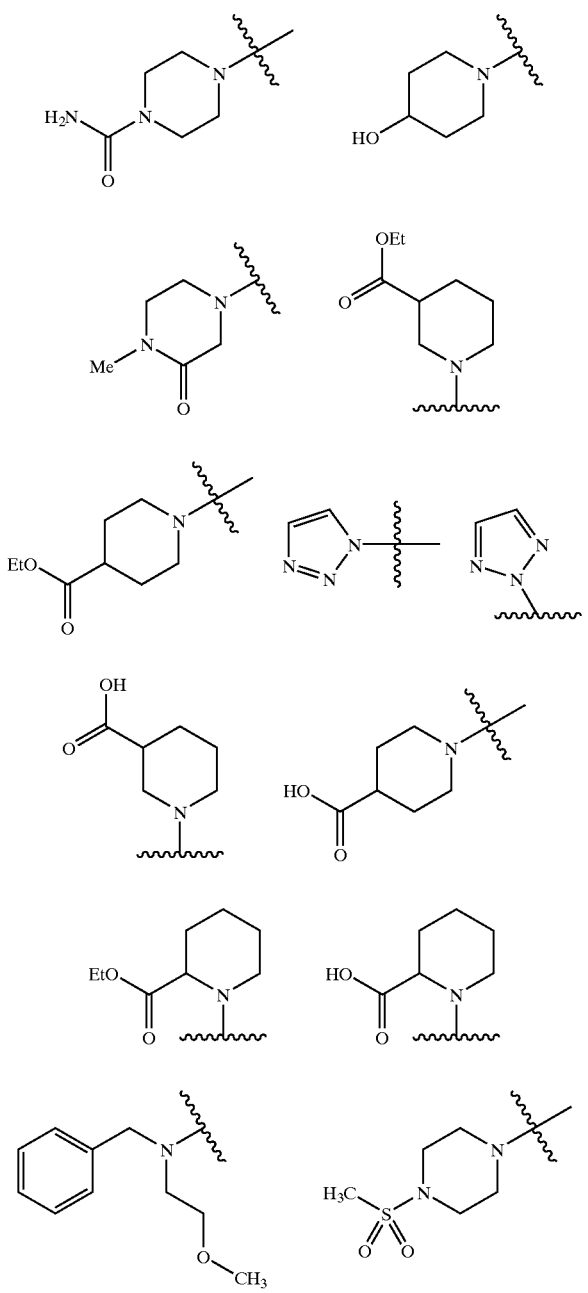
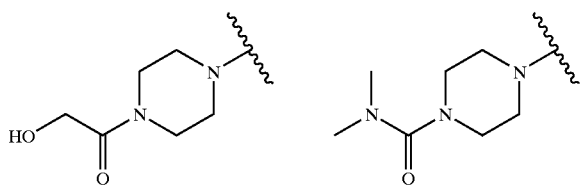
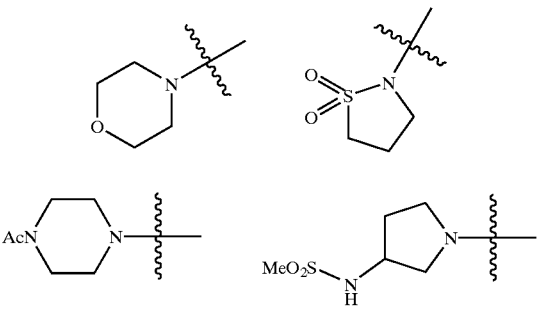

When $R^d$ is heterocyclyl, preferred definitions include pyridyl, pyrrolidinyl, pyrrolyl, piperidyl, morpholinyl, piperazinyl, furanyl, tetrahydrofuranyl, and dioxyl, optionally substituted with one, two or three substituents selected from $R^e$.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

The following chemical abbreviations are used in the present application:

| | | | |
|---|---|---|---|
| NCS | N-chlorosuccinimide | TBSCl | t-butyldimethylsilyl chloride |
| DMF | N,N-dimethylformamide | DMSO | dimethylsulfoxide |
| TsOH | p-toluenesulfonic acid | TFA | trifluoroacetic acid |
| EDC | 1-(3-dimethylamino-propyl)-3-ethylcarbo-diimide | BINAP | 2,2'-bis(diphenyl-phosphino)-1,1'-binaphthyl |
| THF | tetrahydrofuran | DCM | dichloromethane |
| DTT | dithiothreitol | EDTA | ethylenediamine tetracetic acid |
| RT | room temperature | DCE | dichloroethane |
| Fmoc | 9-fluorenylmethoxy-carbonyl | PCC | pyridinium chlorochromate |
| pyr | pyridine | LAH | lithium aluminium hydride |

Synopsis of Schemes

The thioureas A-2 required to make the disclosed compounds are available commercially or can be synthesized by one of the three alternate routes shown in Scheme A.

SCHEME A

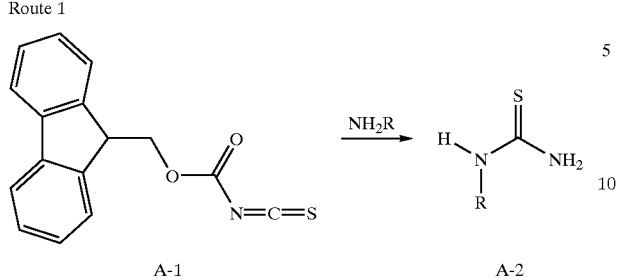

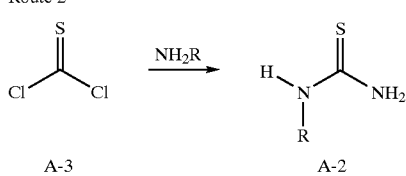

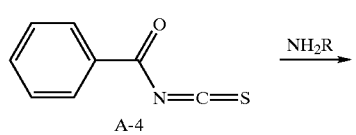

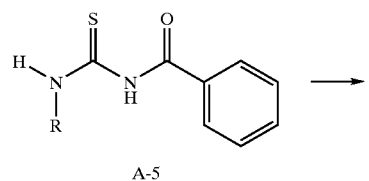

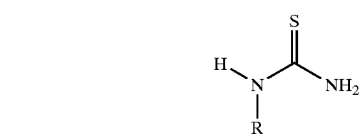

The target thiazoles B-3 and B-5 can be arrived at by reacting the appropriate thiourea B-2 with a bromo acetal B-1 or chloroacetaldehyde B-4 as shown in Scheme B. The analogous oxazole compounds can be synthesized via methods well known in the art.

SCHEME B

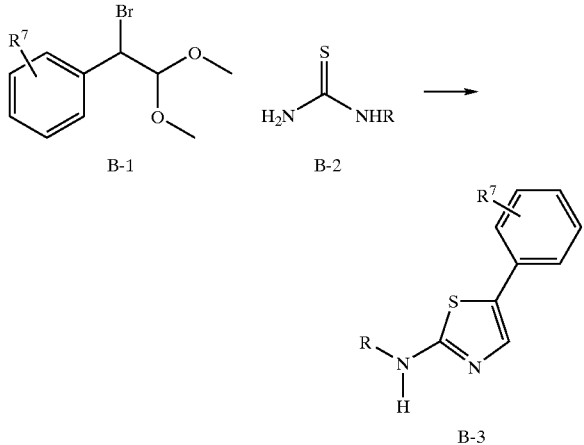

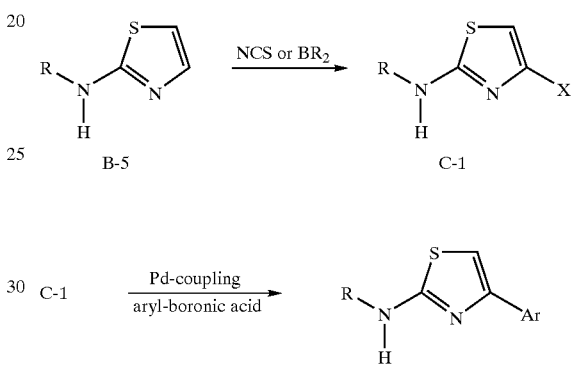

As shown in Scheme C, the resulting aminothiazole B-5 can be halogenated and C—C coupled to form adducts of the general structure C-2.

SCHEME C

Alternatively, the N—C bond-forming protocol illustrated in Scheme D can be used to obtain compounds of Formula D-6.

SCHEME D

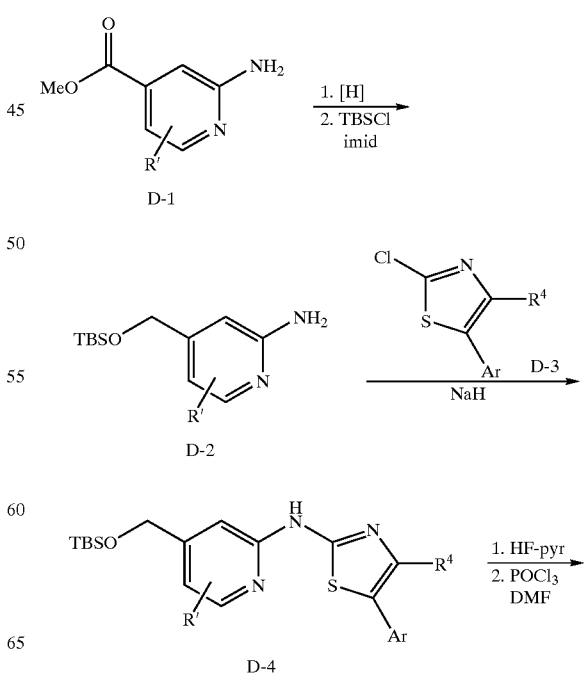

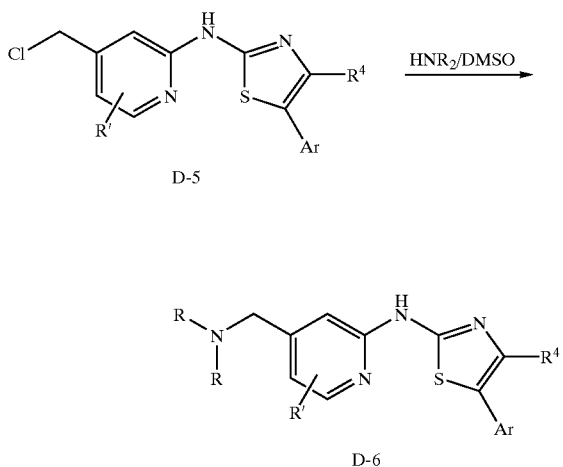

Utility

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. *Cancer Research*, 55:4575–4580, 1995). The anti-angiogenesis properties of the instant compounds are also useful in the treatment of certain forms of blindness related to retinal vascularization.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp.41–45, 1999; Gerber et al., Nature Medicine, Vol. 5, No. 6, pp.623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant compounds are also useful to treat and prevent conditions related to bone resorption, such as osteoporosis and Paget's disease.

The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine) platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethyl-xanthine, zorubicin, idarubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3', 4':b,7]indolizino[1,2b]quinoline-10,13(9H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxytoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol -6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethyl-aminomethyl)-6H-pyrazolo[4,5,1-de]acridin-6-one, N-[1-[2 (diethylamino)ethylamino]-7-methoxy-9-oxo-9H-thioxanthen-4-ylmethyl]formamide, N-(2-(dimethylamino) ethyl)acridine-4-carboxamide, 6-[[2-(dimethylamino)ethyl] amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]-glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4. 1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911, 165; 4,929,437; 5,189,164; 5,118,853; 5,290,946; 5,356, 896), atorvastatin (LIPITOR®; see U.S. Pat. Nos. 5,273, 995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

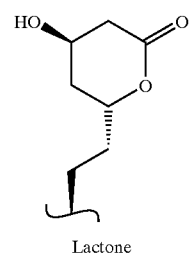

Lactone

I

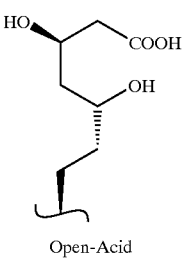

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl] piperidine, 4-{5-[4-Hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl }benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-Oxo-2H-[1,2'] bipyridin-5'-ylmethyl]-3H-imidazol-4-ylmethyl}benzonitrile, 4-[3-(2-Oxo-1-phenyl-1,2-dihydropyridin-4-ylmethyl)-3H-imidazol-4-ylmethyl ) benzonitrile, 18,19-dihydro-19-oxo-5H,17H-6,10:12,16-dimetheno-1H-imidazo[4,3-c][1,11,4]dioxaazacyclo-nonadecine-9-carbonitrile, (+)-19,20-Dihydro-19-oxo-5H-18,21-ethano-12,14-etheno-6,10-metheno-22H-benzo[d]imidazo[4,3-k] [1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriaza-cycloeicosine-9-carbonitrile, and (+)-19,20-Dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Pat. Publ. 0 618 221, European Pat. Publ. 0 675 112, European Pat. Publ. 0 604 181, European Pat. Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U. S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the for-nation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF. (see, Nature Biotechnology, Vol. 17, pp.963–968 (October 1999); Kim et al., Nature, 362, 841–844 (1993)).

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl ]-1H-1,2,3-triazole-4-carboxamide,CM101, squalamine, combretastatin, RP14610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl) methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_3$ integrin, to compounds which antagonize, inhibit or counteract binding of a physiological ligand to both the $\alpha_v\beta_3$ integrin and the $\alpha_v\beta_3$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$, and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl) indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX 1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6] benzodiazocin-1-one, SH268, genistein, ST1571, CEP2563, 4-(3-chlorophenylamino)-5,6-dimethyl-7H-pyrrolo[2,3-d] pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl4-(4-pyridylmethyl)-1-phthalazinamine, and EMD 121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the ainstant invention may alternatively be used sequentially with known pharmaceutically acceptable agent(s) when a combination formulation is inappropriate.

The term "administration" and variants thereof (e.g., "administering" a compound) in reference to a compound of the invention means introducing the N compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

Assays

The compounds of the instant invention described in the Examples were tested by the assays described below and were found to have kinase inhibitory activity. Other assays are known in the literature and could be readily performed by those of skill in the art. (see, for example, Dhanabal et al., *Cancer Res.* 59:189–197; Xin et al., *J. Biol. Chem.* 274:9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10×reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10×Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.
2. Add 35 μl of reaction mix containing 5 μl of 10×reaction buffer, 5 μl 25 mM ATP/10 μCi [$^{33}$P]ATP (Amersham), and 5 μl 10×substrate.
3. Start the reaction by the addition of 10 μl of KDR (25 nM) in enzyme dilution buffer.
4. Mix and incubate at room temperature for 15 minutes.
5. Stop by the addition of 50 μl stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3–7 below.

Culture Plates: NUNCLON 96-well polystyrene tissue culture plates (NUNC #167008).

Assay Medium: Dulbecco's modification of Eagle's medium containing 1 g/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1×concentration are made directly into Assay Medium immediately prior to addition to cells.

10×Growth Factors: Solutions of human $VEGF_{165}$ (500 ng/mL; R&D Systems) and bFGF (10 ng/mL; R&D Systems) are prepared in Assay Medium.

10×[$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) $Na_2CO_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% $CO_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.

3. After the 2-hour pretreatment period, cells are stimulated by addition of 10 μL/well of either Assay Medium, 10×VEGF solution or 10×bFGF solution. Cells are then incubated at 37° C. and 5% $CO_2$.

4. After 24 hours in the presence of growth factors, 10×[H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01-5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

EXAMPLES

Examples provided are intended to assist in a further understanding of the invention. Particular materials employed, species and conditions are intended to be further illustrative of the invention and not limiting of the reasonable scope thereof.

SCHEME 1

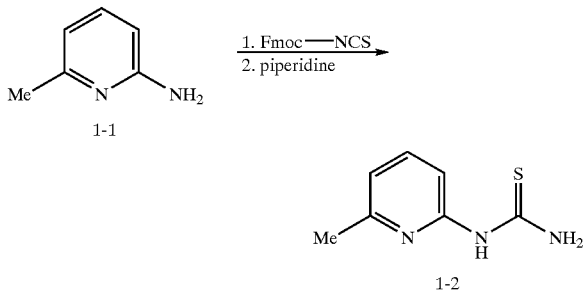

1.26 mM of the FMOC-NCS (fluorenylmethoxycarbonyl isothiocyanate, Kearney, P. C.; Fernandez, M.; Flygare, J. A. J.Org.Chem 1998, 63, 196–200) were dissolved in 5 mL $CH_2Cl_2$ to which 0.86 mM amine were slowly added at room temperature. When the FMOC reagent had been consumed, 2.5 mL of 20% piperdine in methanol were added. The reaction was allowed to stir at room temperature for 3 more hours before being washed with water, extracted with $CH_2Cl_2$, dried over $Na_2SO4$, and the organic layer concentrated. Removal of the FMOC byproducts by washing with hexane afforded the product, (6-methyl-pyridin-2-yl)-thiourea, 1-2, which was used without further purification. M+1=168.0. (5-Trifluoromethyl-pyridin-2-yl)-thiourea (1-3) was also made via this route. M+1=222.0.

SCHEME 2

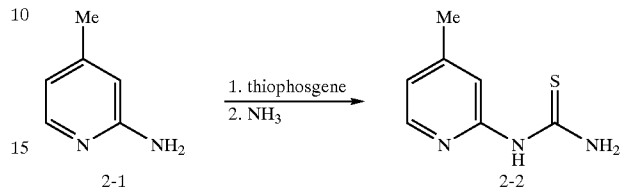

The amine was dissolved in dichloroethane, DCE (0.5 M). The flask was then cooled to 0° C. and two equivalents of triethylamine were added followed by 1.1 equivalents of thiophosgene. The reaction mixtures generally became viscous so more DCE was added. After two hours excess concentrated aqueous $NH_4OH$ was added. The flask was allowed to warm to room temp and left stirring overnight. The DCE was removed to afford the product, which was filtered and washed with water.

The following thioureas were synthesized via this route:
(4-Methyl-pyridin-2-yl)-thiourea (2-2),
(4,6-Dimethyl-pyridin-2-yl)-thiourea (2-3),
(5-Methyl-pyridin-2-yl)-thiourea (2-4), and
(5-chloro-pyridin-2-yl)-thiourea (2-5).

SCHEME 3

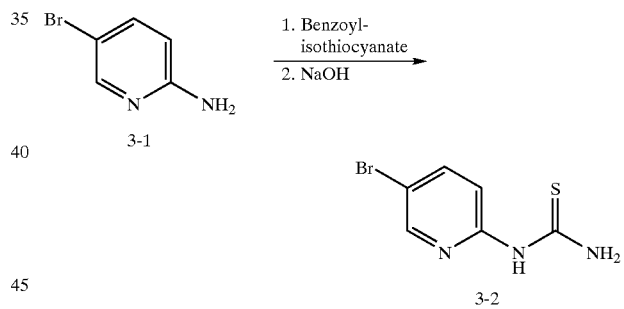

One equivalent of amine was combined with one equivalent of benzoyl isothiocyanate in a flame dried flask containing anhydrous dimethylformamide, DMF (0.5M). The reaction was stirred overnight under argon at room temperature. The DMF was then removed, and the remaining benzoyl compound refluxed in 3:1 THF (tetrahydrofuran):1 M aqueous NaOH. After three hours the THF was removed and the aqueous layer was brought to pH 8 and filtered when possible or extracted with methylene chloride. The methylene chloride layer was dried over $Na_2SO_4$ and concentrated to afford the desired product.

The following compounds were made via this route:
(5-Bromo-pyridin-2-yl)-thiourea (3-2),
6-Thioureido-pyridine-2-carboxylic acid methyl ester (3-3),
(6-Hydroxymethyl-pyridin-2-yl)-thiourea (3-4),
[5-(3-Hydroxy-propyl)-pyridin-2-yl]-thiourea (3-5),
(4-Hydroxymethyl-pyridin-2-yl)-thiourea (3-6),
Pyrimidin-2-yl-thiourea (3-7),
(5-Chloro-pyridin-2-yl)-thiourea (3-8),
(5-Hydroxymethyl-pyridin-2-yl)-thiourea (3-9), (3-Phenoxymethyl-pyridin-2-yl)-thiourea (3-10), (3-Bromo-5-methyl-pyridin-2-yl)-thiourea (3-11), and (3,5-Dichloro-pyridin-2-yl)-thiourea (3-12).

SCHEME 4

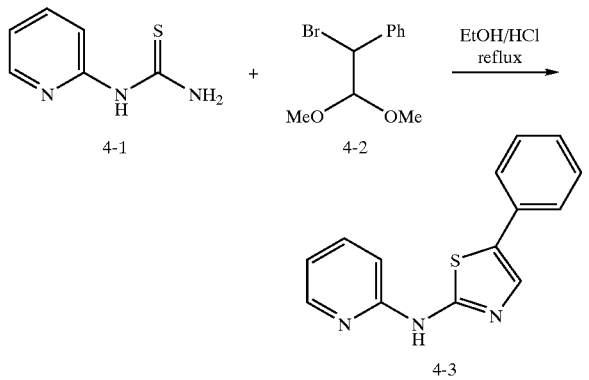

(1-Bromo-2,2-dimethoxy-ethyl)-benzene 4-2 (Bellesia, F.; Boni, M.; Ghelfi, F.; Pagnoni, U. M.; Gazz.Chim.Ital. 1993, 123, 629–632) (1.2 eq.) and the appropriate thiourea (1 eq.) were dissolved in 4:1 ethanol/HCl and heated to reflux while stirring overnight. The reaction mixture was then added to saturated sodium bicarbonate. The resulting precipitate was filtered and washed with ethyl acetate to give the desired thiazole. This work up gave compound 4-3, (5-Phenyl-thiazol-2-yl)-pyridin-2-yl-amine, with HPLC purity greater than 90%. $^1$H NMR (DMSO-$d_6$): δ11.36 (1H, s), 8.35 (1H, dd, J=5.8, 0.8 Hz), 7.80 (1H,s), 7.741–7.698 (1H, m), 7.60 (2H,d, J=7.2 Hz) 7.39 (2H, t, J=7.6 Hz) 7.25 (1H, t, J=7.4 Hz) 7.08 (1H,d, J=8.3 Hz), 6.95 (1H, dd, J=5.9, 5.1 Hz). MS [M+H]+=254.08. mp >200° C.

Compounds 4-4 through 4–18 below were synthesized via the procedure described above for 4-3. Most compounds were obtained with greater than 90% purity after work-up. Compounds that were not produced in the desired purity were purified by column chromatography or via preparative HPLC.

(5-Bromo-pyridin-2-yl)-(5-phenyl-thiazol-2-yl)-amine (4-4)

$^1$H NMR (DMSO-$d_6$) of HBr salt: δ11.58 (bs, 1H), 8.45 (d, 1H, J=2.5 Hz), 7.93 (dd, 1H, J=2.5, 8.8), 7.83 (s, 1H), 7.59 (d, 2H, J=7.4 Hz), 7.40 (t, 2H, J=7.6 Hz), 7.2 (t, 1H, J=7.2 Hz), 7.09 (d, 1H, J=8.9 Hz). mp >220° C.

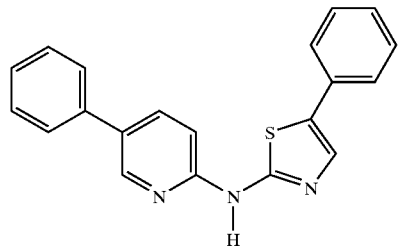

(5-Phenyl-pyridin-2-yl)-(5-phenyl-thiazol-2-yl)-amine (4-5)

$^1$H NMR(CDCl$_3$): δ8.67 (d, 1H, J=1.6 Hz), 7.76 (dd, 1H, J=6.1 Hz), 7.58 (m, 4H), 7.54 (s, 1H), 7.50 (t, 2H, J=7.3 Hz), 7.45 (t, 2H, J=7.2 Hz), 7.41 (t, 1H, J=9.4 Hz), 7.36 (t, 1H, J=7.3 Hz), 7.15 (d, 1H, J=8.5 Hz). Calculated for $C_{20}H_{15}N_3S$+0.60 molecules TFA(MW=397.84, Base MW=329.43, Salt/Base Ratio=1.208): C, 64.00; H, 3.95; N, 10.56. Found: C, 63.99; H, 3.83; N, 10.20. mp 231–233° C. MS [M+H]+=330.0.

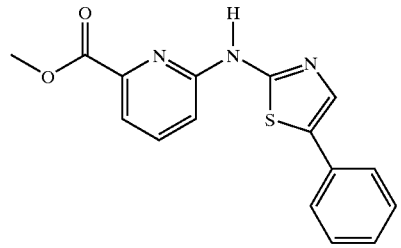

6-(5-Phenyl-thiazol-2-ylamino)-pyridine-2-carboxylic acid methyl ester (4-6)

$^1$H NMR(DMSO-$d_6$): δ11.62 (bs, 1H), 7.90 (t, 1H, J=8.3 Hz), 7.83 (s, 1H), 7.63 (d, 1H, J=7.3 Hz), 7.60 (dd, 2H, J=1.3, 8.4 Hz), 7.43 (t, 2H, J=7.8 Hz), 7.32 (d, 1H, J=8.3 Hz) 7.27 (t, 1H, J=7.3 Hz), 3.96 (s, 3H). Mp: 231–232° C. M+1:312.1.

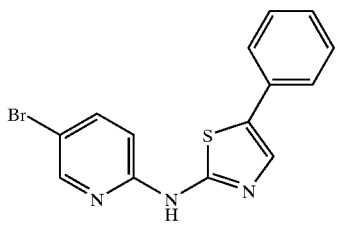

| No. | Structure | Name | MS (M + H) | MP |
|---|---|---|---|---|
| 4-7 | 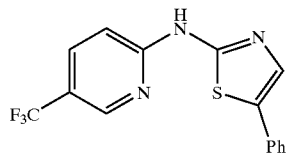 | (5-Phenyl-thiazol-2-yl)-(5-trifluoromethyl-pyridin-2-yl)-amine | 322 | >200 |

-continued

| No. | Structure | Name | MS (M + H) | MP |
|---|---|---|---|---|
| 4-8 | 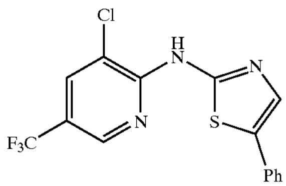 | (3-Chloro-5-trifluoromethyl-pyridin-2-yl)-(5-phenyl-thiazol-2-yl)-amine | 356 | 170 |
| 4-9 | 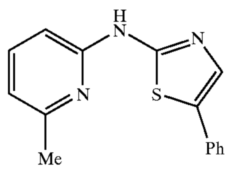 | (6-Methyl-pyridin-2-yl)-(5-phenyl-thiazol-2-yl)-amine | 268.1 | >200 |
| 4-10 | 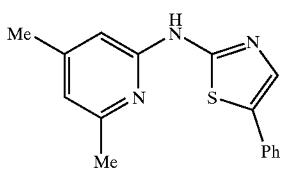 | (4,6-Dimethyl-pyridin-2-yl)-(5-phenyl-thiazol-2-yl)-amine | 282.1 | |
| 4-11 | 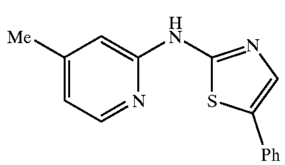 | (4-Methyl-pyridin-2-yl)-(5-phenyl-thiazol-2-yl)-amine | 268.1 | >200 |
| 4-12 | 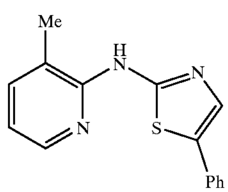 | (3-Methyl-pyridin-2-yl)-(5-phenyl-thiazol-2-yl)-amine | 268.1 | |
| 4-13 | 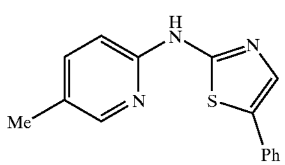 | (5-Methyl-pyridin-2-yl)-(5-phenyl-thiazol-2-yl)-amine | 268.1 | 233 |
| 4-14 | 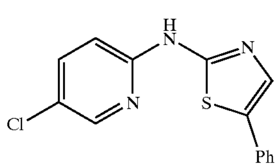 | (5-Chloro-pyridin-2-yl)-(5-phenyl-thiazol-2-yl)-amine | 288 | >250 |
| 4-15 | 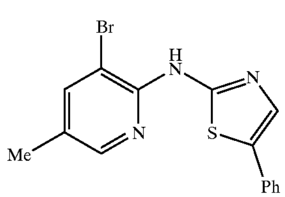 | (3-Bromo-5-methyl-pyridin-2-yl)-(5-phenyl-thiazol-2-yl)-amine | 345.9, 347.9 | 248 |

| No. | Structure | Name | MS (M + H) | MP |
|---|---|---|---|---|
| 4-16 | 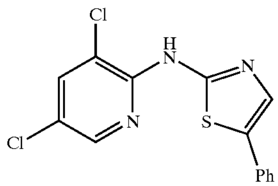 | (3,5-Dichloro-pyridin-2-yl)-(5-phenyl-thiazol-2-yl)-amine | 321.9, 323.9 | 238 |
| 4-17 | 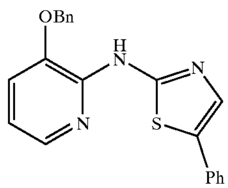 | (3-Benzyloxy-pyridin-2-yl)-(5-phenyl-thiazol-2-yl)-amine | 360.23 | |

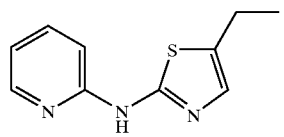

(5-Ethyl-thiazol-2-yl)-pyridin-2-yl-amine (4-18)

The procedure from above was followed substituting the 2-bromo-1,1-dimethoxy-butane for the (1-bromo-2,2-dimethoxy-ethyl)-benzene. 1H NMR (DMSO-d$_6$) δ10.99 (1H,s) 8.25 (1H,dd, J=1.83, 0.91 Hz) 7.67 (1H t, J=1.8 Hz) 7.05 (1H,s) 7.04 (1H,d, J=4.9 Hz) 6.88 (1H, t, J=4.94 Hz) 2.73 (2H,q, J=7.5 Hz), 1.23 (3H, t, J=7.5 Hz). mp=113° C. MS [M+H]+=206.1.

SCHEME 5

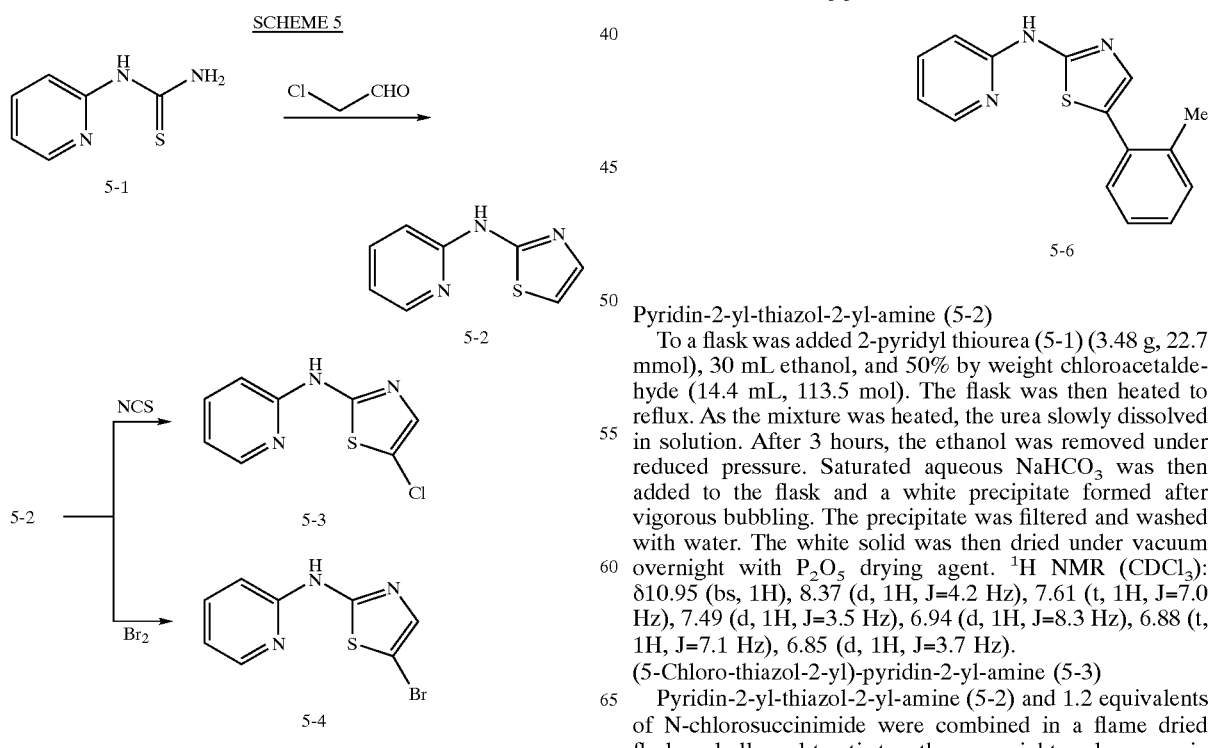

Pyridin-2-yl-thiazol-2-yl-amine (5-2)

To a flask was added 2-pyridyl thiourea (5-1) (3.48 g, 22.7 mmol), 30 mL ethanol, and 50% by weight chloroacetaldehyde (14.4 mL, 113.5 mol). The flask was then heated to reflux. As the mixture was heated, the urea slowly dissolved in solution. After 3 hours, the ethanol was removed under reduced pressure. Saturated aqueous NaHCO$_3$ was then added to the flask and a white precipitate formed after vigorous bubbling. The precipitate was filtered and washed with water. The white solid was then dried under vacuum overnight with P$_2$O$_5$ drying agent. $^1$H NMR (CDCl$_3$): δ10.95 (bs, 1H), 8.37 (d, 1H, J=4.2 Hz), 7.61 (t, 1H, J=7.0 Hz), 7.49 (d, 1H, J=3.5 Hz), 6.94 (d, 1H, J=8.3 Hz), 6.88 (t, 1H, J=7.1 Hz), 6.85 (d, 1H, J=3.7 Hz).

(5-Chloro-thiazol-2-yl)-pyridin-2-yl-amine (5-3)

Pyridin-2-yl-thiazol-2-yl-amine (5-2) and 1.2 equivalents of N-chlorosuccinimide were combined in a flame dried flask and allowed to stir together overnight under argon in anhydrous dioxane (0.25 M). The dioxane solution was then diluted with water and the resulting product filtered off. $^1$H-NMR (DMSO-d$_6$) δ11.463 (1H,s) 8.30 (dd, 1H, J=4.9, 0.9 Hz) 7.73 (t, 1H, J=8.42 Hz) 7.38 (s, 1H) 7.03 (d, 1H, J=8.4 Hz) 6.96 (t, 1H, J=5.9 Hz). MS [M+H]+=211.9.

(5-Bromo-thiazol-2-yl)-pyridin-2-yl-amine (5-4)

To a flask containing pyridin-2-yl-thiazol-2-yl-amine (5-2, 3.92 g, 0.0221 mol) was added acetic acid. Bromine (1.14 mL, 0.0221 mol) was then added dropwise to the stirred solution at ambient temperature. The reaction was stirred for 15 min, resulting in an orange-white precipitate. At 15 min, 100 mL H$_2$O were added and solid NaHCO$_3$ introduced, causing a large amount of foaming. The product was obtained as a tan colored precipitate, which was washed with 1.5 L H$_2$O and dried under high vacuum overnight. $^1$H NMR (DMSO-d$_6$): δ11.53 (bs, 1H), 8.31 (d, 1H, J=3.3 Hz), 7.73 (t, 1H, J=7.6 Hz), 7.45 (s, 1H), 7.05 (d, 1H, J=8.4 Hz), 6.96 (t, 1H, J=5.5 Hz). Mp: 210–212° C. (dec.) [M+H]+= 255.9.

N-(5-Bromo-thiazol-2-yl)-N-pyridin-2-yl-acetamide (5-5)

To a flask containing (5-Bromo-thiazol-2-yl)-pyridin-2-yl-amine (5-4, 4.58 g, 17.9 mmol was added 30 mL acetic anhydride. The suspension was then heated to 100° C. After about 1.5 hours, the acetic anhydride and acetic acid was removed under reduced pressure, heating the bath to 70° C. Two 70 mL portions of toluene were also added for azeotropic distillation. The product was obtained as a tan colored precipitate. $^1$H NMR (DMSO-d$_6$): δ8.65 (d, 1H, J=3.9 Hz), 8.09 (t, 1H, J=8.6 Hz), 7.67 (d, 1H, J=8 Hz), 7.59 (t, 1H, J=6.6 Hz), 7.47 (s, 1H). mp 132–138° C.

Pyridin-2-yl-(5-o-tolyl-thiazol-2-yl)-amine (5-6)

To a flame dried round bottom flask previously flushed with argon was added N-(5-bromo-thiazol-2-yl)-N-pyridin-2-yl-acetamide (5-5) (50 mg, 1.7 mmol, o-tolylboronic acid (2.6 mmol), potassium phosphate tribasic (108 mg, 5.1 mmol), palladium tetrakistriphenyl phosphine (20 mg, 0.2 mmol), and 3 mL of anhydrous dioxane. The vessel was flushed twice with argon and was heated to 100° C. under Argon. After 20 h workup was performed as follows: The reaction was cooled to ambient temperature and the dioxane was removed via rotary evaporation. The crude mixture was diluted in 1.5 mL CH$_2$Cl$_2$ and 2 mL water, and the resulting biphasic mixture was transferred to a Whatman 12 mL 1PS filter tube. The layers were mixed and the organic layer was drained into a collection tube; the extraction was repeated with an additional 2 mL of CH$_2$Cl$_2$. The organic layer was concentrated and the resulting solid was dissolved in DMSO. Purification was performed via Gilson reverse phase automated column chromatography. Only pure desired fractions were combined into a reaction vessel, contaminated fractions were discarded. An equal portion of methanol was added corresponding to the volume of acetonitrile/water present in the combined samples. LiOH monohydrate (5.0 eq.) was added to the stirred solution. The reaction was complete via MS within 10 min or less after the addition of the LiOH. The reaction was concentrated to almost complete dryness. The product was obtained as a precipitate which was filtered, washed with water, and dried. $^1$H NMR (CDCl$_3$): δ8.38 (d, 1H, J=4.2 Hz), 7.68 (t, 1H, J=7.5 Hz), 7.42 (d, 1H, J=9.7 Hz), 7.33 (s, 1H), 7.27–7.31 (m, 3H), 7.08 (d, 1H, J=8.2 Hz), 6.97 (t, 1H, J=4.9 Hz), 2.46 (s, 3H). Mp: 155–160° C. MS [M+H]+=268.0.

The following examples were synthesized by the same procedure:

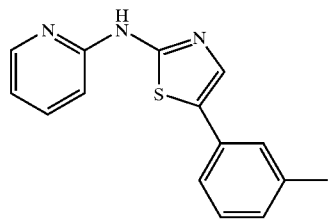

Pyridin-2-yl-(5-m-tolyl-thiazol-2-yl)-amine (5-7)
$^1$H NMR (CDCl$_3$): δ10.21 (bs, 1H), 8.42 (d, 1H, J=4.6 Hz), 7.64 (s, 1H), 7.64 (t, 1H, J=7.3 Hz), 7.43 (s, 1H), 7.42 (d, 1H, J=7.0 Hz), 7.29 (t, 1H, J=7.6 Hz), 7.09 (d, 1H, J=7.7 Hz), 6.93 (d, 1H, J=8.3 Hz), 6.92 (t, 1H, J=8.3 Hz), 2.41 (s, 3H). Mp: 204–205° C. M+1: 268.0. Mp: 204–205° C.

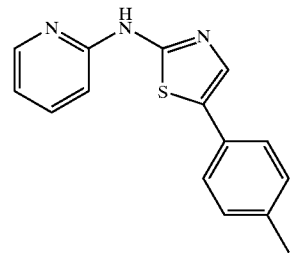

Pyridin-2-yl-(5-p-tolyl-thiazol-2-yl)-amine (5-8)
$^1$H NMR (CDCl$_3$): δ9.87 (bs, 1H), 8.40 (dd, 1H, J=5.3 Hz), 7.63 (td, 1H, J=8.1 Hz), 7.60 (s, 1H), 7.49 (d, 2H, J=8.1 Hz), 7.20 (d, 2H, J=7.8 Hz), 6.89–6.92 (m, 2H), 2.38 (s, 3H). M+1: 268.0.

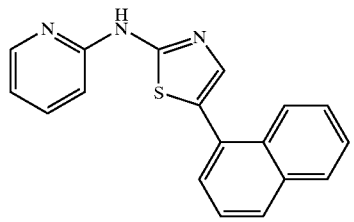

(5-Naphthalen-1-yl-thiazol-2-yl)-pyridin-2-yl-amine (5-9)
$^1$H NMR (CDCl$_3$): δ10.88 (bs, 1H), 8.37 (dd, 1H, J=4.9 Hz), 8.32 (dd, 1H, J=6.2 Hz), 7.91 (dd, 1H, J=8.5 Hz), 7.87 (d, 1H, J=8.2 Hz), 7.60–7.65 (m, 2H), 7.61 (s, 1H), 7.50–7.55(m, 3H), 6.99 (d, 1H, J=8.3 Hz), 6.89 (td, 1H, J=7.3 Hz). M+1: 304.2. Mp: 223.5–226° C.

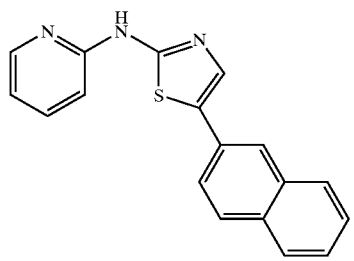

(5-Naphthalen-2-yl-thiazol-2-yl)-pyridin-2-yl-amine (5-10)
$^1$H NMR (CDCl$_3$-CD$_3$OD): δ8.42 (dd, 1H, J=5 Hz), 7.99 (d, 1H, J=1.1 Hz), 7.85 (d, 2H, J=8.3 Hz), 7.82 (d, 1H, J=7.8 Hz), 7.73 (dd, 1H, J=8.5 Hz), 7.68 (s, 1H), 7.64 (td, 1H, J=7.0 Hz), 7.50 (td, 1H, J=6.6 Hz), 7.45 (td, 1H, J=6.6 Hz), 6.95 (d, 1H, J=8.3 Hz), 6.93 (td, 1H, J=6.6 Hz). M+1: 304.2. Mp: 230–232.5° C.

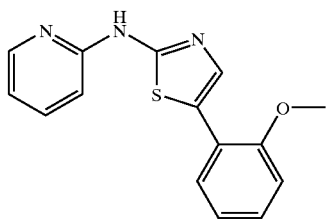

[5-(2-Methoxy-phenyl)-thiazol-2-yl]-pyridin-2-yl-amine (5-11)

$^1$H NMR (CDCl$_3$): δ9.24 (bs, 1H), 8.40 (dd, 1H, J=5.0 Hz), 7.84 (s, 1H), 7.60–7.64 (m, 2H), 7.26 (td, 1H, J=8.1 Hz), 7.00 (td, 2H, J=8.9 Hz), 6.93 (d, 1H, J=8.3 Hz), 6.90 (td, 1H, J=7.1 Hz), 3.97 (s, 3H). MS [M+H]+=284.2.

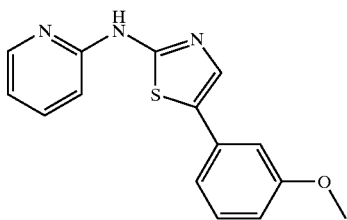

[5-(3-Methoxy-phenyl)-thiazol-2-yl]-pyridin-2-yl-amine (5-12)

$^1$H NMR (CDC$_3$): δ10.28 (bs, 1H), 8.41 (dd, 1H, J=5.6 Hz), 7.66 (s, 1H), 7.65 (td, 1H, J=9.8 Hz), 7.31 (t, 1H, J=7.9 Hz), 7.21 (d, 1H, J=6.6 Hz), 7.14 (t, 1H, J=2.0 Hz), 6.93 (d, 1H, J=8.0 Hz), 6.91 (td, 1H, J=2.0 Hz), 6.80 (dd, 1H, J=8.0 Hz), 3.88 (s, 3H). M+1: 284.2. Mp: 170–171.5° C.

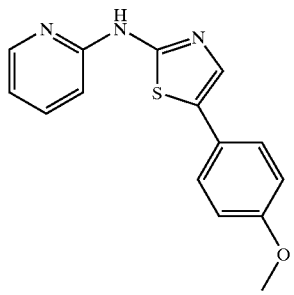

[5-(4-methoxy-phenyl)-thiazol-2-yl]-pyridin-2-yl-amine (5-13)

$^1$H NMR (DMSO-d$_6$): δ11.26 (bs, 1H), 8.33 (dd, 1H, J=0.9, 5.0 Hz), 7.69 (dt, 1H, J=1.8, 8.8 Hz), 7.64 (s, 1H), 7.50 (d, 2H, J=11.8 Hz), 7.06 (d, 1H, 8.3 Hz), 6.97 9d, 2H, J=8.8 Hz), 6.93 (dd, 1H, J=5.1, 6.3 Hz), 3.78 (s, 3H). M+1: 284.0.

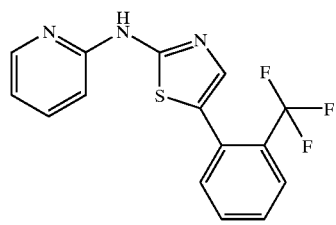

Pyridin-2-yl[5-(2-trifluoromethyl-phenyl)-thiazol-2-yl-amine (5-14)

$^1$H NMR (CDCl$_3$): δ10.13 (bs, 1H), 8.36 (d, 1H, J=4.0 Hz), 7.78 (d, 1H, J=7.7 Hz), 7.62 (td, 1H, J=9.2 Hz), 7.57 (d, 1H, J=3.9 Hz), 7.48 (t, 1H, J=5.1 Hz), 7.45 (s, 1H), 6.90 (d, 1H, J=8.4 Hz), 6.89 (t, 1H, J=5.3 Hz). M+1: 322.2. Mp: 195–203° C.

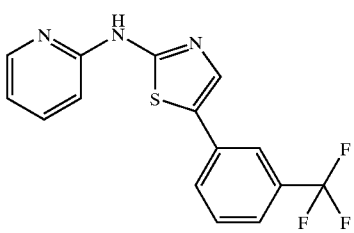

Pyridin-2-yl-[5-(3-trifluoromethyl-phenyl)-thiazol-2-yl]-amine (5-15)

$^1$H NMR (CDCl$_3$): δ9.87 (bs, 1H), 8.44 (dd, 1H, J=6.0 Hz), 7.83 (s, 1H), 7.77 (t, 1H, J=1.3 Hz), 7.71 (s, 1H), 7.67 (td, 1H, J=9.1 Hz), 7.50–7.52 (m, 2H), 6.95 (td, 1H, J=7.2Hz), 6.91 (d, 1H, J=8.4 Hz). M+1: 322.0. Mp: 242–244° C.

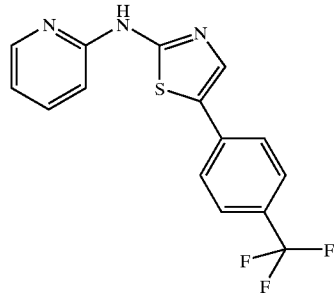

Pyridin-2-yl-5-(4-trifluoromethyl-phenyl)-thiazol-2-yl]-amine (5-16)

$^1$H NMR (CDCl$_3$-CD$_3$OD): δ8.40 (dd, 1H, J=4.0 Hz), 7.61–7.69 (m, 6H), 6.95 (s, 1H), 6.93 (t, 1H, J=3.7 Hz). M+1: 322.2. Mp: >250° C.

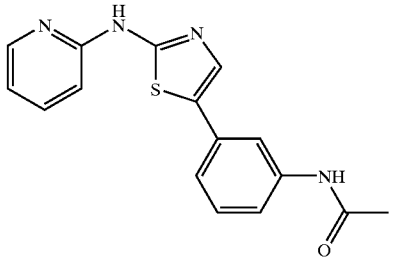

N-{3-[(Pyridin-2-ylamino)-thiazol-5-yl]-phenyl}-acetamide (5-17)

$^1$H NMR (CDCl$_3$-CD$_3$OD): δ8.36 (dd, 1H, J=4.2 Hz), 7.78 (s, 1H), 7.64 (td, 1H, J=3.9 Hz), 7.55 (s, 1H), 7.44–7.47 (m, 1H), 7.29–7.34 (m, 2H), 6.96 (d, 1H, J=8.3 Hz), 6.91 (td, 1H, J=5.7 Hz), 2.17 (s, 3H). M+1: 311.2.

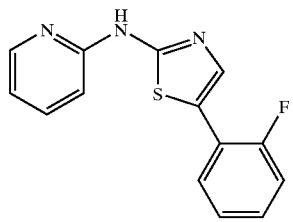

[5-(2-Fluoro-phenyl)-thiazol-2-yl]-pyridin-2-yl-amine (5-18)

$^1$H NMR (CDCl$_3$): δ9.64 (bs, 1H), 8.42 (d, 1H, J=4.1 Hz), 7.83 (d, 1H, J=1.6 Hz), 7.65 (td, 1H, J=7.5 Hz), 7.63 (td, 1H, J=9.1 Hz), 7.13–7.26 (m, 3H), 6.90–6.94 (m, 2H). M+1: 272.2. Mp: 227–228° C.

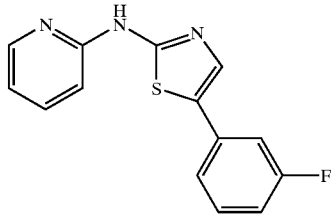

[5-(3-Fluoro-phenyl)-thiazol-2-yl]-pyridin-2-yl-amine (5-19)

$^1$H NMR (DMSO-d$_6$): δ11.44 (bs, 1H), 8.35 (dd, 1H, J=4.1 Hz), 7.91 (s, 1H), 7.73 (td, 1H, J=9.3 Hz), 7.41–7.50 (m, 3H), 7.06–7.10 (m, 2H), 6.96 (td, 1H, J=7.0 Hz). M+1: 272.2. Mp: >250° C.

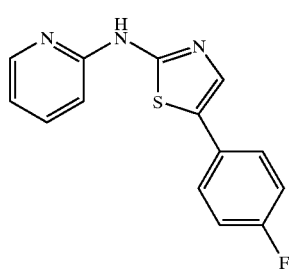

[5-(4-Fluoro-phenyl)-thiazol-2-yl]-pyrdin-2-yl-amine (5-20)

$^1$H NMR (CDCl$_3$-CD$_3$OD): δ8.37 (dd, 1H, J=5.2 Hz), 7.64 (td, 1H, J=8.3 Hz), 7.51–7.56 (m, 2H), 7.47 (s, 1H), 7.06–7.11 (m, 2H), 6.90–6.96 (m, 2H). M+1: 272.2. Mp: 239–240° C.

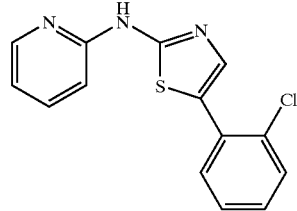

[5-(2-Chloro-phenyl)-thiazol-2-yl]-pyridin-2-yl-amine (5-21)

$^1$H NMR (CDCl$_3$-CD$_3$OD): δ8.37 (dd, 1H, J=4.1 Hz), 7.64 (s, 1H), 7.63 (td, 1H, J=8.5 Hz), 7.55 (dd, 1H, J=7.5 Hz), 7.48 (dd, 1H, J=7.8 Hz), 7.29 (td, 1H, J=7.5 Hz), 7.24 (td, 1H, J=7.6 Hz), 6.94 (d, 1H, J=8.3 Hz), 6.91 (td, 1H, J=7.0 Hz). M+1: 288.2. Mp: 213–215° C.

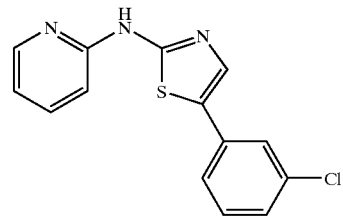

[5-(3-Chloro-phenyl)-thiazol-2-yl]-pyridin-2-yl-amine (5-22)

$^1$H NMR (DMSO-d$_6$): δ11.45 (s, 1H), 8.35 (dd, 1H, J=5.0 Hz), 7.92 (s, 1H), 7.73 (td, 1H, J=6.5 Hz), 7.67 (t, 1H, J=1.8 Hz), 7.55 (dd, 1H, J=8.4 Hz), 7.41 (t, 1H, J=7.9 Hz), 7.30 (dd, 1H, J=9.1 Hz), 7.09 (d, 1H, J=8.4 Hz), 6.97 (td, 1H, J=6.3 Hz). M+1: 288.2. Mp: 242–243° C.

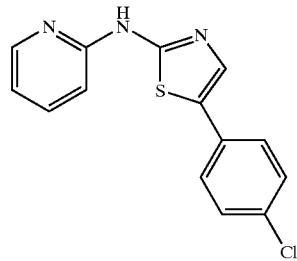

[5-(4-Chloro-phenyl)-thiazol-2-yl]-pyridin-2-yl-amine (5-23)

$^1$H NMR (DMSO-d$_6$): δ11.40 (bs, 1H), 8.34 (dd, 1H, J=4.9 Hz), 7.84 (s, 1H), 7.72 (td, 1H, J=6.8 Hz), 7.62 (d, 2H, J=8.6 Hz), 7.44 (d, 2H, J=8.6 Hz), 7.08 (d, 1H, J=8.4 Hz), 6.96 (td, 1H, J=5.9 Hz). M+1: 322.0. Mp: >250° C.

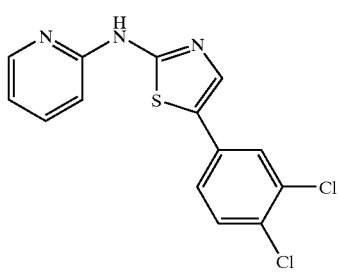

[5-(3,4-dichloro-phenyl)-thiazol-2-yl]-pyridin-2-yl-amine (5-24)

¹H NMR (CDCl₃-CD₃OD): δ8.39 (d, 1H, J=5.0 Hz), 7.62–7.67 (m, 2H), 7.56 (s, 1H), 7.43 (t, 1H, J=8.4 Hz), 7.41 (td, 1H, J=8.3 Hz), 6.93 (t, 2H, J=8.2 Hz). M+1: 322.1. Mp: >250° C.

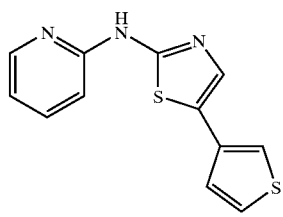

Pyridin-2-yl-(5-thiophen-3-yl-thiazol-2-yl)-amine (5-25)

¹H NMR (CDCl₃): δ8.44 (dd, 1H, J=4.2 Hz), 7.77 (td, 1H, J=7.4 Hz), 7.47 (dd, 1H, J=3.7 Hz), 7.46 (s, 1H), 7.35 (s, 1H), 7.30 (d, 1H, J=8.2 Hz), 7.27 (d, 1H, J=3.7 Hz), 7.11 (td, 1H, J=5.1 Hz). M+1: 260.0.

SCHEME 6

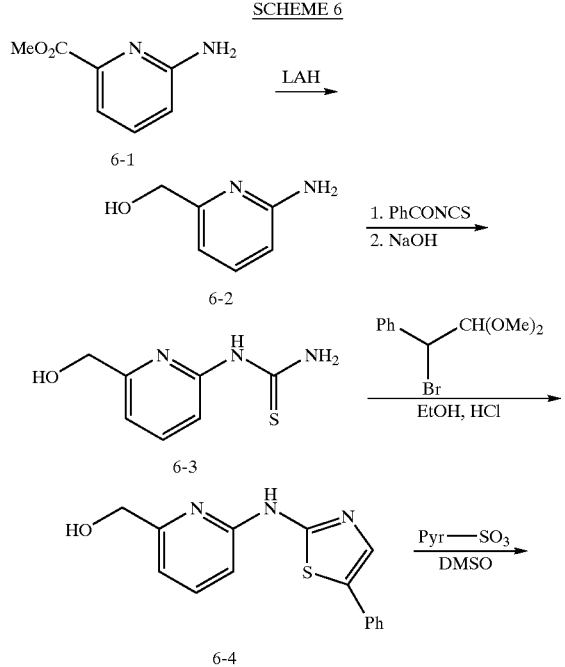

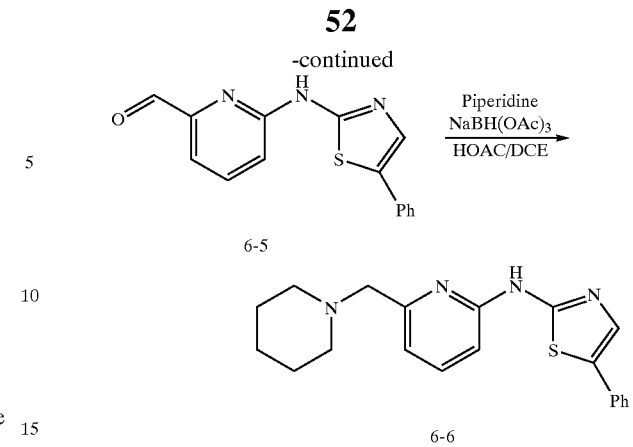

(6-Amino-pyridin-2-yl)-methanol (6-2)

6-Amino-pyridine-2-carboxylic acid methyl ester (6-1, Kelly, T. R.; Lang, F. J.Org.Chem. 1996, 61, 4623–4633) 2.37 g (15.6 mmol) was dissolved in 16 mL anhydrous THF and the resulting solution was cooled to 0° C. LAH (15.6 mL of a 1M solution) was added slowly. An additional 8 mL of THF was added during the addition of LAH to keep the mixture from becoming too viscous. After 3 h the reaction was quenched by the sequential addition of 0.59 mL water, 0.59 mL 15% NaOH (aq), and 1.77 mL water. After stirring for 1 h the mixture was filtered through a plug of celite, washing with THF. The filtrate was concentrated to afford 1.6 g of a yellow oil. Purification by flash column chromatography (eluting with a gradient of CH₂Cl₂ to 90:10 CH₂Cl₂/MeOH) afforded the titled compound as a white solid. ¹H NMR(CDCl₃): δ7.42 (t, 1H, J=7.6 Hz), 6.60 (d, 1H, J=7.7 Hz), 6.41 (d, 1H, J=7.5 Hz), 4.59 (s, 2H), 4.52 (bs, 2H).

(6-Hydroxymethyl-pyridin-2-yl)-thiourea (6-3)

(6-Amino-pyridin-2-yl)-methanol (6-2, 1.00 g, 8.06 mmol) was dissolved in 20 mL anhydrous CH₂Cl₂ and 5 mL anhydrous DMF under N₂. Benzoylisothiocyanate (1.19 mL, 8.86 mmol) was added and the reaction was stirred at room temperature fro 16 h. The reaction was concentrated in vacuo and to the resulting residue was added 24 mL 1M NaOH (aq) and 24 mL TEF. The resulting mixture was heated to reflux for 3 h. The THF was removed in vacuo and a white precipitate formed. The mixture was filtered and washed with water to provide the titled compound as a white solid. ¹H NMR(DMSO-d₆): δ10.58 (bs, 1H), 10.48 (bs, 1H), 8.84 (bs, 1H), 7.74 (t, 1H, J=8.1 Hz), 7.06 (d, 1H, J=7.5 Hz), 7.01 (d, 1H, J=8.1 Hz), 5.47 (t, 1H, J=5.9 Hz), 4.47 (d, 2H, J=5.7 Hz).

[2-(5-Phenyl-thiazol-2-ylamino)-pyridin-6-yl]-methanol (6-4)

(6-Hydroxymethyl-pyridin-2-yl)-thiourea (6-3) 1.05 g (5.73 mmol) and (1-bromo-2,2-dimethoxy-ethyl)-benzene (2.11 g, 8.60 mmol) were stirred in 18 mL EtOH. Concentrated HCl (aq), 6 mL, was added and the mixture was heated to reflux. After 7 h, additional (1-bromo-2,2-dimethoxy-ethyl)-benzene (1.05 g, 4.30 mmol) and conc HCl (aq), 3 mL were added. The reaction was then heated at reflux for an additional 14.5 h. The reaction was poured into 120 mL water and the pH was adjusted to 7 with Na₂CO₃ (s). A precipitate formed which was filtered and washed with water. The solid was triurated with 50 mL ether, filtered and washed with ether to provide the titled compound as a white solid. ¹H NMR(CD₃OD): δ7.72 (t, 1H, J=7.7 Hz), 7.58 (s overlapping with d, 3H), 7.38 (t, 2H, 7.5 Hz), 7.25 (t, 1H, J=7.3 Hz), 7.07 (d, 1H, J=7.5 Hz), 6.90 (d, 1H, J=8.3 Hz), 4.76 (s, 2H). Mp: 196–198° C. M+1: 284.0.

6-(5-Phenyl-thiazol-2-ylamino)-pyridine-2-carbaldehyde (6-5)

[2-(5-Phenyl-thiazol-2-ylamino)-pyridin-6-yl]-methanol (6-4), 0.60g (2.1 mmol) Sulfur trioxide-pyridine (1.01 g, 6.36 mmol) was dissolved in 10 mL anhydrous DMSO and the resulting solution was stirred for 10 min. Triethylamine (2.45 mL, 17.6 mmol) was added followed by addition of [2-(5-Phenyl-thiazol-2-ylamino)-pyridin-6-yl]-methanol (6-4), (0.60 g, 2.1 mmol). After 30 min the reaction was diluted with water and the resulting precipitate was filtered and washed with water to afford the titled compound.

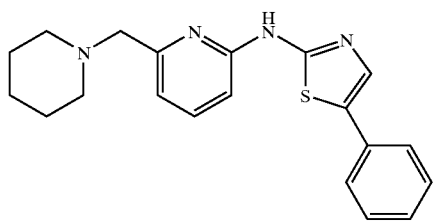

(5-Phenyl-thiazol-2-yl)-(6-piperidin-1-ylmethyl-pyridin-2-yl)-amine (6-6)

6-(5-Phenyl-thiazol-2-ylamino)-pyridine-2-carbaldehyde (6-5, 0.025 g, 0.088 mmol) was dissolved in 1 mL dichloroethane. Piperidine (0.014 mL, 0.14 mmol), acetic acid (0.010 mL) and NaBH(OAc)$_3$ (0.030 g, 0.14 mmol) were added. The reaction was stirred at room temperature for 1 h. The reaction was then diluted with CH$_2$Cl$_2$, washed with water and extracted 1× with CH$_2$Cl$_2$. The combined organic phases were dried over Na$_2$SO$_4$, filtered, concentrated. Purification by reverse phase HPLC afforded the titled compound. $^1$H NMR (CDCl$_3$): δ9.94 (bs, 1H), 7.61 (m, 4H), 7.59 (d, 2H, J=8.0 Hz), 7.41 (t, 2H, J=7.5 Hz), 7.29 (d, 1H, J=7.3 Hz), 7.06 (d, 1H, J=7.4 Hz), 6.77 (d, 1H, J=8.1 Hz), 3.73 (s, 2H), 2.56 (bs, 4H), 1.64 (m, 4H), 1.26 (m, 2H). M+1: 351.1.

The following compounds, 6-7 through 6-15, were prepared by the same method:

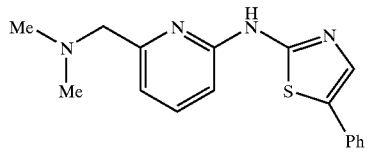

(6-Dimethylaminomethyl-pyridin-2-yl)-(5-phenyl-thiazol-2-yl)-amine (6-7)

$^1$H NMR (DMSO-d$_6$) δ11.34 (1H, s) 7.78 (1H, s), 7.69 (1H, t, J=7.8) 7.59 (2H, d, J=7.3) 7.41 (2H, t, J=7.6) 7.26 (1H, t, J=7.6) 6.96 (2H, dd, J=11.0, 7.3) 3.59 (2H,s) 2.27 (6H,s). MS [M+H]+=311.1.

| No. | Structure | Compound Name | MS [M + H]+ |
|---|---|---|---|
| 6-8 | 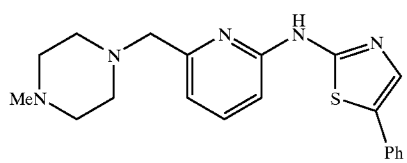 | [6-(4-Methyl-piperazin-1-ylmethyl)-pyridin-2-yl]-(5-phenyl-thiazol-2-yl)-amine | 366.1 |
| 6-9 | 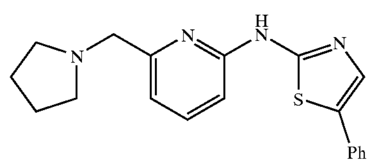 | (5-Phenyl-thiazol-2-yl)-(6-pyrrolidin-1-ylmethyl-pyridin-2-yl)-amine | 337.1 |
| 6-10 | 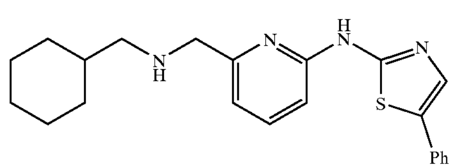 | {6-[(Cyclohexylmethyl-amino)-methyl]-pyridin-2-yl}-(5-phenyl-thiazol-2-yl)-amine | 379.1 |
| 6-11 | 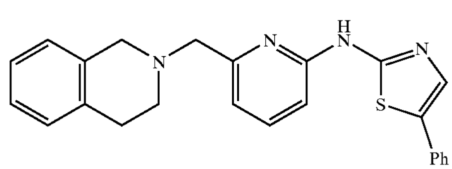 | [6-(3,4-Dihydro-1H-isoquinolin-2-ylmethyl)-pyridin-2-yl]-(5-phenyl-thiazol-2-yl)-amine | 399.2 |
| 6-12 | 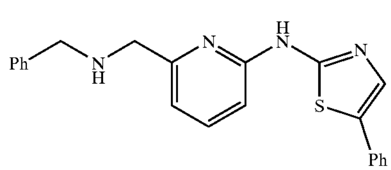 | [6-(Benzylamino-methyl)-pyridin-2-yl]-(5-phenyl-thiazol-2-yl)-amine | 373.2 |

-continued

| No. | Structure | Compound Name | MS [M + H]+ |
|---|---|---|---|
| 6-13 | 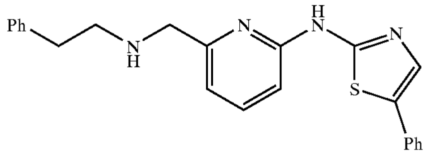 | {6-[(1-Phenyl-ethylamino)-methyl]-pyridin-2-yl}-(5-phenyl-thiazol-2-yl)-amine | 387.2 |
| 6-14 | 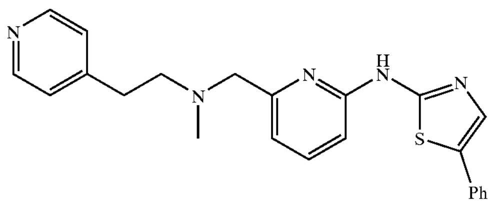 | (6-{[Methyl-(2-pyridin-4-yl-ethyl)-amino]-methyl}-pyridin-2-yl)-(5-phenyl-thiazol-2-yl)-amine | 402.2 |
| 6-15 | 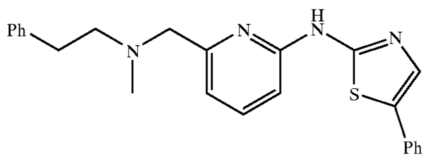 | {6-[(Methyl-phenethyl-amino)-methyl]-pyridin-2-yl}-(5-phenyl-thiazol-2-yl)-amine | 401.2 |

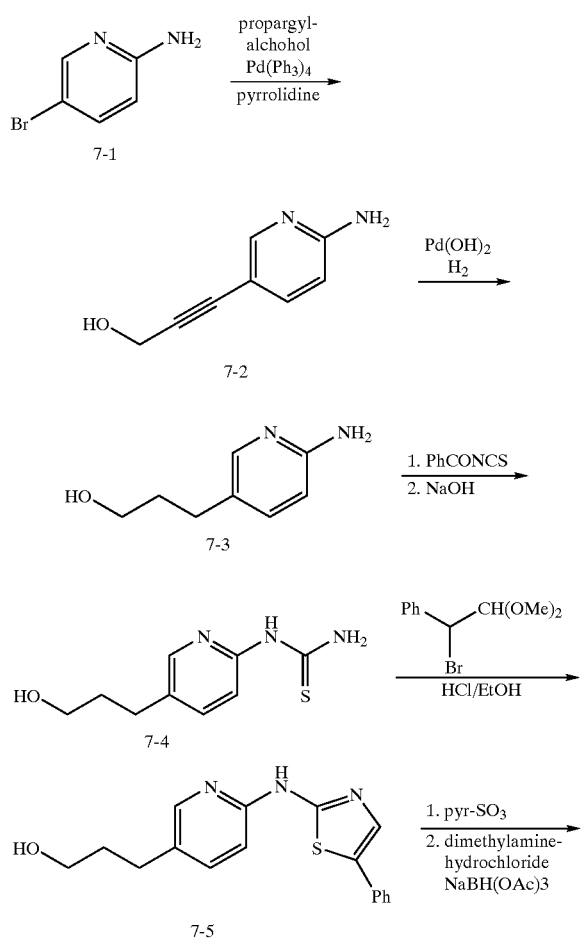

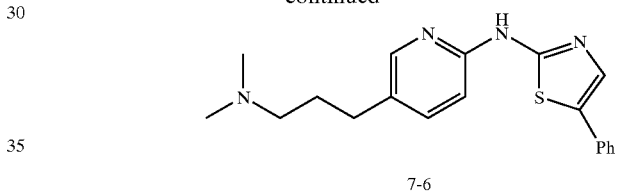

3-(6-Amino-pyridin-3-yl)-prop-2-yn-1-ol (7-2)

2-Amino5-bromopyridine (7-1), 10.0 g (57.8 mmol) was stirred in pyrrolidine (96.5 mL, 1.16 mol, 20 equiv) in a flame dried round bottom flask under argon. Propargyl alcohol (10.1 mL, 173 mmol) and tetrakis triphenylphosphine palladium(0) (1.34 g, 1.16 mmol) were added and the solution was degassed 3×by alternating vacuum/Ar. Heat to 80° C. After 18 h the bulk of the pyrrolidine was removed in vacuo and the residue was diluted with water. Extract with $CH_2Cl_2$ three times, and the extracts were dried over $Na_2SO_4$, filtered and concentrated to provide impure product. The aqueous layer was further extracted ten times with $CH_2Cl_2$/nBuOH (95:5). The extracts were dried over $Na_2SO_4$, filtered and concentrated. The two samples were combined and were purified in two batches by flash column chromatography (gradient: $CH_2Cl_2$ to $CH_2Cl_2$/MeOH, 90:10). The product was triurated with ice cold $CH_2Cl_2$, filtered, and washed with ice cold $CH_2Cl_2$. Afforded the titled compound as a pale yellow solid. $^1$H NMR (CD$_3$OD) δ7.96 (d, 1H, J=2.2 Hz), 7.45 (dd, 1H, J=2.4, 8.8 Hz), 6.51 (d, 1H, J=8.8 Hz), 4.36 (s, 2H).

3-(6-Amino-nyridin-3-yl)-propan-1-ol (7-3)

3-(6-Amino-pyridin-3-yl)-prop-2-yn-1-ol (7-2), 2.73 g (18.4 mmol) and Pd(OH)$_2$ (0.27 g) were stirred in 30 mL EtOH (aminopyridine does not completely dissolve). Reaction was put under one atmosphere of H$_2$ for 24 h. The reaction was filtered through a plug of celite, washed with EtOH, and concnetrated to afford the titled compound as an orange oil. $^1$H NMR (CDCl$_3$) δ7.90 (d, 1H, J=2.3 Hz), 7.31 (dd, 1H, J=2.4, 8.6 Hz), 6.43 (d, 1H, J=8.7 Hz), 4.38 (bs, 2H), 3.63 (t, 2H, J=7.5 Hz), 2.58 (t, 2H, J=7.2 Hz), 1.97 (bs, 1H), 1.82 (m, 2H).

[5-(3-Hydroxy-propyl)-pyridin-2-yl]-thiourea (7-4)

3-(6-Amino-pyridin-3-yl)-propan-1-ol (7-3), 2.83 g (19.5 mmol) was stirred in 15 mL of anhydrous CH$_2$Cl$_2$ under Ar. Anhydrous DMF, 5 mL was added and the solution became homogeneous. Benzoylisothiocyanate (2.62 mL, 19.5 mmol) was added and after 2 h the reaction was concentrated in vacuo. To the residue was added 60 mL 1 M NaOH, and 120 mL THF and the resulting mixture was heated to reflux. After 2 h reaction was cooled to RT, and diluted with water (pH 9). The aqueous phase was extracted three times with EtOAc. The combined organic phases was dried over Na$_2$SO$_4$, filtered and concentrated. Purification by flash column chromatography (gradient: CH$_2$Cl$_2$ to 95:5 CH$_2$Cl$_2$/MeOH) to afford the pure titled compound. $^1$H NMR (DMSO-d$_6$) δ10.57 (bs, 1H), 10.43 (bs, 1H), 8.80 (bs, 1H), 8.05 (d, 1H, J=2.3 Hz), 7.62 (dd, 1H, J=2.4, 8.6 Hz), 7.10 (d, 1H, J=8.7 Hz), 4.48 (t, 1H, J=3.0 Hz), 3.41 (m, 2H), 2.59 (t, 2H, J=6.9 Hz), 1.68 (m, 2H).

3-[6-(5-Phenyl-thiazol-2-ylamino)-pyridin-3-yl]-propan-1-ol (7-5)

[5-(3-Hydroxy-propyl)-pyridin-2-yl]-thiourea (7-4), 2.20 g (10.4 mmol) was stirred in 20 mL EtOH. (1-Bromo-2,2-dimethoxy-ethyl)-benzene (3.83 g, 15.6 mmol) was added, dissolved in 12 mL EtOH. The reaction was heated to reflux. After 30 min, 8 mL of concentrated HCl (aq) was added. After 7 h the reaction was cooled to RT, and diluted with water. Na$_2$CO$_3$ (s) was added to pH 9. The resulting precipitate was filtered, and washed with water. To solid was added ether, the mixture was sonicated and filtered, washing with ether. Afford the titled compound as a white solid. $^1$H NMR (CDCl$_3$): δ8.74 (bs, 1H), 8.25 (d, 1H, J=2.2 Hz), 7.57 (dd, 2H, J=1.7, 9.0 Hz)7.49 (dd, 1H, J=2.4, 8.4 Hz), 7.38 (t, 2H, J=7.7 Hz), 6.83 (d, 1H, J=8.2 Hz), 3.71 (m, 2H), 2.70 (t, 2H, J=6.7 Hz), 1.89 (m, 2H). Mp 153–154° C. MS [M+H]+= 312.2.

5-phenyl-thiazol-2-yl)-[5-(3-dimethylaminopropyl)-pyridin-2-yl]-amine (7-6)

3-[6-(5-Phenyl-thiazol-2-ylamino)-pyridin-3-yl]-propan-1-ol 7-5 (2.30 g, 7.39 mmol) was dissolved in 35 mL anhydrous DMSO in a flame dried flask under argon. Triethylamine (10.3 mL, 73.9 mmol) was added and the reaction cooled. Pyr-SO$_3$ (3.53 g, 22.2 mmol) was added and reaction was stirred at room temperature. After 1 h the reaction was diluted with water. The resulting precipitate was filtered to afford a yellow solid. Purification by flash column (dissolve sample in 9:1 DCM/MeOH, elute with DCM to 9:1 DCM/MeOH) afforded the methanol hemiacetal and a small amount of aldehyde. This product was used in subsequent reactions without further purification. The hemiacetal was dissolved in 2% (v/v) HOAc in DMF. Secondary amine (2 equivalents) was added followed by the addition of sodium triacetoxyboro-hydride (1.2 equivalents). After 2 h, the reaction was quenched by the addition of NaHCO$_3$ (sat aq). Extraction 3× with DCM was followed by drying the combined organic phases (Na$_2$SO$_4$), filtration and concentration. Purification of the reactions by reverse phase HPLC afforded the pure 5-phenyl-thiazol-2-yl)-[5-(3-dimethylaminopropyl)-pyridin-2-yl]-amine (7-6). $^1$H NMR (CDCl$_3$): δ10.99 (bs, 1H), 8.24 (s, 1H), 7.67 (s, 1H), 7.62 (d, 2H, J=7.6 Hz), 7.49 (dd, 1, J=1.7, 8.7 Hz), 7.40 (t, 2H, J=7.6 Hz), 6.90 (d, 1H, J=8.3 Hz), 2.62 (t, 2H, J=7.6 Hz), 2.31 (t, 2H, J=7.1 Hz), 2.23 (s, 8H), 1.79 (m, 4H). M+1: 339.1. Mp 153–154° C.

Compounds 7-7 and 7-8 below were synthesized via the protocol described above for 7-6.

{5-[3-(4-Methyl-piperazin-1-yl)-propyl]-pyridin-2-yl}-(5-phenyl-thiazol-2-yl)-amine (7-7)

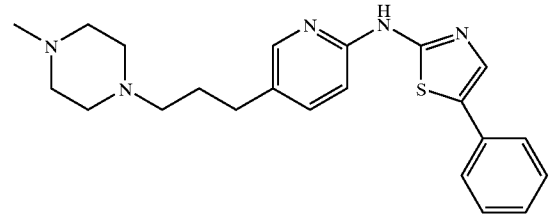

$^1$H NMR (CDCl$_3$): δ9.96 (bs, 1H), 8.23 (d, 1H, J=1.7 Hz), 7.63 (s, 1H), 7.60 (d, 2H, J=7.3 Hz), 7.47 (dd, 1, J=2.2, 8.4 Hz), 7.39 (t, 2H, J=7.6 Hz), 7.26 (m, 1H), 6.86 (d, 1H, J=8.3 Hz),2.62 (t, 2H, J=7.6 Hz), 2.40 (bs, 4H), 2.38 (t, 2H, J=7.2 Hz), 2.29 (s, 3H), 1.83 (m, 2H), 1.65 (bs, 4H). MS [M+H]+= 394.3. Mp 167–169° C.

(5-Phenyl-thiazol-2-yl)-[5-(3-piperidin-1-yl-propyl)-pyridin-2-yl]-amine (7-8)

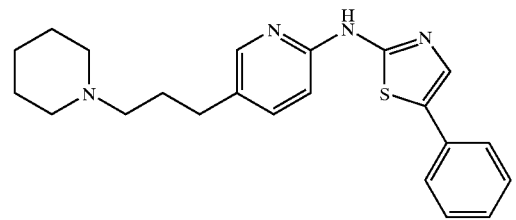

$^1$H NMR (CDCl$_3$): δ10.99 (bs, 1H), 8.24 (s, 1H), 7.67 (s, 1H), 7.62 (d, 2H, J=7.6 Hz), 7.49 (dd, 1, J=1.7, 8.7 Hz), 7.40 (t, 2H, J=7.6 Hz), 6.90 (d, 1H, J=8.3 Hz), 2.62 (t, 2H, J=7.6 Hz), 2.31 (t, 2H, J=7.1 Hz), 2.23 (s, 8H), 1.79 (m, 4H). M+1: 3339.1. Mp 153–154° C.

SCHEME 8

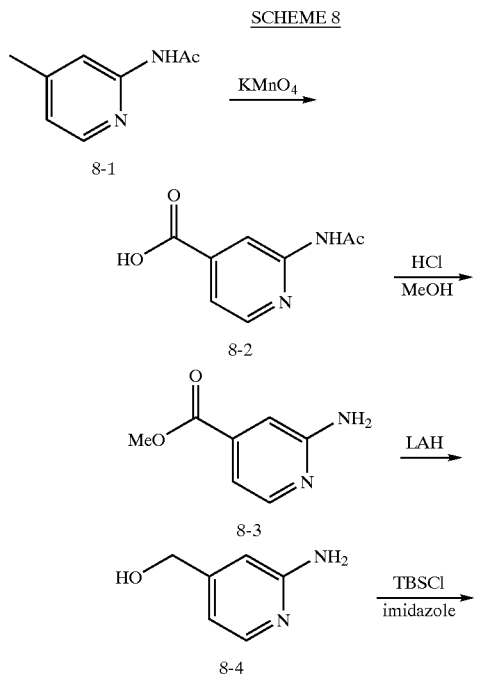

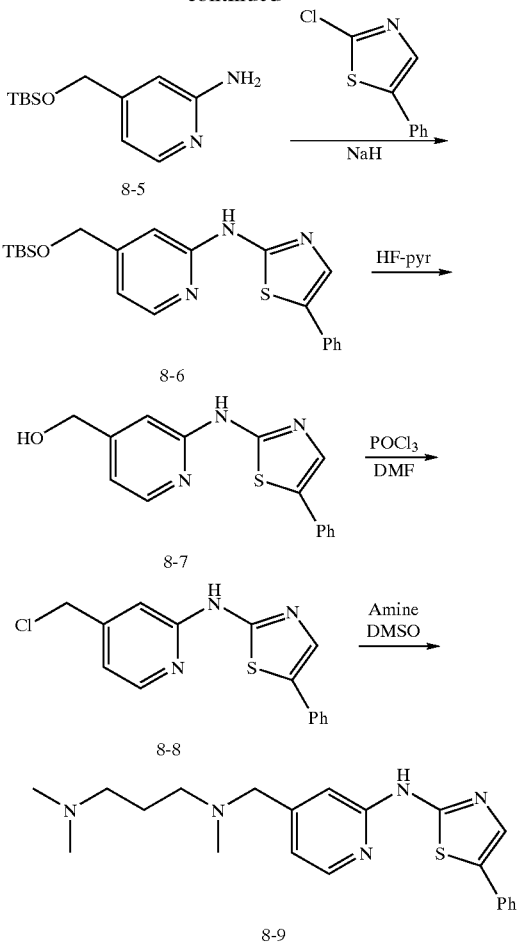

2-Acetylamino-isonicotinic acid (8-2)

N-(4-Methyl-pyridin-2-yl)-acetamide, 70 g (466 mmol) was stirred in 400 mL water. The mixture was warmed to 80° C. KMnO4 (368 g, 2330 mmol, 5 equiv) was added dissolved in water over 45 min. The solution was heated to reflux for 3 h. The reaction was cooled and filtered. The filtrate was conc in vacuo to afford the desired product. $^1$H NMR (CD$_3$OD) δ8.62 (s, 1H), 8.42 (d, 1H, J=5.1 Hz), 7.59 (dd, 1H, J=5.1 Hz), 2.19 (s, 3H).

2-Amino-isonicotinic acid methyl ester (8-3)

2-Acetylamino-isonicotinic acid (3.10 g, 17.2 mmol) was stirred in 35 mL MeOH at 0° C. HCl (g) was bubbled through the solution for 10 min and then the reaction was heated to reflux. After 16 h the reaction was concentrated in vacuo. The residue was diluted with water and the pH was adjusted to 7 with Na$_2$CO$_3$ (s). A white precipitate formed which was filtered to afford a portion of pure desired product. The aqueous phase was extracted three time with 95:5 DCM/nBuOH. The organic phases were dried over Na$_2$SO$_4$, filtered and concentrated to afford more of the pure desired product as a white solid. $^1$H NMR (CDCl$_3$) δ8.19 (d, 1H, J=5.3 Hz), 7.17 (dd, 1H, J=1.4, 5.3 Hz), 7.07 (d, 1H, J=1.3 Hz), 4.64 (bs, 2H), 3.92 (s, 3H). MS [M+H]+=153.0.

(2-Amino-pyridin-4-yl)-methanol (8-4)

2-Amino-isonicotinic acid methyl ester (6.0 g, 39.4 mmol) was dissolved in 80 mL anhydrous THF in a flame dried round bottom flask under nitrogen gas. The solution was cooled to −45° C. and LAH (39.4 mL, 1M in THF) was added slowly. The reaction was allowed to warm to 0° C. and was quenched by the addition of 15 mL of 1M NaOH (aq). The solution was filtered and the solid was washed with THF. The filtrate was concentrated to afford the pure product. $^1$H NMR (DMSO-d$_6$) δ7.79 (d, 1H, J=5.2 Hz), 6.41 (s, 1H), 6.38 (d, 1H, J=5.9 Hz), 5.79 (bs, 2H), 5.19 (t, 2H, J=5.7), 4.35 (d, 2H, J=5.6 Hz).

4-(tert-Butyl-dimethyl-silanyloxymethyl)-pyridin-2-ylamine (8-5)

(2-Amino-pyridin-4-yl)-methanol (4.68 g, 37.7 mmol) was dissolved in 40 mL anhydrous DMF under N$_2$. Imidazole (2.57 g, 37.7 mmol, 1 equiv) was added followed by the addition of TBSCl (5.68 g, 37.7 mmol, 1 equiv). After 2 h the reaction was quenched by the addition of water. A precipitate formed which was filtered to afford pure desired product. The aqueous filtrate was extract 3× with EtOAc. The organic phases were dried over Na$_2$SO$_4$, filtered and concentrated to afford additional impure material. $^1$H NMR (CDCl$_3$) δ7.99 (d, 1H, J=5.8 Hz), 6.57 (d, 1H, J=5.1 Hz), 6.51 (s, 1H), 4.64 (s, 2H), 4.40 (bs, 2H), 0.95 (s, 9H), 0.11 (s, 6H).

[4-(tert-Butyl-dimethyl-silanyloxymethyl)-pyridin-2-yl]-(5-phenyl-thiazol-2-yl)-amine (8-6)

4-(tert-Butyl-dimethyl-silanyloxymethyl)-pyridin-2-ylamine (8-5), 1.00 g (4.19 mmol) was dissolved in 20 mL anhydrous THF at room temp, and NaH (60% dispersion, 0.670 g, 16.8 mmol) was added. When the bubbling stopped, 2-chloro-5-phenyl-thiazole (Hafez, E. A. A.; Abed, N. M.; Elsakka, I. A.; J.Heterocycl.Chem. 1983; 20, 285–288), 0.739 g (3.78 mmol) was added, and the reaction was heated to reflux. After 2 hours the THF was removed in vacuo and the resulting solution was taken to neutral pH with 1M HCl (aq) and filtered. The residue was purified by flash column chromatography using 20% EtOAc in hexane. $^1$H NMR (CDCl$_3$): δ9.09 (bs, 1H), 8.32 (d, 1H, J=5.2 Hz), 7.62 (s, 1H), 7.56 (d, 2H, J=7.4 Hz), 7.38 (t, 2H, J=7.6 Hz), 7.26 (overlapping with CHCl$_3$, 1H), 6.90 (s, 1H), 6.82 (d, 1H, J=5.2 Hz), 4.75 (s, 2H), 0.96 (s, 9H), 0.14 (s, 6H). mp 207° C.

[2-(5-Phenyl-thiazol-2-ylamino)-pyridin-4-yl]-methanol (8-7)

[4-(tert-Butyl-dimethyl-silanyloxymethyl)-pyridin-2-yl]-(5-phenyl-thiazol-2-yl)-amine (8-6), 0.805 g (2.03 mmol) was dissolved in 10 mL THF and the resulting solution was cooled to 0° C. Hydrogen fluoride-pyridine (Aldrich, HF ~70%, pyridine ~30%) 1.20 mL was added. After 1 h the reaction was allowed to arm to RT. The THF was removed in vacuo and the residue was diluted with sat Na$_2$CO$_3$ (aq). The resulting precipitate was filtered to provide the pure title compound. $^1$H NMR (DMSO-d$_6$): δ11.35 (bs, 1H), 8.25 (d, 1H, J=5.2 Hz), 7.79 (s, 1H), 7.59 (d, 2H, J=7.4 Hz), 7.39 (t, 2H, J=7.6 Hz), 7.25 (t, 1H, J=7.3 Hz), 7.08 (s, 1H), 6.86 (d, 1H, J=5.2 Hz), 5.42 (bs, 1H), 4.51 (s, 2H). Mp 236–237° C. M+1: 284.0.

(4-Chloromethyl-pyridin-2-yl)-(5-phenyl-thiazol-2-yl)-amine (8-8)

[2-(5-Phenyl-thiazol-2-ylamino)-pyridin-4-yl]-methanol 8-7 (0.500 g, 1.77 mmol) was stirred in anh CH$_2$Cl$_2$ (5 mL) under N$_2$. N,N-Dimethylformamide (0.137 mL, 1.76 mmol, 1 equiv) was added followed by the addition of phosphorous oxychloride (0.165 mL, 1.76 mmol). After 1.5 h the reaction was concentrated and quenched by the addition of saturated NaHCO$_3$ (aq). A precipitate formed which was filtered and washed with water to provide the titled compound. $^1$H NMR (DMSO-d$_6$) δ11.49 (bs, 1H), 8.34 (d, 1H, J=5.2 Hz), 7.81 (s, 1H), 7.60 (d, 2H, J=7.7 Hz), 7.39 (t, 2H, J=7.6 Hz), 7.26 (t, 1H, 7.0 Hz), 7.13 (s, 1H), 6.99 (d, 1H, J=5.3 Hz), 4.77 (s, 2H).

N,N,N'-Trimethyl-N'-[2-(5-phenyl-thiazol-2-ylamino)-pyridin-4-ylmethyl]-propane-1,3-diamine (8-9)

(4-Chloromethyl-pyridin-2-yl)-(5-phenyl-thiazol-2-yl)-amine 8-8 (0.050 g, 0.166 mmol) was dissolved in 0.50 mL DMSO. N,N,N'-trimethyl-1,3-propanediamine was added and the reaction was stirred at RT. After 1 h a copious amount precipitate had formed. Saturated NaHCO₃ (aq) was added and the resulting precipitate was filtered and washed with water to afford pure compound 8-9. ¹H NMR (CDCl₃) δ9.16 (bs, 1H), 8.31 (d, 1H, J=5.1 Hz), 7.63 (s, 1H), 7.59 (d, 2H, J=7.4 Hz), 7.38 (t, 2H, J=7.6 Hz), 7.26 (overlapping with CHCl₃), 6.91 (s, 1H), 6.88 (d, 1H, J=5.1 Hz), 3.49 (s, 2H), 2.43 (t, 2H, J=7.4 Hz), 2.30 (t, 2H, J=7.5 Hz), 2.34 (s, 3H), 2.21 (s, 6H), 1.68 (overlapping with water). MS [M+H]+382.3. mp 190–193.

The following examples, 8-10 through 8-50, were prepared in the same manner:

[4-(4-Methanesulfonyl-piperazin-1-ylmethyl)-pyridin-2-yl]-(5-phenyl-thiazol-2-yl)-amine (8-10)

TFA salt: ¹H NMR (CD₃OD) δ8.51 (d, 1H, J=5.5 Hz), 7.79 (s, 1H), 7.63 (d, 2H, J=7.8 Hz), 7.45 (t, 2H, J=7.3 Hz), 7.36 (t, 1H, 7.6 Hz), 7.32 (s, 1H), 7.25 (d, 1H, J=5.5 Hz), 4.31 (s, 2H), 3.50 (s, 4H), 3.30 (overlapping with MeOH), 2.95 (s, 3H). mp 183–184° C.

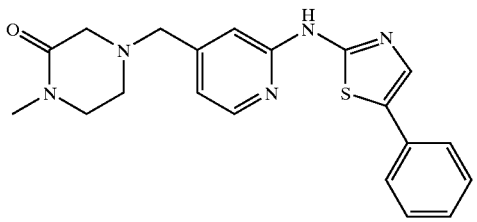

1-Methyl4-[2-(5-phenyl-thiazol-2-ylamino)-pyridin-4-ylmethyl]-piperazin-2-one (8-11)

TFA salt: ¹H NMR (CDCl₃) δ8.43 (d, 1H, J=5.2 Hz), 7.55 (d, 2H, J=6.8 Hz), 7.50–7.41 (m, 4H), 7.25 (s, 1H), 7.19 (d, 1H, J=5.3 Hz), 3.81 (s, 2H), 3.48 (t, 2H, 5.2 Hz), 3.37 (s, 2H), 2.94 (t, 2H, J=5.6 Hz), 2.72 (s, 3H). MS [M+H]+= 380.3.

| No. | Structure | Name | MS [M + H]+ |
|---|---|---|---|
| 8-12 | 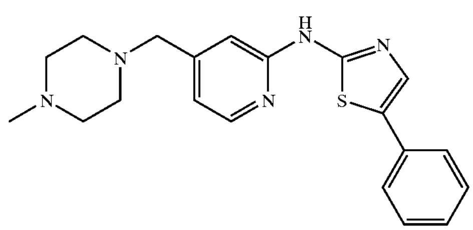 | [4-(4-Methyl-piperazin-1-ylmethyl)-pyridin-2-yl]-(5-phenyl-thiazol-2-yl)-amine | 366.2 |
| 8-13 | 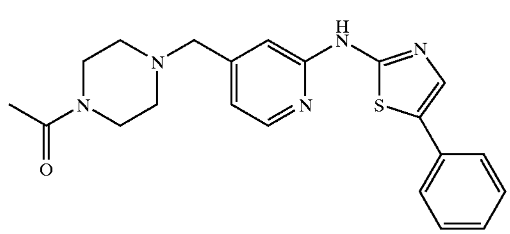 | 1-{4-[2-(5-Phenyl-thiazol-2-ylamino)-pyridin-4-ylmethyl]-piperazin-1-yl}-ethanone | 394.1697 |
| 8-14 | 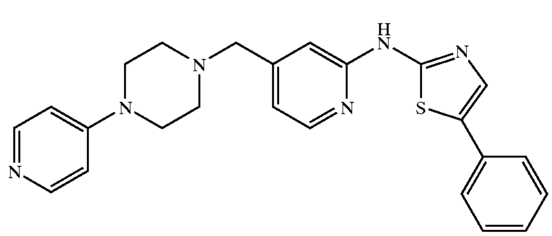 | (5-Phenyl-thiazol-2-yl)-[4-(4-pyridin-4-yl-piperazin-1-ylmethyl)-pyridin-2-yl]-amine | 429.1886 |

-continued

| No. | Structure | Name | MS [M + H]+ |
|---|---|---|---|
| 8-15 | 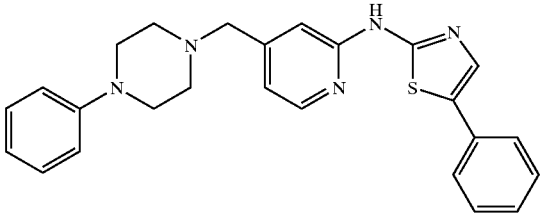 | [4-(4-Phenyl-piperazin-1-ylmethyl)-pyridin-2-yl]-(5-phenyl-thiazol-2-yl)-amine | 428.1931 |
| 8-16 | 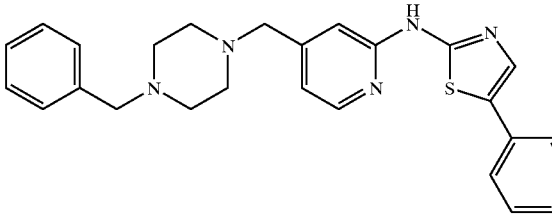 | [4-(4-Benzyl-piperazin-1-ylmethyl)-pyridin-2-yl]-(5-phenyl-thiazol-2-yl)-amine | 442.2104 |
| 8-17 | 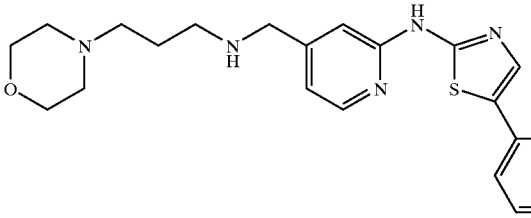 | {4-[(3-Morpholin-4-yl-propylamino)-methyl]-pyridin-2-yl}-(5-phenyl-thiazol-2-yl)-amine | 410.2013 |
| 8-18 | 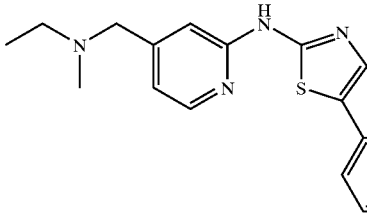 | {4-[(Ethyl-methyl-amino)-methyl]-pyridin-2-yl}-(5-phenyl-thiazol-2-yl)-amine | 325.1495 |
| 8-19 | 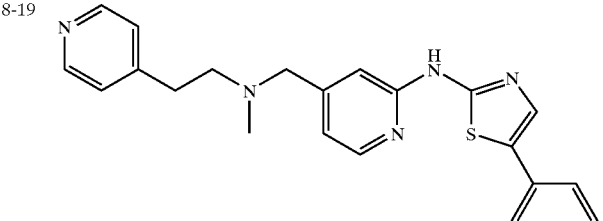 | (4-{[Methyl-(2-pyridin-4-yl-ethyl)-amino]-methyl}-pyridin-2-yl)-(5-phenyl-thiazol-2-yl)-amine | 402.2 |
| 8-20 | 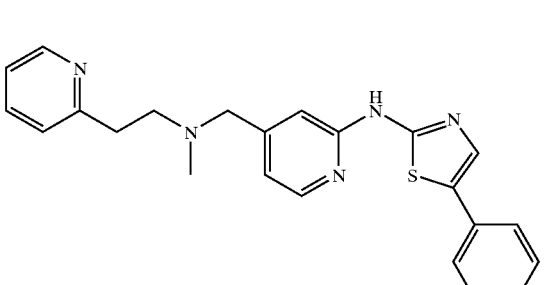 | (4-{[Methyl-(2-pyridin-2-yl-ethyl)-amino]-methyl}-pyridin-2-yl)-(5-phenyl-thiazol-2-yl)-amine | 402.1762 |

-continued

| No. | Structure | Name | MS [M + H]+ |
|---|---|---|---|
| 8-21 | 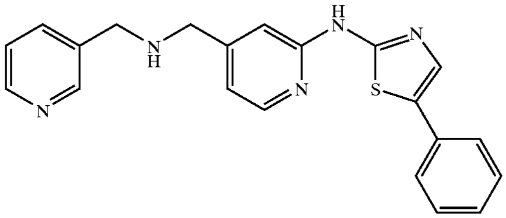 | (5-Phenyl-thiazol-2-yl)-(4-{[(pyridin-3-ylmethyl)-amino]-methyl}-pyridin-2-yl)-amine | 374.1430 |
| 8-22 | 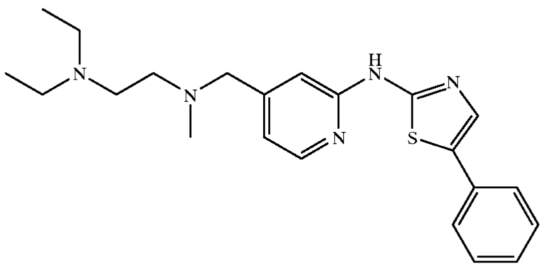 | N,N-Diethyl-N'-methyl-N'-[2-(5-phenyl-thiazol-2-ylamino)-pyridin-4-ylmethyl]-ethane-1,2-diamine | 396.2252 |
| 8-23 | 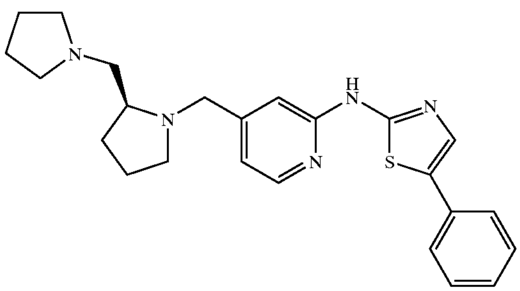 | (5-Phenyl-thiazol-2-yl)-[4-(2-pyrrolidin-1-ylmethyl-pyrrolidin-1-ylmethyl)-pyridin-2-yl]-amine | 420.2263 |
| 8-24 | 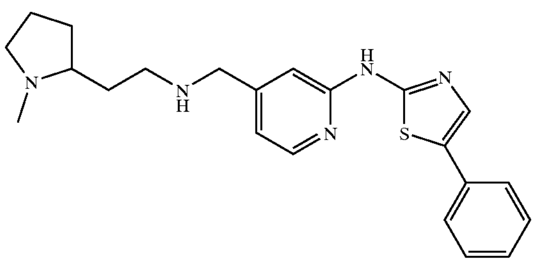 | (4-{[2-(1-Methyl-pyrrolidin-2-yl)-ethylamino]-methyl}-pyridin-2-yl)-(5-phenyl-thiazol-2-yl)-amine | 394.2083 |
| 8-25 | 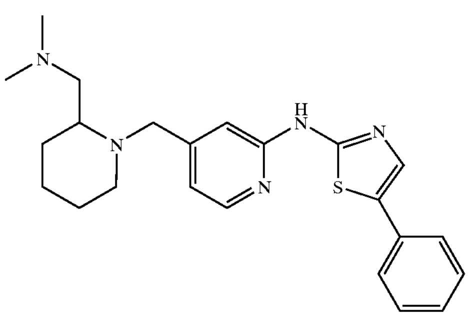 | [4-(2-Dimethylaminomethyl-piperidin-1-ylmethyl)-pyridin-2-yl]-(5-phenyl-thiazol-2-yl)-amine | 408.2255 |

-continued

| No. | Structure | Name | MS [M + H]+ |
|---|---|---|---|
| 8-26 | 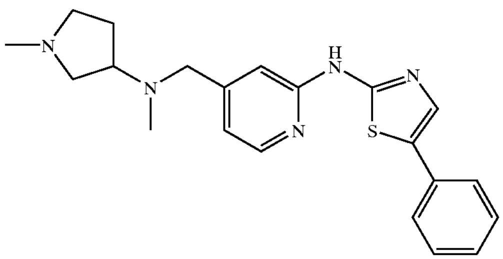 | (4-{[Methyl-(1-methyl-pyrrolidin-3-yl)-amino]-methyl}-pyridin-2-yl)-(5-phenyl-thiazol-2-yl)-amine | 380.1930 |
| 8-27 | 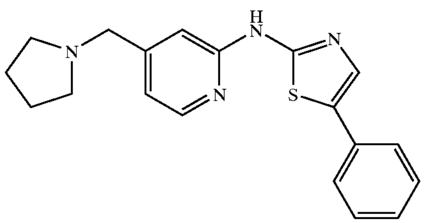 | (5-Phenyl-thiazol-2-yl)-(4-pyrrolidin-1-ylmethyl-pyridin-2-yl)-amine | 337.1511 |
| 8-28 | 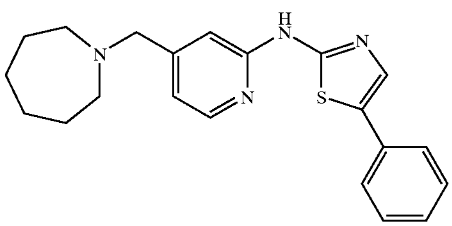 | (4-Azepan-1-ylmethyl-pyridin-2-yl)-(5-phenyl-thiazol-2-yl)-amine | 365.1783 |
| 8-29 | 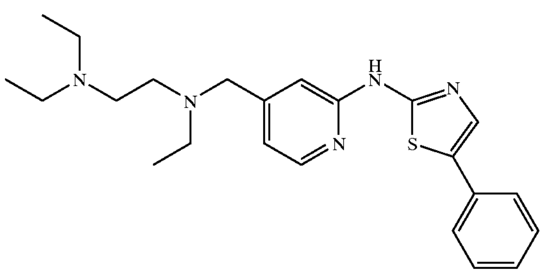 | N,N,N'-Triethyl-N'-[2-(5-phenyl-thiazol-2-ylamino)-pyridin-4-ylmethyl]-ethane-1,2-diamine | 410.2401 |
| 8-30 | 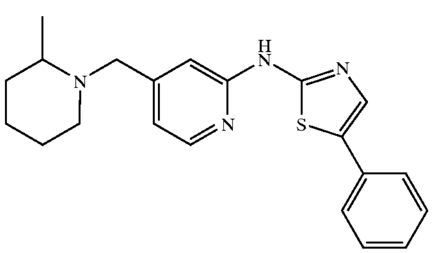 | [4-(2-Methyl-piperidin-1-ylmethyl)-pyridin-2-yl]-(5-phenyl-thiazol-2-yl)-amine | 365.1883 |
| 8-31 | 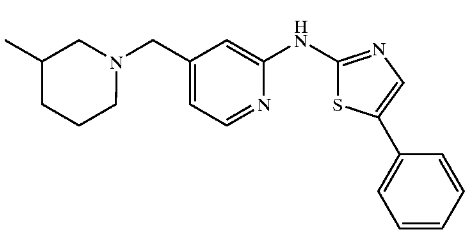 | [4-(3-Methyl-piperidin-1-ylmethyl)-pyridin-2-yl]-(5-phenyl-thiazol-2-yl)-amine | 365.1829 |

-continued

| No. | Structure | Name | MS [M + H]+ |
|---|---|---|---|
| 8-32 | 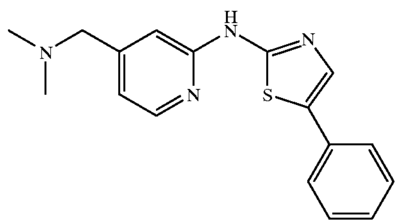 | (4-Dimethylaminomethyl-pyridin-2-yl)-(5-phenyl-thiazol-2-yl)-amine | 311.3 |
| 8-33 | 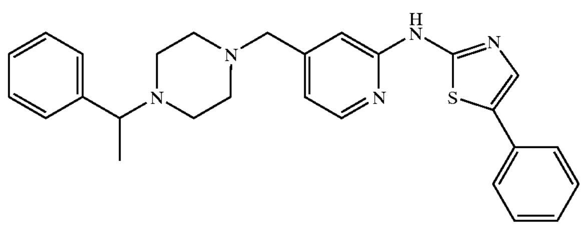 | {4-[4-(1-Phenyl-ethyl)-piperazin-1-ylmethyl]-pyridin-2-yl}-(5-phenyl-thiazol-2-yl)-amine | 456.2265 |
| 8-34 | 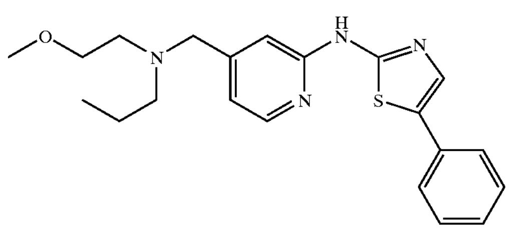 | (4-{[(2-Methoxy-ethyl)-propyl-amino]-methyl}-pyridin-2-yl)-(5-phenyl-thiazol-2-yl)-amine | 383.1939 |
| 8-35 | 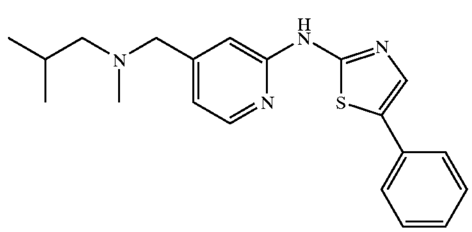 | {4-[(Isobutyl-methyl-amino)-methyl]-pyridin-2-yl}-(5-phenyl-thiazol-2-yl)-amine | 353.1822 |
| 8-36 | 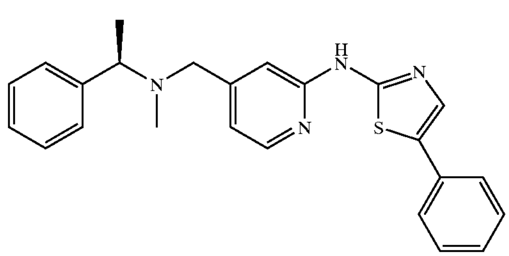 | (4-{[Methyl-(1-phenyl-ethyl)-amino]-methyl}-pyridin-2-yl)-(5-phenyl-thiazol-2-yl)-amine | 401.1830 |
| 8-37 | 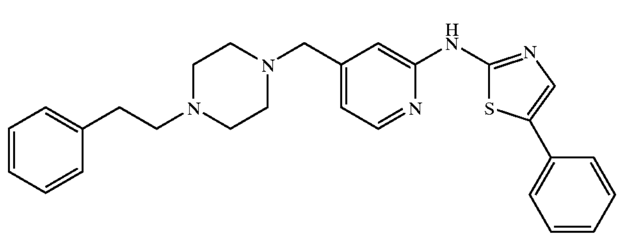 | [4-(4-Phenethyl-piperazin-1-ylmethyl)-pyridin-2-yl]-(5-phenyl-thiazol-2-yl)-amine | 456.2240 |

-continued

| No. | Structure | Name | MS [M + H]+ |
|---|---|---|---|
| 8-38 | 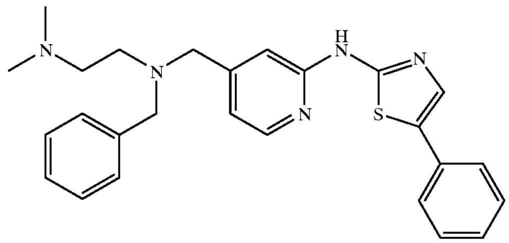 | N-Benzyl-N',N'-dimethyl-N-[2-(5-phenyl-thiazol-2-ylamino)-pyridin-4-ylmethyl]-ethane-1,2-diamine | 444.2241 |
| 8-39 | 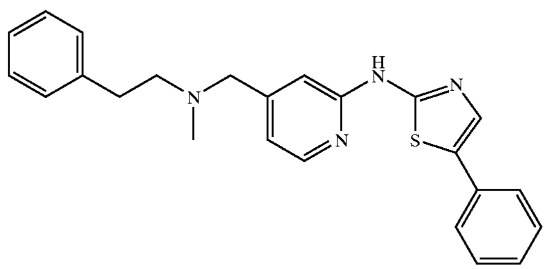 | {4-[(Methyl-phenethyl-amino)-methyl]-pyridin-2-yl}-(5-phenyl-thiazol-2-yl)-amine | 401.1829 |
| 8-40 | 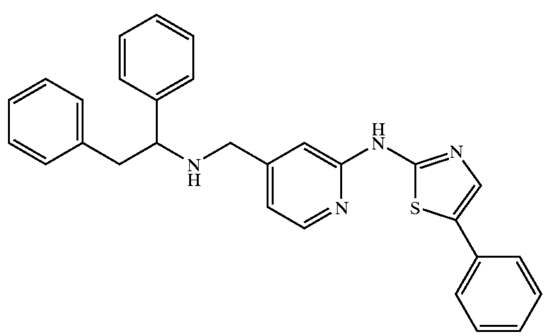 | {4-[(1,2-Diphenyl-ethylamino)-methyl]-pyridin-2-yl}-(5-phenyl-thiazol-2-yl)-amine | 463.2016 |
| 8-41 | 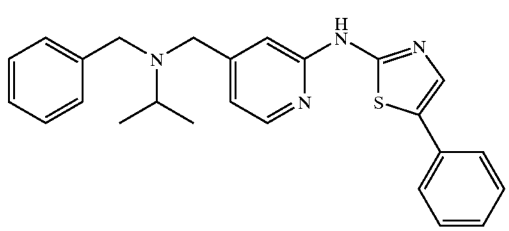 | {4-[(Benzyl-isopropyl-amino)-methyl]-pyridin-2-yl}-(5-phenyl-thiazol-2-yl)-amine | 415.1942 |
| 8-42 | 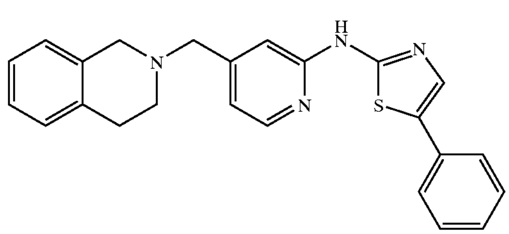 | [4-(3,4-Dihydro-1H-isoquinolin-2-ylmethyl)-pyridin-2-yl]-(5-phenyl-thiazol-2-yl)-amine | 399.2 |

-continued

| No. | Structure | Name | MS [M + H]+ |
|---|---|---|---|
| 8-43 | 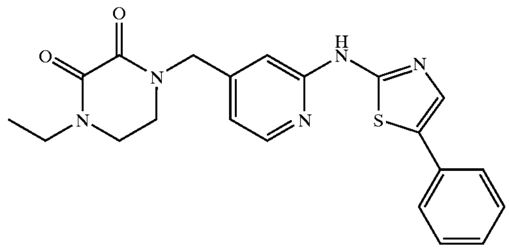 | 1-Ethyl-4-[2-(5-phenyl-thiazol-2-ylamino)-pyridin-4-ylmethyl]-piperazine-2,3-dione | 408.2 |
| 8-44 | 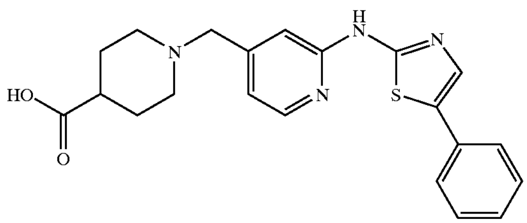 | 1-[2-(5-Phenyl-thiazol-2-ylamino)-pyridin-4-ylmethyl]-piperazine-4-carboxylic acid | 395.0 |
| 8-45 | 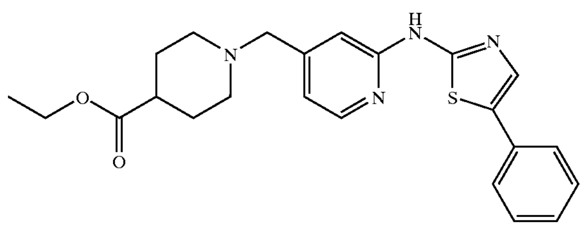 | 1-[2-(5-Phenyl-thiazol-2-ylamino)-pyridin-4-ylmethyl]-piperidine-4-carboxylic acid ethyl ester | 423.1 |
| 8-46 | 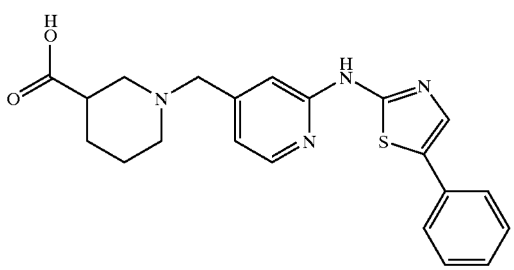 | 1-[2-(5-Phenyl-thiazol-2-ylamino)-pyridin-4-ylmethyl]-piperdine-3-carboxylic acid | 395.3 |
| 8-47 | 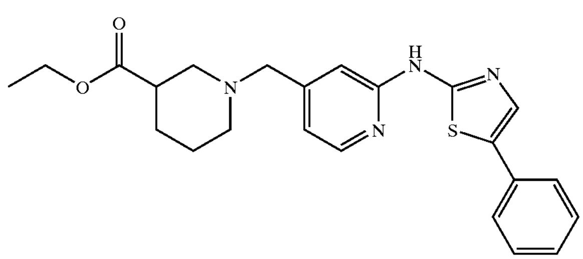 | 1-[2-(5-Phenyl-thiazol-2-ylamino)-pyridin-4-ylmethyl]-piperidine-3-carboxylic acid ethyl ester | 423.2 |
| 8-48 | 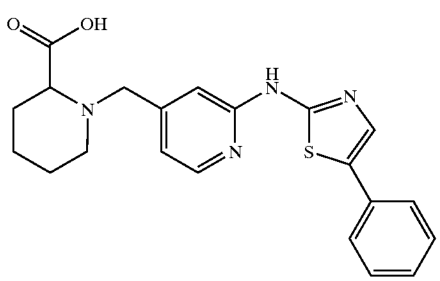 | 1-[2-(5-Phenyl-thiazol-2-ylamino)-pyridin-4-ylmethyl]-piperidine-2-carboxylic acid | 395.2 |

-continued

| No. | Structure | Name | MS [M + H]+ |
|---|---|---|---|
| 8-49 | 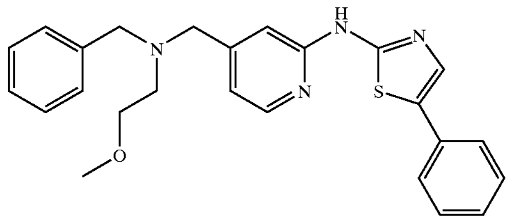 | (4-{[Benzyl-(2-methoxy-ethyl)-amino]-methyl}-pyridin-2-yl)-(5-phenyl-thiazol-2-yl)-amine | 431.2 |
| 8-50 | 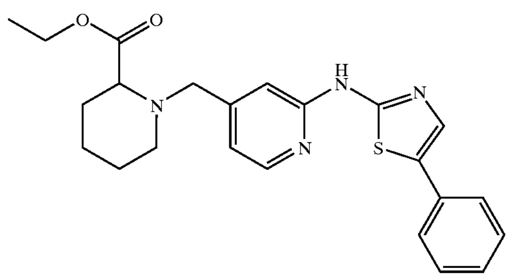 | 1-[2-(5-Phenyl-thiazol-2-ylamino)-pyridin-4-ylmethyl]-piperidine-2-carboxylic acid ethyl ester | 423.3 |

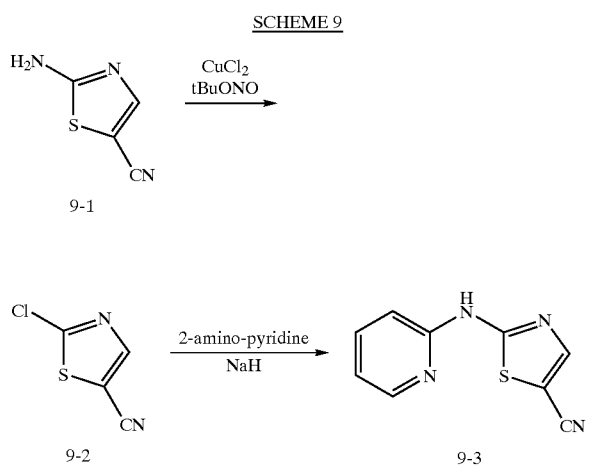

SCHEME 9

2-Chloro-thiazole-5-carbonitrile (9-2)

A flame dried round bottom flask under $N_2$ was charged with 150 mL anhydrous MeCN. $CuCl_2$ (12.9 g, 95.9 mmol, 1.2 equiv) was added and the reaction was maintained in a room temperature bath. tert-Butylnitrite (14.3 mL, 120 mmol, 1.5 equiv) was added gradually over 10 min. After 10 min, 2-amino-thiazole-5-carbonitrile (9-1, 10.0 g, 79.9 mmol ) was added as a solid gradually. The reaction was stirred at room temp for 4 h. The reaction was poured into 400 mL 0.5M HCl (aq). The mixture was extracted 3× with EtOAc. The organic phases were dried over $Na_2SO_4$, filtered and concentrated to afford pure desired product. $^1$H NMR ($CDCl_3$) δ8.04 (s).

2-(Pyridin-2-ylamino)-thiazole-5-carbonitrile (9-3)

A flame dried round-bottom flask under Ar was charged with NaH (60% dispersion 0.037 g, 0.91 mmol). Anhydrous THF, 2 mL, was added followed by the addition of 2-aminopyridine (0.032 g, 0.033 mmol). 2-Chloro-thiazole-5-carbonitrile (9-2, 0.044 g, 0.30 mmol) was added and the reaction was heated to reflux. After 2 h the reaction was cooled and quenched by the addition of water. The THF was removed in vacuo and the precipitate which formed was filtered and washed with water. The solid was recrystallized from DMSO to provide a pure sample of the desired product. $^1$H NMR (DMSO-$d_6$) d 12.23 (s, 1H), 8.40 (m, 1H), 8.27 (s, 1h), 7.82 (m, 1H), 7.15 (d, 1H, J=8.3 Hz), 7.08 (m, 1H). MS [M+H]+=203.0.

Compounds 9-4 through 9-20 below were prepared in a similar manner:

| No. | Structure | Name | MS |
|---|---|---|---|
| 9-4 | 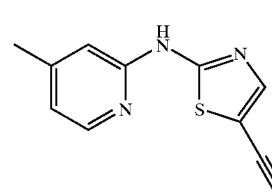 | 2-(4-Methyl-pyridin-2-ylamino)-thiazole-5-carbonitrile | [M]+ 216.0474 |

-continued

| No. | Structure | Name | MS |
|---|---|---|---|
| 9-5 | 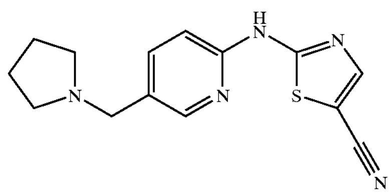 | 2-(5-Pyrrolidin-1-ylmethyl-pyridin-2-ylamino)-thiazole-5-carbonitrile | [M + H]+ 286.1 |
| 9-6 | 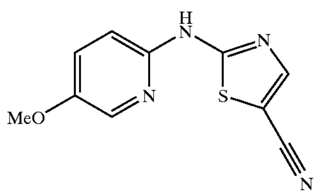 | 2-(5-Methoxy-pyridin-2-ylamino)-thiazole-5-carbonitrile | [M]+ 232.0427 |
| 9-7 | 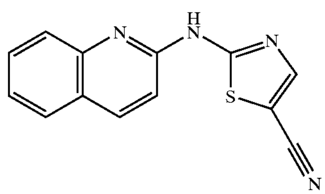 | 2-(Quinolin-2-ylamino)-thiazole-5-carbonitrile | [M]+ 252.0473 |
| 9-8 | 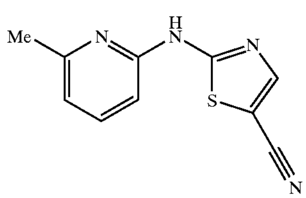 | 2-(6-Methyl-pyridin-2-ylamino)-thiazole-5-carbonitrile | [M]+ 216.0470 |
| 9-9 | 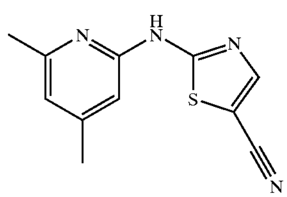 | 2-(4,6-Dimethyl-pyridin-2-ylamino)-thiazole-5-carbonitrile | [M]+ 230.0621 |
| 9-10 | 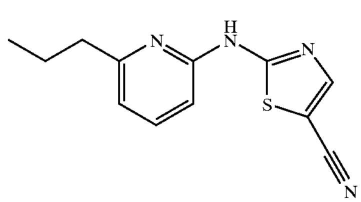 | 2-(6-Propyl-pyridin-2-ylamino)-thiazole-5-carbonitrile | [M]+ 244.0783 |
| 9-11 | 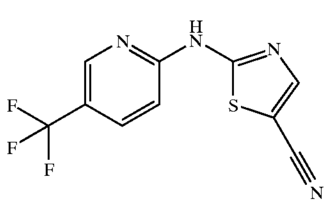 | 2-(5-Trifluoromethyl-pyridin-2-ylamino)-thiazole-5-carbonitrile | [M]+ 270.0174 |

-continued

| No. | Structure | Name | MS |
|---|---|---|---|
| 9-12 | 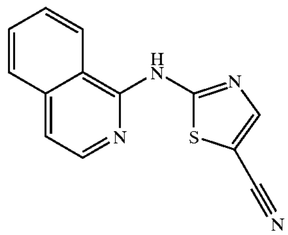 | 2-(Isoquinolin-1-ylamino)-thiazole-5-carbonitrile | [M]+ 252.0469 |
| 9-13 | 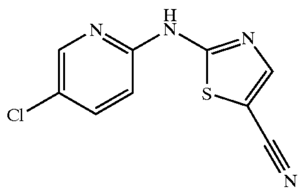 | 2-(5-Chloro-pyridin-2-ylamino)-thiazole-5-carbonitrile | [M]+ 235.9918 |
| 9-14 | 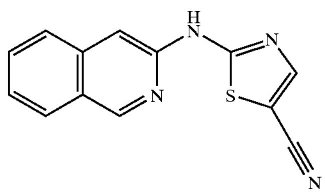 | 2-(Isoquinolin-3-ylamino)-thiazole-5-carbonitrile | [M]+ 252.0467 |
| 9-15 | 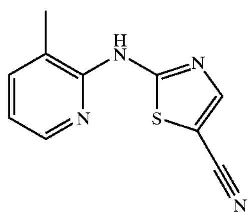 | 2-(3-Methyl-pyridin-2-ylamino)-thiazole-5-carbonitrile | [M]+ 216.0470 |
| 9-16 | 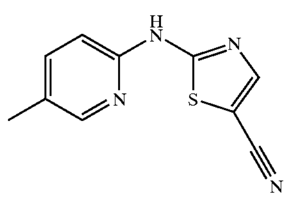 | 2-(5-Methyl-pyridin-2-ylamino)-thiazole-5-carbonitrile | [M]+ 216.0470 |
| 9-17 | 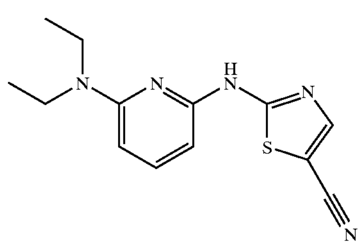 | 2-(6-Diethylamino-pyridin-2-ylamino)-thiazole-5-carbonitrile | [M + H]+ 274.1 |
| 9-18 | 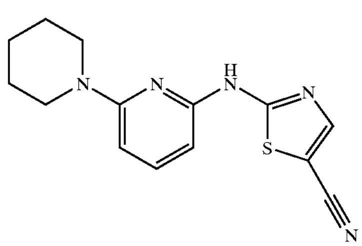 | 2-(3,4,5,6-Tetrahydro-2H-[1,2']bipyridinyl-6'-ylamino)-thiazole-5-carbonitrile | [M + H]+ 286.0 |

| No. | Structure | Name | MS |
|---|---|---|---|
| 9-19 | 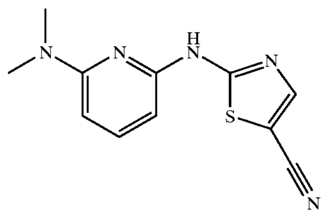 | 2-(6-Dimethylamino-pyridin-2-ylamino)-thiazole-5-carbonitrile | [M + H]+ 246.1 |
| 9-20 | 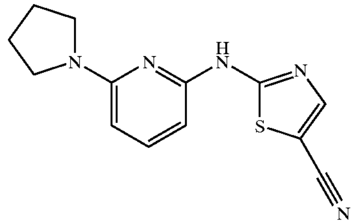 | 2-(6-Pyrrolidin-1-yl-pyridin-2-ylamino)-thiazole-5-carbonitrile | [M + H]+ 272.1 |

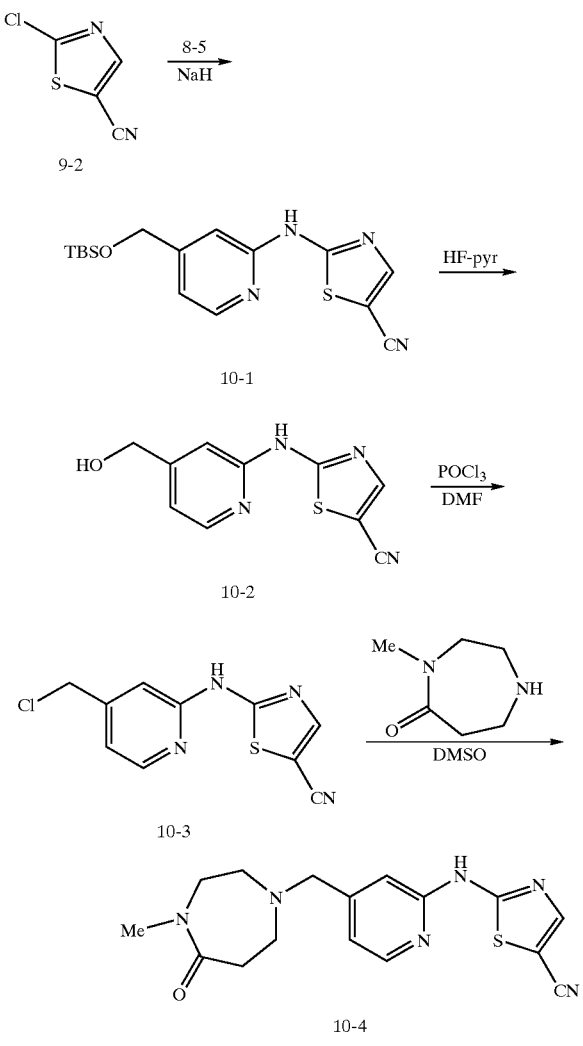

SCHEME 10

2-[4-(tert-Butyl-dimethyl-silanyloxymethyl)-pyridin-2-ylamino]-thiazole-5-carbonitrile (10-1)

4-(tert-Butyl-dimethyl-silanyloxymethyl)-pyridin-2-ylamine (8-5, 5.94 g, 24.9 mmol) was dissolved in 50 mL anhydrous THF under $N_2$. NaH (60% suspension, 2.99 g, 74.8 mmol, 3 equiv) was added (vigorous bubbling occurs) and the resulting mixture was stirred for 15 min. 2-Chloro-thiazole-5-carbonitrile (4.32 g, 29.9 mmol) was added and the reaction was heated to reflux. After 2 h the reaction was cooled and was quenched by the addition of water. The THF was removed in vacuo and the resulting aqueous solution was adjusted to pH=7 by the addition of 1M HCl (aq). The resulting precipitate was filtered and washed with water to provide reasonably pure desired product. $^1$H NMR (CDCl$_3$) δ10.32 (bs, 1H), 8.33 (d, 1H, J=5.3 Hz), 7.99 (s, 1H), 6.96 (s, 1H), 6.91 (d, 1H, J=5.3 Hz), 4.78 (s, 2H), 0.98 (s, 9H), 0.16 (s, 6H)

2-(4-Hydroxymethyl-pyridin-2-ylamino)-thiazole-5-carbonitrile (10-2)

2-[4-(tert-Butyl-dimethyl-silanyloxymethyl)-pyridin-2-ylamino]-thiazole-5-carbonitrile (1.30 g, 3.75 mmol) was dissolved in 10 mL anh THF. Hydrogen-fluoride (Aldrich, 5.0 mL) was added and the reaction was stirred for 20 min. The bulk of the solvent was removed in vacuo and the resulting residue was diluted with half-saturated NaHCO$_3$ (aq). A precipitate formed which was filtered and washed with water to afford the titled compound. $^1$H NMR (DMSO-d$_6$) δ12.23 (bs, 1H), 8.30 (d, 1H, J=5.3 Hz), 8.26 (s, 1H), 7.15 (s, 1H), 6.99 (d, 1H, J=5.3 Hz), 5.49 (t, 1H, J=5.7 Hz) 4.54 (d, 2H, J=5.7 Hz).

2-(4-Chloromethyl-pyridin-2-ylamino)-thiazole-5-carbonitrile (10-3)

2-(4-Hydroxymethyl-pyridin-2-ylamino)-thiazole-5-carbonitrile (0.883 g, 3.80 mmol) was stirred in anh CH$_2$Cl$_2$ (12 mL) under N$_2$. Dimethylformamide (0.354 mL, 3.80 mmol, 1 equiv) was added followed by the addition of phosphorous oxychloride (0.294 mL, 3.80 mmol). After 4 h the reaction was concentrated and quenched by the addition of saturated NaHCO$_3$ (aq). A precipitate formed which was filtered and washed with water to provide the titled compound. $^1$H NMR (DMSO-d$_6$) δ12.35 (bs, 1H), 8.40 (d, 1H, J=5.3 Hz), 8.28 (s, 1H), 7.20 (s, 1H), 7.12 (d, 1H, J=5.3 Hz), 4.82 (s, 2H).

2-[4-(4-Methyl-5-oxo-[1,4]diazepan-1-ylmethyl)-pyridin-2-ylamino]-thiazole-5-carbonitrile (10-4)

4-Methyl-[1,4]diazepan-5-one hydrochloride (0.394 g, 2.39 mmol) was dissolved in 3 mL DMSO. Triethylamine (0.33 mL, 2.4 mmol) was added followed by the addition of 2-(4-chloromethyl-pyridin-2-ylamino)-thiazole-5-carbonitrile (0.200 g, 0.798 mmol). The solution as stirred for 20 h. The reaction mixture was purified directly by loading the solution onto a reverse phase preparative column. The fractions containing pure product were concentrated and the white solid that resulted was characterized as the TFA salt. $^1$H NMR (CD$_3$OD) δ8.47 (d, 1H, J=5.1 Hz), 8.02 (s, 1H), 7.09 (s, 1H), 7.07 (d, 1H, J=5.0 Hz), 3.78 (bs, 2H), 3.61 (bs, 2H), 2.98 (s, 3H), 2.83-2.67 (bs, 6H). [M+H]+=343.2.

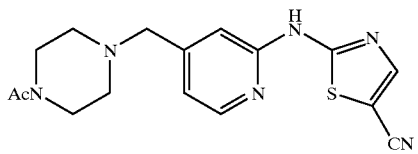

2-[4-(4-Acetyl-piperazin-1-ylmethyl)-pyridin-2-ylamino]-thiazole-5-carbonitrile (10-5)

1-Acetylpiperazine (0.767 g, 5.98 mmol) was dissolved in 4 mL anhydrous DMF. 2-(4-Chloromethyl-pyridin-2-ylamino)-thiazole-5-carbonitrile (0.500 g, 1.99 mmol) was added and the solution as stirred for 4 h. The reaction was diluted with sat NaHCO$_3$ (aq) and the resulting precipitate was filtered and washed with water. The solid was purified by reverse phase chromatography (C18). The fractions containing the desired compound were concentrated to dryness to afford the TFA salt. Elemental analysis: Calculated (for 1.00 TFA) C, 47.36%; H, 4.20%; N, 18.41%; Found C, 47.41%; H, 4.21%; N, 18.49%. $^1$H NMR (free base, CDCl$_3$) δ9.94 (bs, 1H), 8.35 (d, 1H, J=5.1 Hz), 7.99 (s, 1H), 7.00 (d, 1H, J=5.4 Hz), 6.95 (s, 1), 3.66 (t, 2H, 4.8 Hz), 3.56 (s, 2H), 3.52 (t, 2H, J=4.9 Hz), 2.50 (t, 2H, J=5.0 Hz), 2.45 (t, 2H, J=5.0 hz), 2.11 (s, 3H). [M+H]+=343.0. dec 241-245° C.

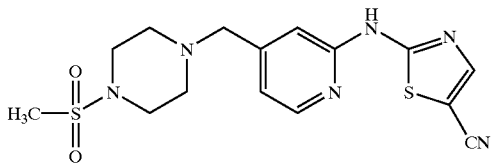

2-[4-(4-Methanesulfonyl-piperazin-1-ylmethyl)-pyridin-2-ylamino]-thiazole-5-carbonitrile (10-6)

1-Methanesulfonyl-piperazine (0.065 g, 0.40 mmol) was dissolved in 0.8 mL anhydrous DMF. 2-(4-Chloromethyl-pyridin-2-ylamino)-thiazole-5-carbonitrile (0.050 g, 0.199 mmol) was added and the solution as stirred overnight. The reaction was diluted with sat NaHCO$_3$ (aq) and the resulting precipitate was filtered and washed with water. The solid was purified by reverse phase chromatography (C18). The fractions containing the desired compound were concentrated to dryness to afford the TFA salt. $^1$H NMR (TFA salt, DMSO-d$_6$) δ12.26 (bs, 1H), 8.39 (bs, 1H), 8.28 (s, 1H), 7.13 (s, 1H), 7.10 (bs, 1H), 3.65 (s, 2H), 3.10 (s, 4H), 3.00 (s, 4H). [M+H]+=379.2.

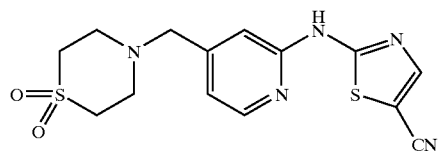

2-[4-(1,1-Dioxo-thiomorpholin-4-ylmethyl)-pyridin-2-ylamino]-thiazole-5-carbonitrile (10-7)

Thiomorpholine 1,1-dioxide (0.058 g, 0.43 mmol) and triethylamine (0.090 mL, 0.65 mmol) were dissolved in 0.8 mL anhydrous DMF. 2-(4-Chloromethyl-pyridin-2-ylamino)-thiazole-5-carbonitrile (0.054 g, 0.215 mmol) was added and the solution as stirred at RT overnight, and was then warmed to 40° C. for 3 h. DMSO, 1 mL was added and the reaction was directly purified by reverse phase chromatography (C18). The fractions containing the desired compound were concentrated to dryness to afford the TFA salt. TFA salt: $^1$H NMR (DMSO-d$_6$) δ12.26 (bs, 1H), 8.35 (d, 1H, J=5.3 Hz), 8.27 (s, 1H), 7.15 (s, 1H), 7.07 (d, 1H, J=5.3 Hz), 3.78 (s, 2), 3.16 (s, 4H), 2.95 (s 4H). [M+H]+=350.1.

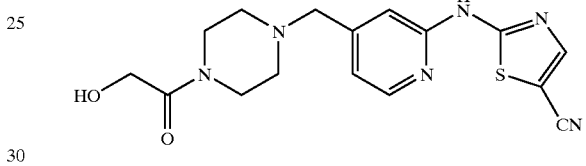

2-{4-[4-(2-Hydroxy-ethanoyl)-piperazin-1-ylmethyl]-pyridin-2-ylamino}-thiazole-5-carbonitrile (10-8)

2-{[4-(Chloromethyl)pyridin-2-yl]amino}-1,3-thiazole-5-carbonitrile (180 mg, 0.72 mmole) and 1-glycoloylpiperazine hydrochloride (259 mg, 1.44 mmole) were combined in DMSO (2 mL). To this was added diisopropylethylamine (0.38 mL, 2.15 mmole) at RT. After 3 hr the mixture was diluted with H$_2$O and extracted with EtOAc (3×g). The combined organic layers were dried (MgSO$_4$), filtered, and concentrated. Flash column chromatography (gradient, 5–15% EtOH/EtOAc then 5–10% MeOH/CHCl3) gave the title compound as a pale yellow solid: $^1$H NMR (d$^6$-DMSO) δ12.19 (s, 1H), 8.33 (d, 1H, J=5.1 Hz), 8.32 (s, 1H), 7.14 (s, 1H), 7.04 (d, 1H, J=5.2 Hz), 4.54 (t, 1H, J=5.6 Hz), 4.08 (d, 2H, J=5.6 Hz), 3.55 (s, 2H), 3.49 (s, 2H), 3.36 (s, 2H), 2.38 (s, 4H); MS [M+H]+= 359.1285.

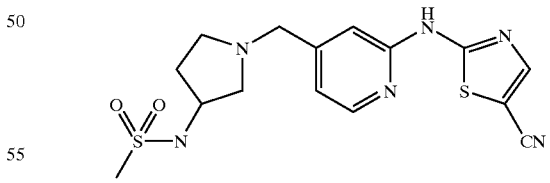

N-{1-[2-(5-Cyano-thiazol-2-ylamino)-pyridin-4-ylmethyl]-pyrrolidin-3-yl}-methanesulfonamide (10-9)

2-(4-Chloromethyl-:2-ylamino)-thiazole-5-carbonitrile (0.055 g, 0.22 mmol) was dissolved in 1 mL DMSO. 3-[(Methylsulfonyl)amino]pyrrolidinium acetate (0.098 g, 0.44 mmol) and triethylamine (0.061 mL, 0.44 mmol) were added and the solution as stirred for 5 hr. The solution was purified by reverse phase chromatography (C18). The fractions containing the desired compound were concentrated to dryness to afford the TFA salt. TFA salt: $^1$H NMR (CD$_3$OD) δ8.52 (d, 1H, J=5.0 Hz), 8.06 (s, 1H), 7.16 (m, 2H), 4.45 (s, 2H), 4.23 (bs, 2H), 3.53 (bs, 1H), 3.01 (s, 3H), 2.51 (bs, 2H), 2.12 (bs, 2H). MS [M+H]+=379.1011.

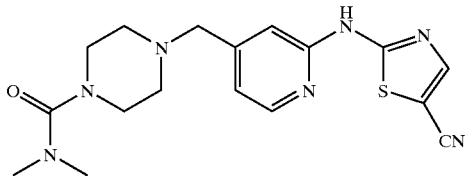

4-({2-[(5-cyano-1,3-thiazol-2-yl)amino]-4-pyridinyl}methyl)-N,N-dimethyl-1-piperazinecarboxamide (10-10)

2-(4-Chloromethyl-pyridin-2-ylamino)-thiazole-5-carbonitrile (0.119 g, 0.47 mmol) was dissolved in 1 mL DMSO. N,N-Dimethyl-1-piperazinecarboxamide (0.149 g, 0.95 mmol) was added and the solution was stirred for 3.5 hr. Additional N,N-dimethyl-1-piperazinecarboxamide (0.149 g, 0.95 mmol) was added and the solution was stirred for 1.5 hr. The reaction was diluted with water and the resulting precipitate collected by filtration. The solid was washed with water and hexanes then air dried overnight to afford the free base. Free base: $^1$H NMR (CD$_3$OD) δ8.33 (d, 1H, J=5.0Hz), 8.03 (s, 1H), 7.08 (s, 1H), 7.04 (d, 1H, J=5.0 Hz), 3.58 (s, 1H), 3.29 (t, 4H, J=6.0 Hz), 2.84 (s, 6H), 2.49 (t, 4H, J=Hz). MS [M+H]+=372.1611.

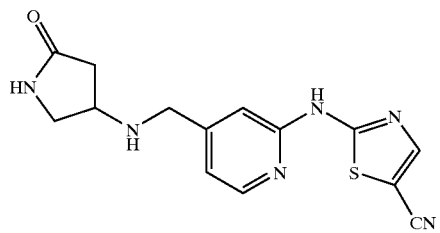

2-[(4-{[(5-oxo-3-pyrrolidinyl)amino]methyl}-2-pyridinyl)amino]-1,3-thiazole-5-carbonitrile (10-11)

2-(4-Chloromethyl-pyridin-2-ylamino)-thiazole-5-carbonitrile (0.092 g, 0.37 mmol) was dissolved in 1 mL DMSO. 4-Amino-2-pyrrolidinone (0.074 g, 0.74 mmol) was added and the solution as stirred for 24 hr. Diisopropylethylamine (0.129 mL, 0.74 mmol) was added and the solution was heated to 35° C. for 20 hr. The solution was allowed to cool to room temperature and purified by reverse phase chromatography (C18). The fractions containing the desired compound were concentrated to dryness to afford the TFA salt. The TFA salt was taken up in saturated NaHCO$_3$ (aq) and extracted with 5% n-butanol/DCM. The combined organic layers were dried (Na2SO4), filtered, and concentrated to afford the free base. Free base: $^1$H NMR (CD$_3$OD) δ8.32 (d, 1H, J=5.0 Hz), 8.02 (s, 1H), 7.06 (m, 2H), 3.80 (d, 1H, J=5.0 Hz), 3.59 (m, 1H), 2.56 (m, 1H), 2.23 (m, 1H), 1.54 (m, 1H), 1.39 (m, 1H). MS [M+H]+=315.1017.

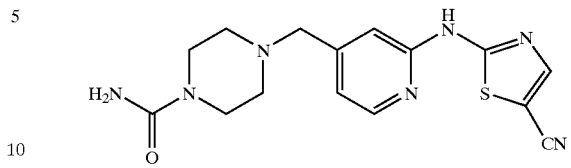

4-({2-[(5-cyano-1,3-thiazol-2-yl)amino]-4-pyridinyl}methyl)-1-piperazinecarboxamide (10-12)

1-Piperazinecarboxamide (0.144 g, 1.12 mmol) was dissolved in 1 mL DMSO. 2-(4-Chloromethyl-pyridin-2-ylamino)-thiazole-5-carbonitrile (0.070 g, 0.28 mmol) was added and the solution as stirred for 4.75 hr. The reaction was diluted with water and the resulting precipitate collected by filtration and washed with water. The solid was purified by reverse phase chromatography (C18). The fractions containing the desired compound were concentrated to dryness to afford the TFA salt. TFA salt: $^1$H NMR (CD$_3$OD) δ8.49 (d, 1H, J=5.0 Hz), 8.06 (s, 1H), 7.15 (m, 2H), 4.25 (s, 2H), 3.64 (bs, 4H), 3.15 (s, 4H). MS [M+H]+=344.1250.

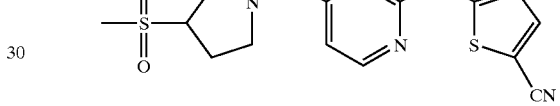

2-[(4-{[3-(methylsulfonyl)-1-pyrrolidinyl]methyl}-2-pyridinyl)amino]-1,3-thiazole-5-carbonitrile (10-13)

2-(4-Chloromethyl-pyridin-2-ylamino)-thiazole-5-carbonitrile (0.078 g, 0.31 mmol) was dissolved in 1 mL DMSO. 3-(Methylsulfonyl)pyrrolidinium chloride (0.232 g, 1.25 mmol) and triethylamine (0.174 mL, 1.25 mmol) were added and the solution was stirred for 5.25 hr. The reaction was diluted with water and the resulting precipitate collected by filtration and washed with water. The solid was purified by reverse phase chromatography (C18). The fractions containing the desired compound were concentrated to dryness to afford the TFA salt. The TFA salt was taken up in saturated NaHCO$_3$ (aq) aid extracted with 5% n-butanol/CH2Cl2. The combined organic layers were dried (Na2SO4), filtered, and concentrated to afford the free base. Free base: $^1$H NMR (CD$_3$OD) δ8.32 (d, 1H, J=5.0 Hz), 8.01 (s, 1H), 7.07 (s, 1H), 7.04 (d, 1H, J=5.0 Hz), 3.78 (m, 1H), 3.71 (d, 2H, J=6.0 Hz), 3.04 (m, 1H), 2.93 (s, 3H), 2.91 (m, 1H), 2.81 (m, 1H), 2.64 (m, 1H), 2.27 (m, 2H). MS [M+H]+=364.0913.

The following compounds, 10-14 through 10-34, were prepared in the same fashion:

| No. | Structure | Name | [M + H]+ |
|---|---|---|---|
| 10-14 | 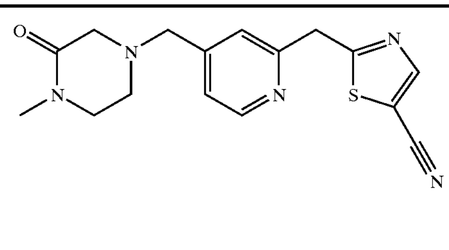 | 2-[4-(4-Methyl-3-oxo-piperazin-1-ylmethyl)-pyridin-2-ylamino]-thiazole-5-carbonitrile | 329.3 |

-continued

| No. | Structure | Name | [M + H]+ |
|---|---|---|---|
| 10-15 | 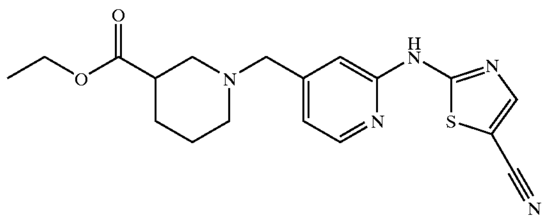 | 1-[2-(5-Cyano-thiazol-2-ylamino)-pyridin-4-ylmethyl]-piperidine-3-carboxylic acid ethyl ester | 372.3 |
| 10-16 | 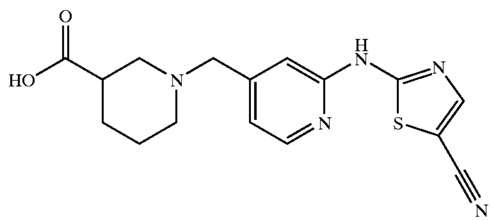 | 1-[2-(5-Cyano-thiazol-2-ylamino)-pyridin-4-ylmethyl]-piperidine-3-carboxylic acid | 344.3 |
| 10-17 | 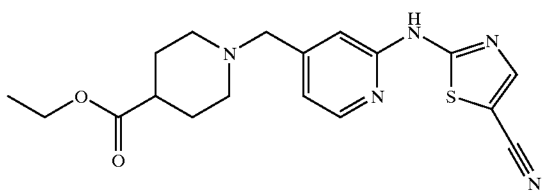 | 1-[2-(5-Cyano-thiazol-2-ylamino)-pyridin-4-ylmethyl]-piperidine-4-carboxylic acid ethyl ester | 372.3 |
| 10-18 | 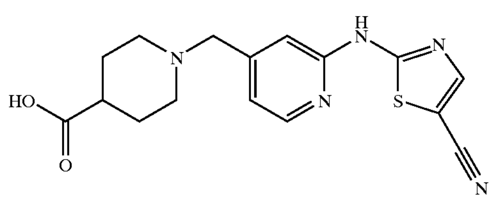 | 1-[2-(5-Cyano-thiazol-2-ylamino)-pyridin-4-ylmethyl]-piperidine-4-carboxylic acid | 344.2 |
| 10-19 | 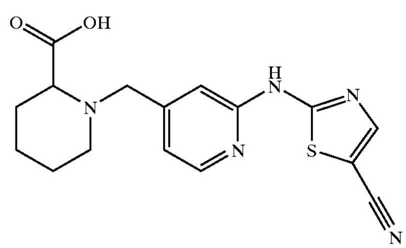 | 1-[2-(5-Cyano-thiazol-2-ylamino)-pyridin-4-ylmethyl]-piperidine-2-carboxylic acid | 344.2 |
| 10-20 | 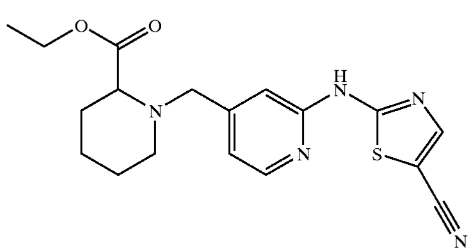 | 1-[2-(5-Cyano-thiazol-2-ylamino)-pyridin-4-ylmethyl]-piperidine-2-carboxylic acid ethyl ester | 372.3 |
| 10-21 | 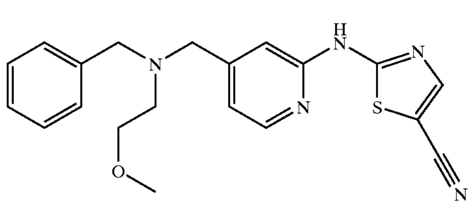 | 2-(4-{[Benzyl-(2-methoxy-ethyl)-amino]-methyl}-pyridin-2-ylamino)-thiazole-5-carbonitrile | 380.2 |

| No. | Structure | Name | [M + H]+ |
|---|---|---|---|
| 10-22 | 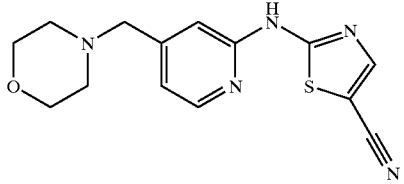 | 2-(4-Morpholin-4-ylmethyl-pyridin-2-ylamino)-thiazole-5-carbonitrile | 302.2 |
| 10-23 | 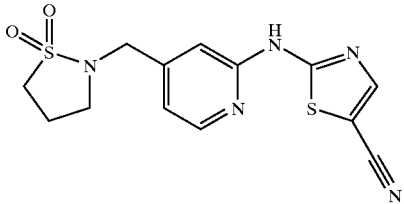 | 2-[4-(1,1-Dioxo-isothiazolidin-2-ylmethyl)-pyridin-2-ylamino]-thiazole-5-carbonitrile | 336.1 |
| 10-24 | 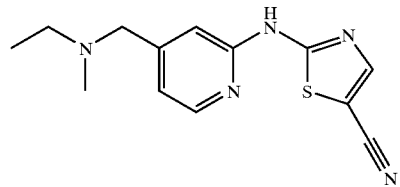 | 2-(4-Dimethylaminomethyl-pyridin-2-ylamino)-thiazole-5-carbonitrile | 260.2 |
| 10-25 | 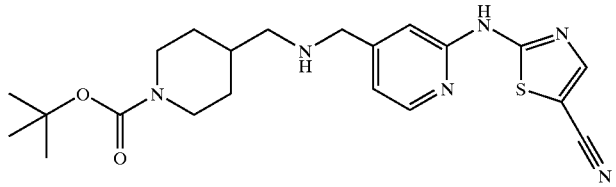 | 4-({[2-(5-Cyano-thiazol-2-ylamino)-pyridin-4-ylmethyl]-amino}-methyl)-piperidine-1-carboxylic acid tert-butyl ester | 429 |
| 10-26 | 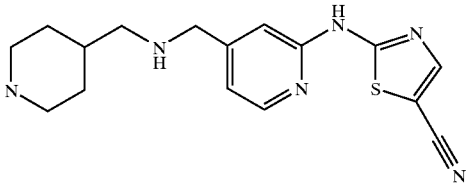 | 2-(4-{[(Piperidin-4-ylmethyl)-amino]-methyl}-pyridin-2-ylamino)-thiazole-5-carbonitrile | 329 |
| 10-27 | 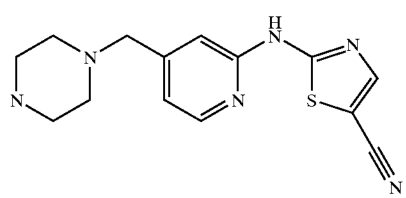 | 2-(4-Piperazin-1-ylmethyl-pyridin-2-ylamino)-thiazole-5-carbonitrile | 301.1 |
| 10-28 | 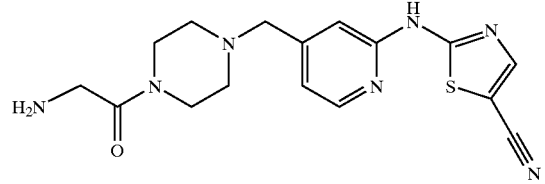 | 2-{4-[4-(2-Amino-ethanoyl)-piperazin-1-ylmethyl]-pyridin-2-ylamino}-thiazole-5-carbonitrile | 358.2 |

-continued

| No. | Structure | Name | [M + H]+ |
|---|---|---|---|
| 10-29 | 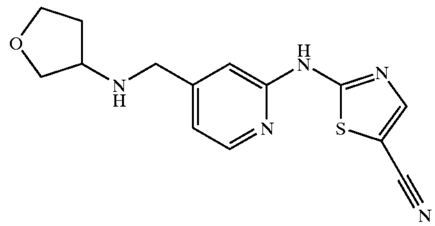 | 2-{4-[(Tetrahydro-furan-3-ylamino)-methyl]-pyridin-2-ylamino}-thiazole-5-carbonitrile | 302.1 |
| 10-30 | 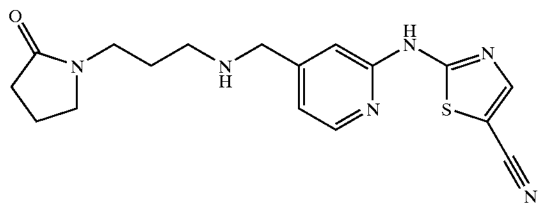 | 2-(4-{[3-(2-Oxo-pyrrolidin-1-yl)-propylamino]-methyl}-pyridin-2-ylamino)-thiazole-5-carbonitrole | 357 |
| 10-31 | 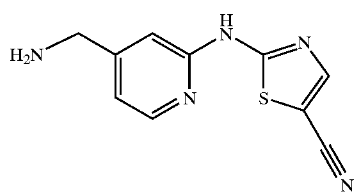 | 2-(4-Aminomethyl-pyridin-2-ylamino)-thiazole-5-carbonitrile | 232 |
| 10-32 | 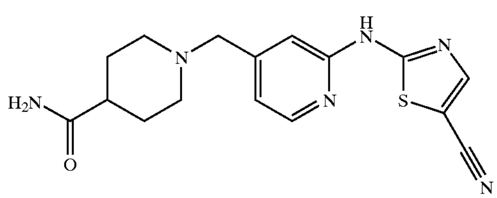 | 1-[2-(5-Cyano-thiazol-2-ylamino)-pyridin-4-ylmethyl]-piperidine-4-carboxylic acid amide | 343 |
| 10-33 | 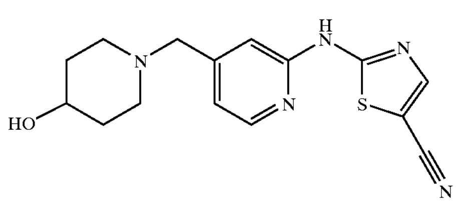 | 2-[4-(4-Hydroxy-piperidin-1-ylmethyl)-pyridin-2-ylamino]-thiazole-5-carbonitrile | 316.1 |
| 10-34 | 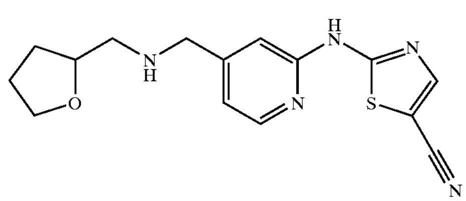 | 2-(4-{[(Tetrahydro-furan-2-ylmethyl)-amino]-methyl}-pyridin-2-ylamino)-thiazole-5-carbonitrile | 316 |

SCHEME 11

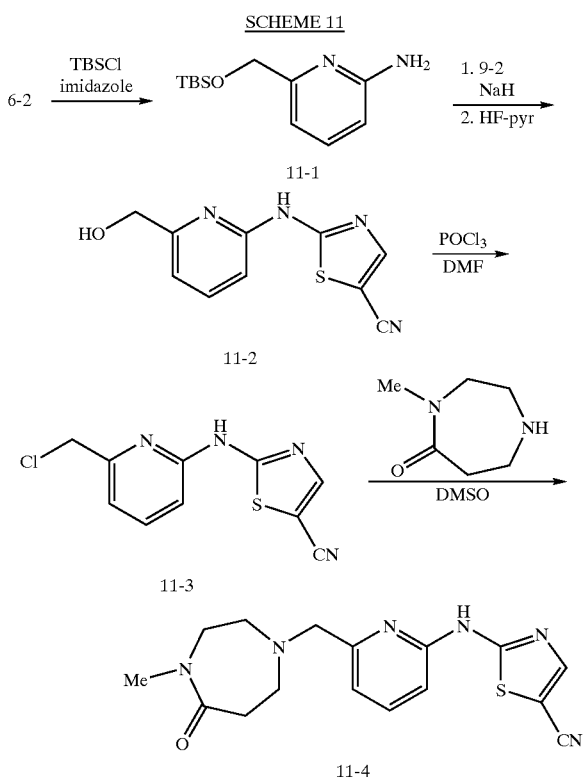

6-(tert-Butyl-dimethyl-silanyloxymethyl)-pyridin-2-ylamine (11-1)

(6-Amino-pyridin-2-yl)-methanol (1.45 g, 11.7 mmol), TBSCl (1.94 g, 12.9 mmol) and imidazole (0.954 g, 14.0 mmol) were dissolved in 23 mL anhydrous DMF under $N_2$. After 5 h the reaction was diluted with ater and extracted 3× with EtOAc. The combined organic extracts were dried over $Na_2SO_4$, filtered and concentrated. Purification by flash column chromatography (eluting with 98:2 DCM/MeOH) afforded pure titled compound. $^1$H NMR (CDCl$_3$) δ7.45 (t, 1H, J=7.7 Hz), 6.86 (d, 1H, J=8.6 Hz), 6.36 (d, 1H, J=8.2 Hz), 4.65 (s, 2H), 4.35 (bs, 2H), 0.95 (s, 9H), 0.10 (s, 6H).

2-(6-Hydroxymethyl-pyridin-2-ylamino)-thiazole-5-carbonitrile (11-2)

An oven dried flask was charged with 6-(tert-butyl-dimethyl-silanyloxymethyl)-pyridin-2-ylamine (1.27 g, 5.33 mmol) and 10 mL anhydrous THF. The solution was cooled to 0° C. and NaH (60% dispersion, 0.43 g, 11 mmol) was added. The reaction was warmed to room temperature and 2-chloro-thiazole-5-carbonitrile (0.924 g, 6.39 mmol) was added. The reaction was heated to 50° C. for 4 h. An additional 0.200 g (1.38 mmol) 2-chloro-thiazole-5-carbonitrile was added and the reaction was heated overnight. After a total of 18 h the reaction was cooled and quenched with water. The pH was adjusted to 7 with 1M HCl. The resulting precipitate was filtered and washed with water. Purification in two batches by flash column chromatography (suspended material on 5g silica, eluted DCM to 97:3 DCM/MeOH) afforded a mixture of the aminothiazole and starting aminopyridine. This aminothiazole (0.710 g, 2.05 mmol) was dissolved in 10 mL anhydrous THF and the resulting solution was cooled to 0° C. HF-pyr, 2.4 mL, was added and the reaction was allowed to warm to room temperature. After 1 h the reaction was quenched by the addition of sat NaHCO3 (aq) and the THF was removed in vacuo. The resulting precipitate was filtered and washed with water to provide the titled compound. $^1$H NMR (DMSO-d$_6$) δ12.18 (s, 1H), 8.22 (s, 1H), 7.78 (t, 1H, J=7.6 Hz), 7.10 (d, 1H, J=7.5 Hz), 6.96 (d, 1H, J=8.2 Hz), 5.45 (t, 1H, J=5.7 Hz), 4.59 (d, 2H, J=5.9 Hz).

2-(6-Chloromethyl-pyridin-2-ylamino)-thiazole-5-carbonitrile (11-3)

2-(6-Hydroxymethyl-pyridin-2-ylamino)-thiazole-5-carbonitrile (0.300 g, 0.29 mmol) was stirred in 5 mL anh DCM under $N_2$. Anhydrous DMF (0.100 mL, 1.29 mmol) and POCl$_3$ (0.120 mL, 1.29 mmol) were added. After 15 h the reaction was diluted with water and the pH was adjusted to 9 with sat NaHCO$_3$ (aq). The dCM was removed in vacuo and the precipitate which formed was filtered and washed with water to provide the titled compound. $^1$H NMR (DMSO-d$_6$) δ12.35 (s, 1H), 8.29 (s, 1H), 7.85 (t, 1H, J=7.8 Hz, 7.21 (d, 1H, 7.3 Hz), 7.11 (d, 1H, 8.2 Hz), 4.85 (s, 2H).

2-[6-(4-Methyl-5-oxo-[1,4](diazepan-1-ylmethyl)-pyridin-2-ylamino]-thiazole-5-carbonitrile (11-4)

4-Methyl-[1,4]diazepan-5-one hydrochloride (0.092 g, 0.028 mmol) was dissolved in 1 mL DMSO. Triethylamine (0.12 mL, 0.84 mmol) was added followed by the addition 2-(6-Chloromethyl-pyridin-2-ylamino)-thiazole-5-carbonitrile (0.070 g, 0.28 mmol). The solution as stirred for 2 h. The reaction mixture was purified directly by loading the solution onto a reverse phase preparative column. The fractions containing pure product were concentrated and the white solid that resulted was characterized as the TFA salt. $^1$H NMR (CD$_3$OD) δ8.07 (s, 1H), 7.91 (dd, 1H, J=7.5, 8.2 Hz), 7.30 (d, 1H, J=7.3 Hz), 7.19 (d, 1H, J=8.4 Hz), 4.56 (s, 2H), 3.83 (bs, 2H), 3.64 (bs, 4H), 3.01 (s, 3H), 2.93 (bs, 2H). MS [M+H]+=343.2.

The following example was prepared by the same method:

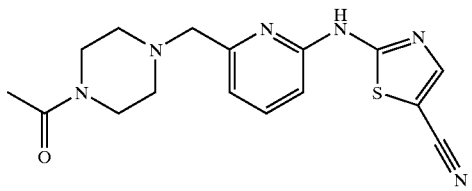

2-[6-(4-Acetyl-piperazin-1-ylmethyl)-pyridin-2-ylamino]-thiazole-5-carbonitrile (11-5)

TFA salt: $^1$H NMR (DMSO-d$_6$) δ12.41 (s, 1H), 10.20 (s, 1H), 8.32 (s, 1H), 7.95 (t, 1H, J=7.6 Hz), 7.30 (d, 1H, J=7.0 Hz), 7.21 (d, 1H, J=7.8 Hz), 4.46 (bs, 3H), 4.03 (bs, 3H), 3.39–3.12 (m, 4H), 2.03 (s, 3H). MS [M+H]+=343.0.

SCHEME 12

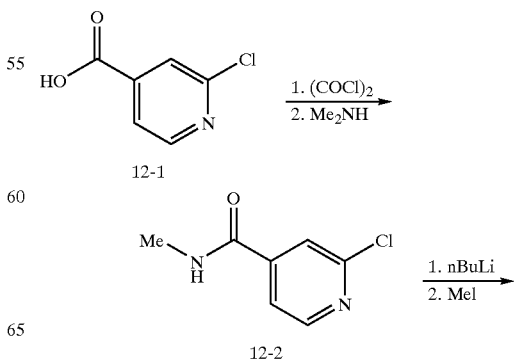

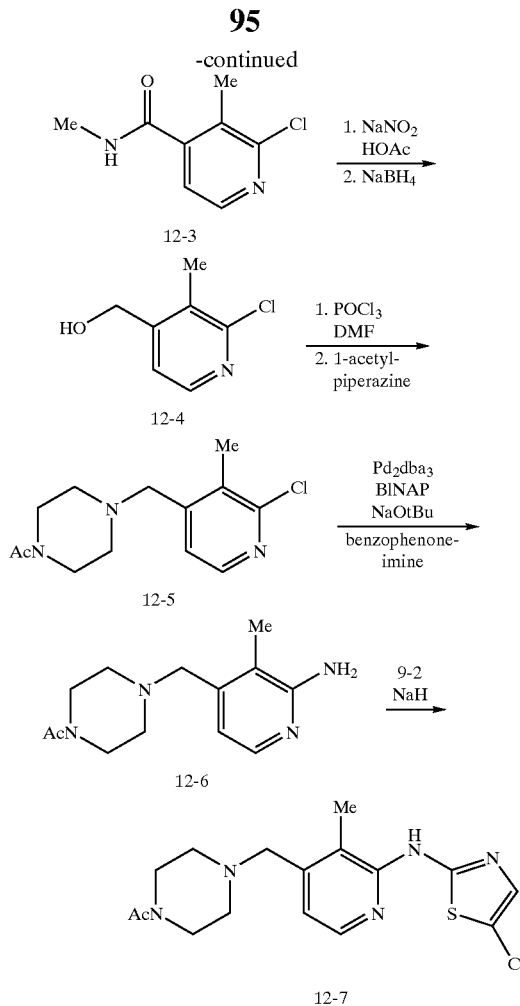

2-Chloro-N-methyl-isonicotinamide (12-2)

2-Chloro-isonicotinic acid (12-1, 5.15 g, 32.7 mmol) was stirred in 65 mL anhydrous THF under $N_2$. The reaction (not homogeneous) was cooled to 0° C. and oxalyl chloride (2.85 mL, 32.7 mmol) was added, followed by addition of 1 drop anh DMF. Slight bubbling occurs. The reaction was allowed to warm to RT. After 4 h reaction is homogeneous and after a total of 5 h the reaction was quickly added by pipet to a solution of methylamine (7.11 g, 228 mmol) in EtOH (20 mL). The resulting solution was concentrated in vacuo and diluted with sat $NaHCO_3$ (aq). The solution was extracted 3× with EtOAc and the organic extracts were dried over $Na_2SO_4$, filtered ands concentrated to provide the titled compound. $^1$H NMR (CDCl$_3$) δ8.50 (d, 1H, J=5.1 Hz), 7.66 (s, 1H), 7.53 (d, 1H, J=5.1 Hz), 6.36 (bs, 1H), 3.04 (d, 2H, J=5.0 Hz).

2-Chloro-3,N-dimethyl-isonicotinamide (12-3)

2-Chloro-N-methyl-isonicotinamide (12-2, 1.03 g, 6.04 mmol) was dissolved in 12 mL anhydrous THF and the resulting solution was cooled to −78° C. nBuLi (1.6 M in hexane, 7.55 mL, 12.1 mmol) was added slowly. After 20 min MeI (0.375 mL, 6.04 mmol) was added slowly. Approximately halfway through the addition a brown gum quickly formed in the mixture. The remainder of the MeI was added and the reaction was allowed to warm to 0° C. and then to RT. After 30 min at RT the reaction was quenched with water. The mixture was extracted 3× with EtOAc, and the organic extracts were dried over $Na_2SO_4$, filtered, and concentrated. $^1$H NMR shows 2:1:1 desired-:dimethylated pdt:starting material. Purify by flash column chromatography (98:2 DCM/MeOH) afforded a 2:1 mixture of the titled compound and 2-chloro-3,N-dimethyl-isonicotinamide.

(2-Chloro-3-methyl-pyridin-4-yl)-methanol (12-4)

2-Chloro-3,N-dimethyl-isonicotinamide (12-3, impure, 0.160 g) was stirred in 3 mL 2:1 HOAc/Ac$_2$O. The solution was cooled to 0° C., and NaNO$_2$ (0.120 g, 1.73 mmol) was added. After 30 min the reaction was allowed to warm to RT. After 6 h an additional 60 mg (0.87 mmol) NaNO$_2$ was added, and the reaction was stirred overnight. The solution was diluted with sat NaHCO3 (aq), and extracted 3× w/EtOAc. The combined organic phases were dried over $Na_2SO_4$, filtered and concentrated. The residue was purified by flash column chromatography (4:1 hex/EA (used a little DCM to dissolve sample in mobile phase to produce the nitroso amide, still as a 3:1 mixture with a by-product. A sample of this mixture (0.227 g) was dissolved in 4 mL THF. NaBH$_4$ (0.120 g, 3.17 mmol) was added and the resulting reaction was stirred at RT for 1 h. The reaction was quenched with 1M hCl. The solution was then basified with sat NaHCO$_3$ (aq) and extracted 3× with EtOAc. The combined organic phases were dried over $Na_2SO_4$, filtered and concentrated to provide the titled compound as a colorless oil, still contaminated with a by-product.

1-[4-(2-Chloro-3-methyl-pyridin-4-ylmethyl)-piperazin-1-yl]-ethanone (12-5)

(2-Chloro-3-methyl-pyridin-4-yl)-methanol (12-4, impure, 0.200 g) was dissolved in 5 mL anhydrous DCM under $N_2$. Anhydrous DMF (0.098 mL, 1.3 mmol) and POCl$_3$ (0.118 mL, 1.27 mmol) were added and the reaction was stirred at RT for 17 h. The reaction was quenched with sat NaHCO$_3$ (aq) and extracted 3× with DCM. The organic phases were dried over $Na_2SO_4$, filtered and concentrated to provide 2-chloro-4-chloromethyl-3-methyl-pyridine still contaminated with a major by-product. 2-Chloro-4-chloromethyl-3-methyl-pyridine (impure, 0.215 g) was stirred in 3 mL DMSO. 1-Acetylpiperazine (0.626 g, 4.88 mmol was added and the reaction was stirred at RT overnight. The solution was purified by directly loading onto a preparative reverse phase column to afford an oil which slowly crystallizes. TFA salt: $^1$H NMR (CD$_3$OD) δ8.30 (d, 1H, J=5.0 Hz), 7.53 (d, 1H, J=5.0 Hz), 4.48 (s, 2H), 3.84 (bs, 4H), 3.39–3.30 (m, 4H), 2.14 (s, 3H).

1-[4-(2-Amino-3-methyl-pyridin-4-ylmethyl)-piperazin-1-yl]-ethanone (12-6)

1-[4-(2-Chloro-3-methyl-pyridin-4-ylmethyl)-piperazin-1-yl]-ethanone (free base, 0.040 g, 0.15 mmol), NaOtBu (0.020 g, 0.21 mmol), BINAP (0.014 g, 0.020 mmol), and Pd$_2$dba$_3$ (0.0068 g, 0.0103 mmol) were stirred in 1 mL anhydrous toluene under $N_2$. Benzophenone imine (0.030 mL, 0.18 mmol) was added and the reaction was heated to 80° C. After 3 h the reaction was cooled to RT, diluted with Et$_2$O, filtered through celite, and concentrated in vacuo. To the residue was added 1:1 THF/1M HCl. The mixture was stirred for 2 h, then washed 2× w/EtOAc. The aqueous phase was adjusted to pH 10 with Na$_2$CO$_3$ (solid). The solution was extracted 3× with DCM/nBuOH (95:5), and the combined organic extracts were dried over $Na_2SO_4$, filtered, concentrated. The residue was purified by flash column chromatography (95:5-90:10 DCM/MeOH) to afford the pure titled compound. $^1$H NMR (CDCl$_3$) δ7.89 (d, 1H, J=5.1 Hz), 6.65 (d, 1H, J=5.1 Hz), 4.45 (bs, 2H), 3.61 (t, 2H, J=4.9 Hz), 3.43 (m, 4H), 2.41 (t, 4H, J=5.2 Hz), 2.12 (s, 3H), 2.08 (s, 3H).

2-[4-(4-Acetyl-piperazin-1-ylmethyl)-3-methyl-pyridin-2-ylamino]-thiazole-5-carbonitrile (12-7)

NaH (60% dispersion, 14 mg, 0.35 mmol) was stirred in 1 mL anhydrous THF. 1-[4-(2-Amino-3-methyl-pyridin-4- ylmethyl)-piperazin-1-yl]-ethanone (0.039 g, 0.157 mmol) was added followed, after 10 min by the addition of 2-chloro-thiazole-5-carbonitrile (0.027 g, 0.19 mmol). The reaction was stirred at RT for 30 min then was heated to reflux. After 2 h an additional 0.010 g NaH (0.25 mmol) was added. After 1 h the reaction was cooled to RT and quenched with water. The pH was adjusted to 7 with 1M HCl and the mixture was extracted 3× with EtOAc. The combined organic phases were dried over $Na_2SO_4$, filtered and concentrated. The residue was purified by reverse phase HPLC to provide the pure titled compound. TFA salt: $^1$H NMR ($CD_3OD$) δ8.37 (d, 1H, J=5.1 Hz), 8.08 (s, 1H), 7.19 (d, 1H, J=5.1 Hz), 4.45 (s, 2H), 3.81 (bs, 4H), 3.35 (s, 4H), 2.47 (s, 3H), 2.15 (s, 3H). MS [M+H]+=357.3.

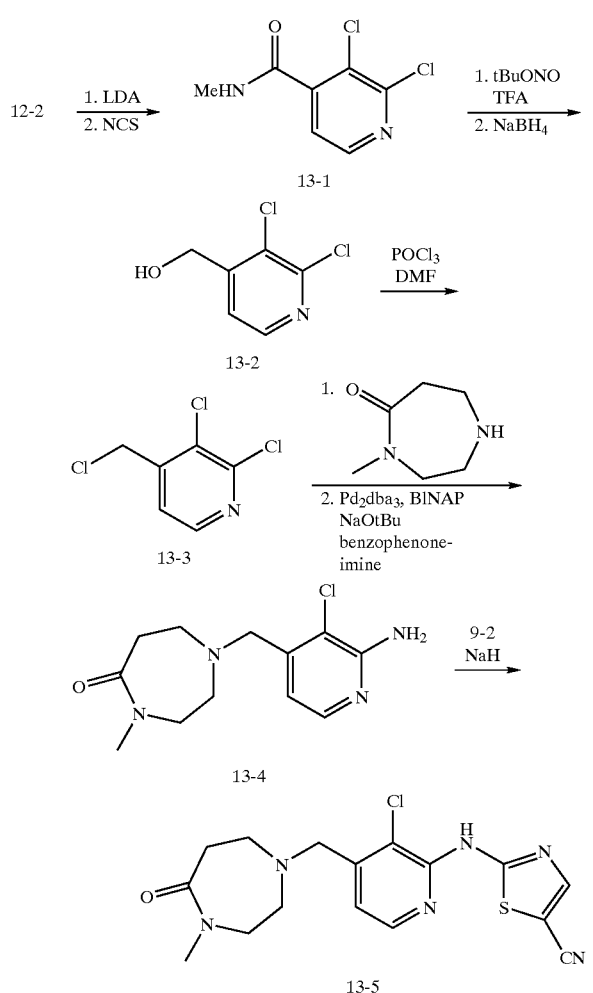

2,3-Dichloro-N-methyl-isonicotinamide (13-1)

2-Chloro-N-methyl-isonicotinamide (12-2, 1.19 g, 6.98 mmol) was dissolved in 20 mL anhydrous THF and the solution was cooled to −78° C. LDA (2M, 7.33 mL, 14.7 mmol) was added dropwise and the reaction turns orange. After 15 min NCS (1.02 g, 7.67 mmol) was added and the reaction was allowed to warm to RT. After 1 h at RT HPLC shows ~3:1 starting material/product. The reaction was quenched with water, extracted 3× w/ EtOAc, and the organic phases were dried over $Na_2SO_4$, filtered, and concentrated. The residue vias purified by preparative reverse phase HPLC to afford the pure titled compound. $^1$H NMR ($CDCl_3$) δ8.36 (d, 1H, J=4.8 Hz), 7.41 (d, 1H, J=4.8 Hz), 6.10 (bs, 1H), 3.05 (d, 3H, J=4.9 Hz).

(2,3-Dichloro-pyridin-4-yl)-methanol (13-2)

2,3-Dichloro-N-methyl-isonicotinamide (0.353 g, 1.72 mmol) was stirred in 6 mL DCM (not quite homogeneous). tBuONO (0.412 mL, 3.44 mmol) was added followed by the addition of two drops of TFA. After 3 h an additional 0.600 ML tBuONO (5.00 mmol) and three drops TFA were added. The resulting solution was stirred an additional 16 h. An additional 0.400 mL tBuONO (3.34 mmol) and 2 drops TFA were added. After an additional 4.5 h an 0.600 mL tBuONO (5.00 mmol) and 3 drops TFA were added. The reaction was stirred 3 days and was quenched with half-sat NaHCO3 (aq). The mixture was extracted 3× with DCM. The organic phases were dried over $Na_2SO_4$, filtered, and concentrated. The slightly impure N-nitrosoamide (0.425 g, 1.82 mmol) was stirred in 5 mL THF. NaBH4 (0.137 g, 3.63 mmol) was added and after 2 h the reaction was slowly quenched with 1M HCl until the bubbling stopped. The solution pH was adjusted to pH 9 with $Na_2CO_3$ (s). The mixture was extracted 3× with EtOAc. The organic phases were dried over $Na_2SO_4$, filtered, and concentrated to afford the titled compound in good purity. $^1$H NMR ($CDCl_3$) δ8.32 (d, 1H, J=4.8 Hz), 7.51 (d, 1H, J=5.0 Hz), 4.82 (s, 2H), 2.34 (bs, 1H).

2,3-Dichloro-4-chloromethyl-pyridine (13-3)

(2,3-Dichloro-pyridin-4-yl)-methanol (0.256 g, 1.44 mmol) was dissolved in 5 mL anhydrous under $N_2$. Anhydrous DMF (0.111 mL, 1.44 mmol) was added followed by dropwise addition of $POCl_3$ (0.134 mL, 1.44 mmol). The reaction was stirred at RT overnight. After 16 h the reaction was quenched by the addition of sat aq NaHCO3. The mixture was extracted 3× with DCM. The organic phases were dried over $Na_2SO_4$, filtered, and concentrated to provide the pure titled compound. $^1$H NMR ($CDCl_3$) δ8.33 (d, 1H, J=4.9 Hz), 7.44 (d, 1H, J=4.9 Hz), 4.68 (s, 2H).

1-(2-Amino-3-chloro-pyridin-4-ylmethyl)-4-methyl-[1,4] diazepan-5-one (13-4)

2,3-Dichloro-4-chloromethyl-pyridine (0.272 g, 1.39 mmol) was dissolved in 4 mL DMSO. $Et_3N$ (0.386 mL, 2.77 mmol) was added followed by the addition of 4-methyl-[1,4]diazepan-5-one hydrochloride (0.456 g, 2.77 mmol). The mixture was stirred for 16 h, then diluted with sat aq NaHCO3. The resulting precipitate was filtered and washed with water. Afforded a white solid—primarily desired contaminated with a small amount of the starting chloromethylpyridine. The filtrate was extracted 3× with EtOAc. The organic phases were washed 2× with sat aq NaCl, dried over $Na_2SO_4$, filtered, and concentrated to afford additional desired compound. Unpurified 1-(2-amino-3-chloro-pyridin-4-ylmethyl)-4-methyl-[1,4]diazepan-5-one (0.100 g, 0.347 mmol), NaOtBu (0.047 g, 0.49 mmol), BINAP (0.032 g, 0.050 mmol), and $Pd_2dba_3$ (0.016 g, 0.020 mmol) were stirred in 2 mL anhydrous toluene under $N_2$. Benzophenone imine (0.070 mL, 0.42 mmol) was added and the reaction was heated to 80° C. After 3 h the reaction was cooled to RT and concentrated in vacuo. To the residue was added 1:1 THF/1M HCl. The mixture was stirred for 1 h, then adjusted to pH 10 with $Na_2CO_3$ (solid). The solution was extracted 3× with EtOAc and the combined organic extracts were dried over $Na_2SO_4$, filtered, concentrated. The residue was purified by flash column chromatography (DCM to 95:5 DCM/MeOH) to afford the pure titled compound. $^1$H NMR ($CDCl_3$) δ7.96 (d, 1H, J=5.1 Hz), 6.82 (d, 1H, J=5.1 Hz), 4.95 (bs, 2H), 3.61 (s, 2H), 3.43 (m, 2H), 3.00 (s, 3H), 2.65 ( m, 6H).

2-[3-Chloro-4-(4-methyl-5-oxo-[1,4]diazepan-1-ylmethyl)-pyridin-2-ylamino]-thiazole-5-carbonitrile (13-5)

NaH (0.016 g, 0.40 mmol) was stirred in anhydrous THF, 1.5 mL, under $N_2$. 1-(2-Amino-3-chloro-pyridin-4- ylmethyl)-4-methyl-[1,4]diazepan-5-one (0.045 g, 0.17 mmol) was added followed after 10 min by the addition of 2-chloro-thiazole-5-carbonitrile (0.034 g, 0.23 mmol) and the reaction was heated to reflux. After 4 h the reaction was cooled to RT and quenched by the addition of water. The pH was adjusted to 7 with 1M HCl and the mixture was extracted 3× with EtOAc. The organic extracts were dried over $Na_2SO_4$, filtered and concentrated. The residue was purified by preparative reverse phase HPLC to afford a colorless oil. The residue was azeotroped 3× with MeOH and the resulting residue was dissolved in a minimum of MeOH. The solvent slowly evaporated to afford a white solid which was further dried in vacuo. TFA salt: $^1$H NMR ($CD_3OD$) δ8.46 (d, 1H, J=5.1 Hz), 8.12 (s, 1H), 7.34 (d, 1H, J=5.1 Hz), 4.43 (s, 2H), 3.75 (m, 2H), 3.36 (m, 4H), 3.02 (s, 3H), 2.88 (m, 2H). MS [M+H]+=377.2.

SCHEME 14

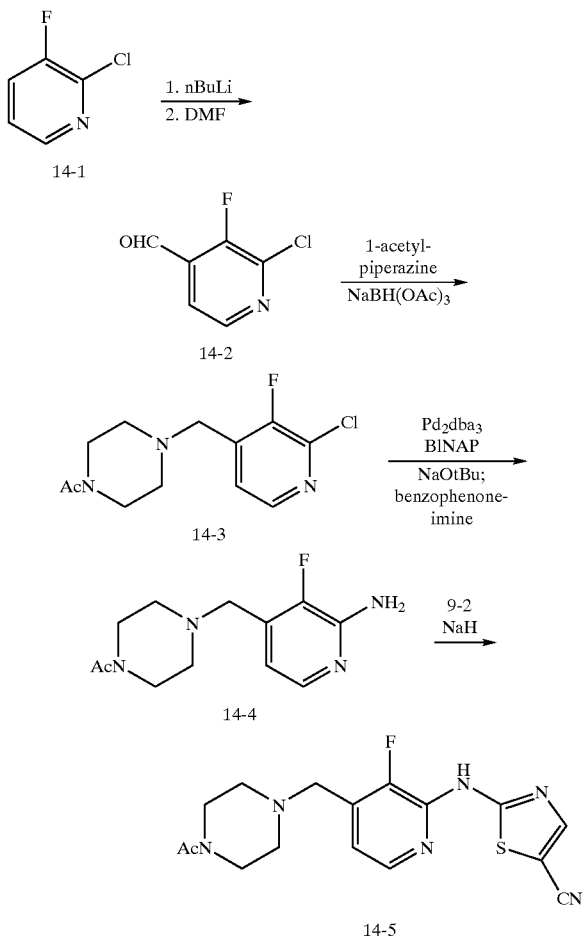

2-Chloro-3-fluoro-pyridine-4-carbaldehyde (14-2)

2-Chloro-3-fluoro-pyridine (14-1, 0.300 g, 2.28 mmol) was dissolved in anhydrous THF, 6 mL, and the solution was cooled to −78° C. nBuLi (2.5 M, 1.00 mL, 2.50 mmol) was added dropwise. After 20 min anhydrous DMF (0.212 mL, 2.74 mmol) was added to reaction. After 15 min the reaction was allowed to warm to RT. The mixture was quenched with water, extracted 3× with DCM and the organic phases were dried over $Na_2SO_4$, filtered and concentrated. The residue was purified by flash column chromatography (10 g column, 1:1 DCM/hexanes) to provide desired aldehyde. $^1$H NMR ($CDCl_3$) δ10.42 (s, 1H), 8.41 (d, 1H, J=4.1 Hz), 7.65 (t, 1H, J=4.6 Hz).

1-[4-(2-Chloro-3-fluoro-pyridin-4-ylmethyl)-piperazin-1-yl]-ethanone (14-3)

1-Acetylpiperazine (0.164 g 1.28 mmol)was dissolved in 5 mL DCE and the resulting solution was added to 2-chloro-3-fluoro-pyridine-4-carbaldehyde (14-2, 0.170 g, 1.07 mmol). $NaBH(OAc)_3$ (0.248 g, 1.17 mmol) was added followed by the addition of 0.100 mL of HOAc. After 45 min the reaction was quenched with sat $NaHCOC_3$ (aq). The mixture was extracted 3× with DCM, and the organic extracts were dried over $Na_2SO_4$, filtered and concentrated. The residue was purified by flash column chromatography (10 g column, DCM (for 4 min) gradient to 95:5 DCM/MeOH (over 8 min)), desired comes off shortly after 95:5 is attained (13 min) affording good separation from close peak preceeding desired. Afforded pure titled compound. $^1$H NMR ($CDCl_3$) δ8.18 (d, 1H, J=4.9 Hz), 7.38 (t, 1H, J=4.6 Hz), 3.66 (m, 4H), 3.50 –3.48 (m, 2H), 2.50-2.46 (m, 4H), 2.09 (s, 3H).

4-[(4-Acetylpiperazin-1-yl)methyl]-2-amino-3-fluoropyridine (14-4)

To a solution of 4-[(4-acetylpiperazin-1-yl)methyl]-2-chloro-3-fluoropyridine (14-3, 85 mg, 0.31 mmole) in dry toluene (2 mL) was added NaOtBu (42 mg, 0.44 mmole), racemic BINAP (29 mg, 0.05 mmole), $Pd_2(dba)_3$ (14 mg, 0.02 mmole), and benzophenone imine (0.06 mL, 0.38 mmole) then the mixture was heated to 80 ° C. After 18 hr the mixture was cooled to RT. A solution of 1N HCl:THF (1:1, 10 mL) was added and the mixture stirred for 1 hr. The mixture was washed with EtOAc (2×). The aqueous layer was made basic with saturated $NaHCO_3$ then extracted with EtOAc (3×). The combined organic layers were dried ($Na_2SO_4$), filtered, and concentrated. Flash column chromatography (gradient, 0–5% MeOH/$CH_2Cl_2$) gave the titled compound as a light yellow solid: $^1$H-NMR (500 MHz, $CDCl_3$) δ7.81 (d, 1H, J=5.12 Hz), 6.71 (t, 1H, J=4.88 Hz), 4.56 (bs, 2H), 3.63 (t, 2H, J=5.13 Hz), 3.56 (s, 2H), 3.10 (t, 2H, J=5.13 Hz), 2.46 (m, 2H), 2.08 (s, 3H); MS (ES) (M+H)$^+$253.

2-({4-[(4-Acetylpiperazin-1-yl)methyl]-3-fluoropyridin-2-yl}amino)-1,3-thiazole-5-carbonitrile (14-5)

To a solution of 4-[(4-acetylpiperazin-1-yl)methyl]-2-amino-3-fluoropyridine (14-4, 39 mg, 0.155 mmole) and 2-chloro-5-cyano-1,3-thiazole (31 mg, 0.22 mmole) in dry THF (2 mL) was added NaH (14 mg, 60% dispersion in mineral oil, 0.37 mmole) at RT. After gas evolution had ceased the mixture was heated to reflux. After 3 hr additional 2-chloro-5-cyano-1,3-thiazole (10 mg) was added and heating continued. After 1.5 hr was cooled to RT, quenched with saturated $NH_4Cl$, and extracted with EtOAc (3×). The combined organic layers were dried ($MgSO_4$), filtered, and concentrated. Purification by reverse phase HPLC (5–100% $CH_3CN/H_2O$+0.1% TFA) gave the TFA salt of the titled compound as a yellow solid. $^1$H-NMR (500 MHz, $d^4$-MeOH) δ8.30 (d, 1H, J=5.13 Hz), 8.09 (s, 1H), 7.21 (t, 1H, J=4.88 Hz), 4.30 (s, 2H), 3.76 (bs, 4H), 3.18 (bs, 2H), 3.12 (bs, 2H), 2.13 (s, 3H); MS (ES) (M+H)$^+$361.

SCHEME 15

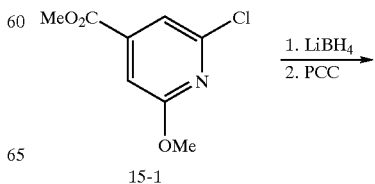

15-1

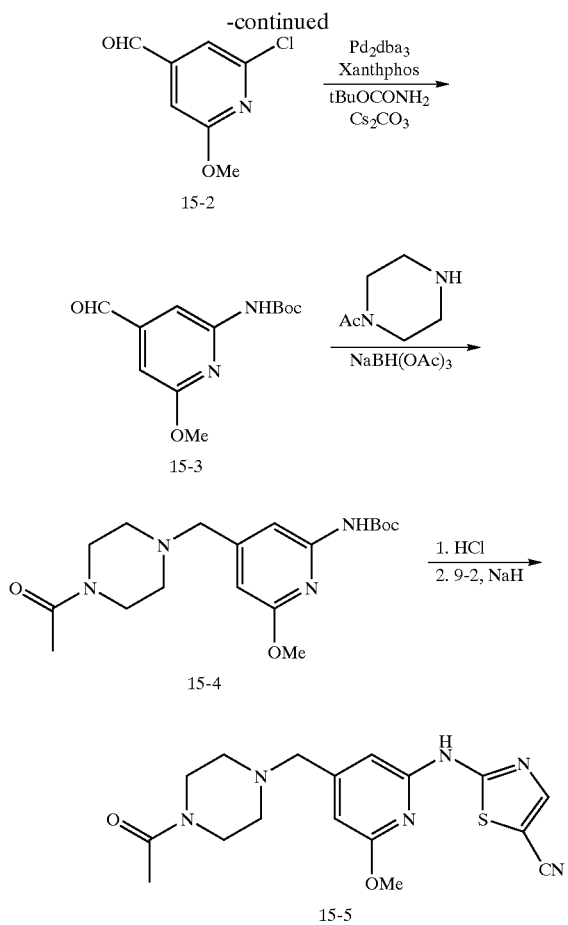

concentrated. Flash column chromatography (gradient, 0–10% EtOAc/hexanes) gave the titled compound as an orange solid. $^1$H-NMR (500 MHz, CDCl$_3$) δ9.98 (s, 1H), 7.91 (s, 1H), 6.82 (s, 1H), 3.88 (s, 3H), 1.54 (s, 9H); MS (ES) (M+H)$^+$253.

tert-Butyl 4-[(4-acetylpiperazin-1-yl)methyl]-6-methoxypyridin-2-ylcarbamate (15-4)

To a solution of tert-butyl 4-formyl-6-methoxypyridin-2-ylcarbamate (15-3, 292 mg, 1.16 mmole) and 1-acetylpiperazine (178 mg, 1.39 mmole) in 2% glacial HOAc in CH$_2$Cl$_2$ (5 mL) was added NaBH(OAc)$_3$ (270 mg, 1.27 mmole) at RT. After 1.5 hr the mixture was quenched with saturated NaHCO$_3$ and extracted with CH$_2$Cl$_2$ (3×). The combined organic layers were dried (MgSO$_4$), filtered, and concentrated. Flash column chromatography (gradient, 0–5% EtOH/EtOAc) gave the titled compound as a white foam. $^1$H-NMR (500 MHz, CDCl$_3$) δ7.41 (s, 1H), 7.00 (bs, 1H), 6.43 (s, 1H), 3.83 (s, 3H), 3.63 (bs, 2H), 3.46 (bs, 4H), 2.41 (m, 4H), 2.08 (s, 3H), 1.52 (s, 9H); MS (ES) (M+H)$^+$ 365.

2-({4-[(4-Acetylpiperazin-1-yl)methyl]-6-methoxypyridin-2-yl}amino)-1,3-thiazole-5-carbonitrile (15-5)

tert-Butyl 4-[(4-acetylpiperazin-1-yl)methyl]-6-methoxypyridin-2-ylcarbamate (15-4, 310 mg, 0.85 mmole) was taken up in 4 M HCl in dioxane (15 mL) at RT. After 4 hr the mixture was diluted with H$_2$O and neutralized with solid NaHCO$_3$. The resulting mixture was extracted with CH$_2$Cl$_2$ (3×). The combined organic layers were dried (MgSO$_4$), filtered, and concentrated. The residue was taken up in dry THF (5 mL). To this was added NaH (90 mg, 60% dispersion in mineral oil, 2.13 mmole). After gas evolution had ceased 2-chloro-5-cyano-1,3-thiazole (185 mg, 1.28 mmole) was added and the mixture heated to reflux. After 2.5 hr the mixture was cooled to RT and quenched with saturated NH$_4$Cl. The layers were separated and the aqueous layer extracted with CH$_2$Cl$_2$ (4×). The combined organic layers were dried (MgSO$_4$), filtered, and concentrated. Flash column chromatography (gradient, 0–15% EtOH/EtOAc) gave the titled compound as a tan solid. $^1$H-NMR (500 MHz, d$^6$-DMSO) δ8.26 (s, 1H), 6.70 (s, 1H), 6.43 (s, 1H), 4.04 (s, 3H), 3.47 (s, 2H), 3.43 (m, 4H), 2.38 (m, 2H), 2.31 (m, 2H), 1.98 (s, 3H); MS (ES) (M+H)$^+$373.

(2-Chloro-6-methoxypyridin-4-yl)methanol

To a solution of methyl (2-chloro-6-methoxypyridin-4-yl)carboxylate (15-1, 2.0 g, 9.92 mmole) in dry THF (40 mL) was added LiBH$_4$ (7.4 mL, 2 M in THF, 14.88 mmole) then the mixture was heated to reflux. After 18 hr the mixture was cooled to RT and quenched by slow addition of H$_2$O. The layers were separated and the aqueous layer extracted with EtOAc (2×). The combined organic layers were dried (MgSO$_4$), filtered, and concentrated to give the titled compound a white solid which was sufficiently pure for use in the next step. $^1$H-NMR (500 MHz, CDCl$_3$) δ6.90 (s, 1H), 6.65 (s, 1H), 4.67 (m, 2H), 3.94 (s, 3H).

2-Chloro-6-methoxyisonicotinaldehyde (15-2)

To a solution of (2-chloro-6-methoxypyridin-4-yl)methanol (1.73 g, 9.97 mmole) from the protocol immediately above in CH$_2$Cl$_2$ (40 ML) was added PCC (2.58 g, 11.96 mmole) all at once at RT. After 60 hr the mixture was diluted with Et$_2$O and filtered through a plug of Celite®. The filtrate was concentrated to give the titled compound as a tan-yellow solid which was sufficiently pure for use in the next step. $^1$H-NMR (500 MHz, CDCl$_3$) δ9.96 (s, 1H), 7.32 (s, 1H), 7.06 (s, 1H), 4.00 (s, 3H).

tert-Butyl 4-formyl-6-methoxypyridin-2-ylcarbamate (15-3)

To a solution of 2-chloro-6-methoxyisonicotinaldehyde (15-2, 500 mg, 2.91 mmole) in dry dioxane (5 mL) was added Cs$_2$CO$_3$ (1.42 g, 4.37 mmole), Xanthphos (253 mg, 0.44 mmole), Pd$_2$(dba)$_3$ (133 mg, 0.15 mmole), and tert-butylcarbamate (410 mg, 3.5 mmole) then the mixture was heated to reflux. After 18 hr the mixture was cooled to RT., diluted with H$_2$O, and extracted with EtOAc (3×). The combined organic layers were dried (MgSO$_4$), filtered, and

SCHEME 16

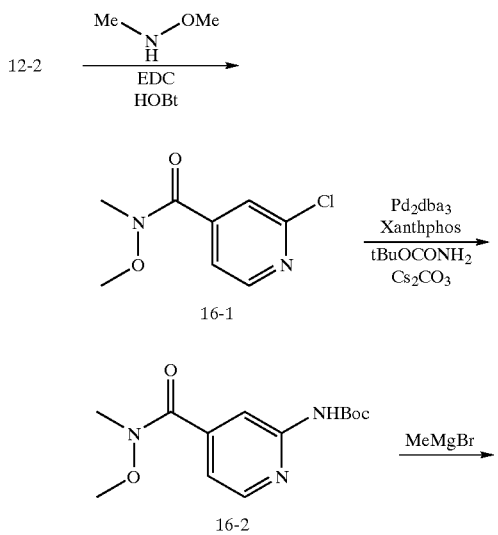

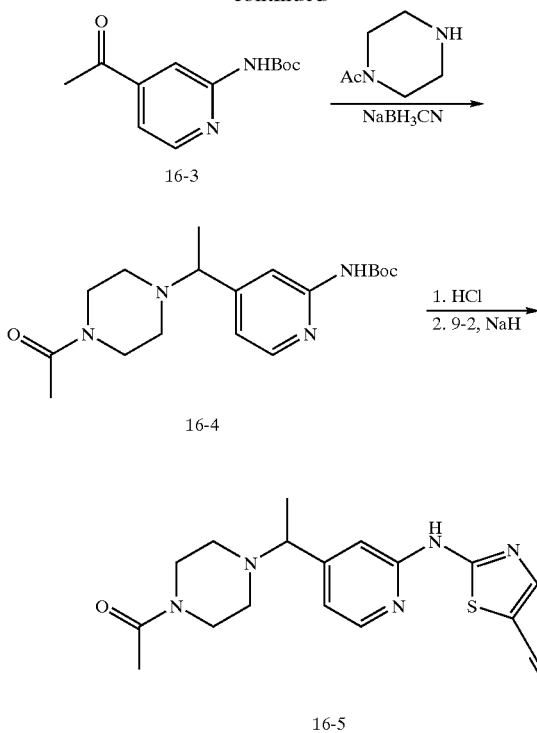

2-Chloro-N-methoxy-N-methylisonicotinamide (16-1)

2-Chloroisonicotinic acid (12-2, 2.0 g, 12.7 mmole), N,O-dimethylhydroxylamine hydrochloride (3.71 g, 38.1 mmole), EDC (2.92 g, 15.2 mmole), and HOBt (2.06 g, 15.2 mmole) were combined in dry DMF (40 mL). To this was added Et$_3$N (8.9 mL, 63.47 mmole) at RT. After 60 hr the mixture was diluted with H$_2$O and extracted with EtOAc (4×). The combined organic layers were washed with H$_2$O, brine; then dried (MgSO$_4$), filtered, and concentrated to give the titled compound as an amber oil which solidified on standing. The material was sufficiently pure for use in the next step. $^1$H-NMR (500 MHz, CDCl$_3$) δ8.47 (d, 1H, J=5.13 Hz), 7.57 (s, 1H), 7.45 (m, 1H), 3.56 (s, 3H), 3.38 (s, 3H).

tert-Butyl 4-{[methoxy(methyl)amino]carbonyl}pyridin-2-ylcarbamate (16-2)

To a solution of 2-chloro-N-methoxy-N-methylisonicotinamide (16-1, 500 mg, 2.49 mmole) in dry dioxane (5 ml) was added Cs$_2$CO$_3$ (1.22 g, 3.74 mmole), Xanthphos (216 mg, 0.37 mmole (Kranenburg, M. et. al. Organometallics 1995, 14, 3081–3089)), Pd$_2$(dba)$_3$ (114 mg, 0.12 mmole), and tert-butylcarbamate (350 mg, 2.99 mmole) then the mixture was heated to reflux. After 18 hr the mixture was cooled to RT., diluted with H$_2$O, and extracted with EtOAc (3×). The combined organic layers were dried (MgSO$_4$), filtered, and concentrated. Flash column chromatography (50% EtOAc/hexanes) gave the titled compound as a pale yellow solid. $^1$H-NMR (500 MHz, CDCl$_3$) δ8.31 (d, 1H, J=5.13 Hz), 8.16 (bs, 1H), 7.74 (s, 1H), 7.12 (d, 1H, J=5.13 Hz), 3.61 (s, 3H), 3.34 (s, 3H), 1.53 (s, 9H); MS (ES) (M+H)$^+$282.

tert-Butyl 4-acetylpyridin-2-ylcarbamate (16-3)

To a solution of tert-butyl 4{[methoxy(methyl)amino]carbonyl}pyridin-2-ylcarbamate (16-2, 224 mg, 0.8 mmole) in dry THF (5 mL) was added MeMgBr (0.6 mL, 3 M in Et$_2$O, 1.75 mmole) at −20° C. After 30 minutes the mixture was warmed to RT. After 30 minutes additional MeMgBr (0.3 mL) was added. After 1 hr the mixture was quenched with saturated NH$_4$Cl and extracted with EtOAc (3×). The combined organic layers were dried (MgSO$_4$), filtered, and concentrated to give the titled compound as an off-white solid which was sufficiently pure for use in the next step. $^1$H-NMR (500 MHz, (CDCl$_3$) δ8.44 (s, 1H), 8.40 (d, 1H, J=5.13 Hz), 8.02 (bs, 1H), 7.41 (d, 1H, J=5.13 Hz), 2.64 (s, 3H), 1.56 (s, 9H).

tert-Butyl 4-[1-(4-acetylpiperazin-1-yl)ethyl]pyridin-2-ylcarbamate (16-4)

To a suspension of tert-butyl 4-acetylpyridin-2-ylcarbamate (16-3, 187 mg, 0.79 mmole) in MeOH (3 mL) was added 1-acetylpiperazine (304 mg, 2.37 mmole), glacial HOAc (0.14 mL, 2.3.7 mmole), and NaBH$_3$CN (149 mg, 2.37 mmole) then the mixture was heated to 50° C. After 6 hr additional NaBH$_3$CN (149 mg, 2.37 mmole) was added and heating continued. After 18 hr the mixture was cooled to RT, diluted with saturated NaHCO$_3$, and extracted with CH$_2$Cl$_2$ (3×). The combined organic layers were dried (MgSO$_4$), filtered, and concentrated. Flash column chromatography (gradient, 0–10% EtOH/EtOAc) gave the titled compound as an oil: $^1$H-NMR (500 MHz, CDCl$_3$) δ8.17 (d, 1H, J=5.13 Hz), 7.87 (s, 1H), 7.52 (bs, 1H), 6.97 (d, 1H, J=5.13 Hz), 3.64–3.57 (m, 2H), 3.45–3.39 (m, 3H), 2.49–2.35 (m, 4H), 2.06 (s, 3H) 1.54 (s, 9H), 1.35 (d, 3H, J=6.59 Hz).

2-({4-[1-(4-Acetylpiperazin-1-yl)ethyl]pyridin-2-yl}amino)-1,3-thiazole-5-carbonitrile (16-5)

tert-Butyl 4-[1-(4-acetylpiperazin-1-yl)ethyl]pyridin-2-ylcarbamate (16-4, 137 mg, 0.39 mmole) was taken up in 4 M HCl in dioxane (10 mL) at RT. After 60 hr the mixture was diluted with H$_2$O and neutralized with solid NaHCO$_3$. The resulting mixture was extracted with CH$_2$Cl$_2$ (3×). The combined organic layers were dried (MgSO$_4$), filtered, and concentrated. The residue was taken up in dry THF (2 mL). To this was added NaH (40 mg, 60% dispersion in mineral oil, 0.98 mmole). After gas evolution had ceased 2-chloro-5-cyano-1,3-thiazole (85 mg, 0.59 mmole) was added and the mixture heated to reflux. After 3 hr the mixture was cooled to RT and quenched with saturated NH$_4$Cl. The layers were separated and the aqueous layer extracted with EtOAc (4×). The combined organic layers were dried (MgSO$_4$), filtered, and concentrated. Flash column chromatography (gradient, 0–15% EtOH/EtOAc) gave the titled compound as a tan solid. $^1$H-NMR (500 MHz, d$^6$-DMSO) δ12.18 (s, 1H), 8.34 (d, 1H, J=5.13 Hz), 8.26 (s, 1H), 7.12 (s, 1H), 7.05 (d, 1H, J=5.13 Hz), 3.52–3.41 (m, 5H), 2.44–2.03 (m, 4H), 1.96 (m, 3H), 1.28 (d, 3H, J=6.59 Hz); MS (ES) (M+H)$^+$357.

SCHEME 17

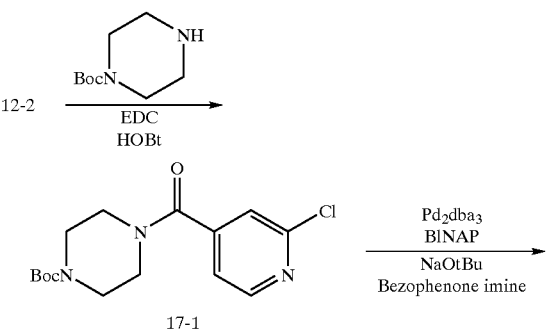

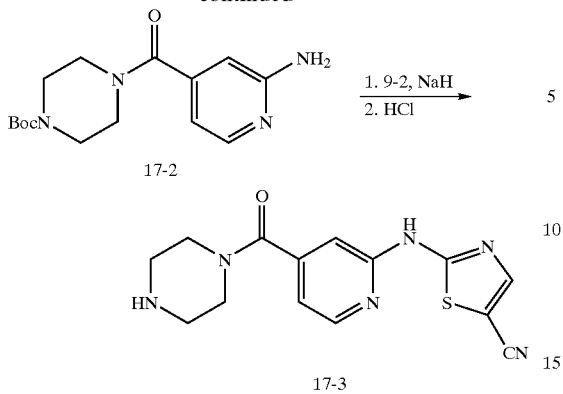

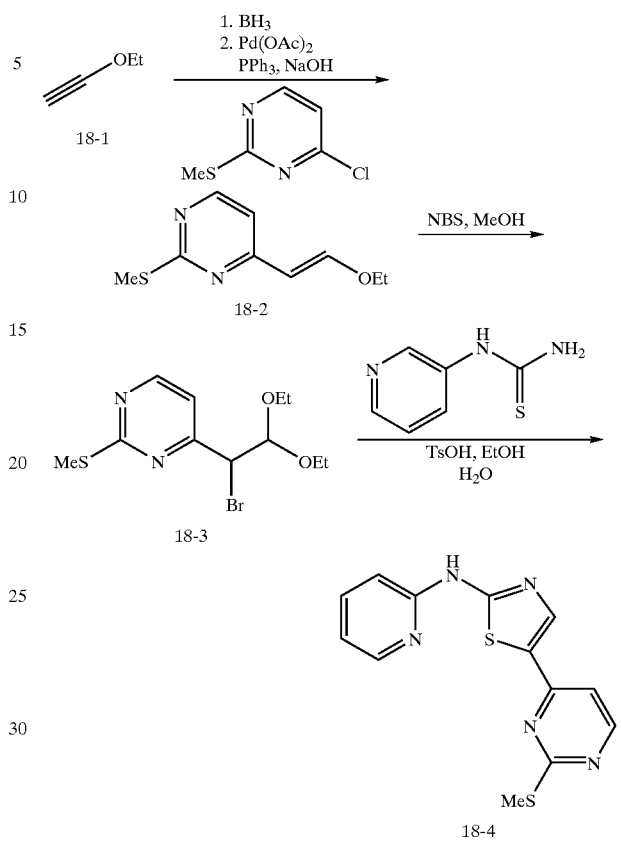

SCHEME 18 tert-Butyl 4-(2-chloroisonicotinoyl)piperazine-1-carboxylate (17-1)

2-Chloroisonicotinic acid (12-2, 250 mg, 1.59 mmole), tert-butylpiperazine-1-carboxylate (355 mg, 1.9 mmole), EDC (365 mg, 1.9 mmole), and HOBt (257 mg, 1.9 mmole) were combined in dry DMF (10 mL). To this was added $Et_3N$ (0.55 mL, 3.97 mmole) at RT. After 18 hr the mixture was diluted with $H_2O$ and extracted with EtOAc (4×). The combined organic layers were washed with $H_2O$, brine; then dried ($MgSO_4$), filtered, and concentrated to give the titled compound as an amber oil which was used immediately in the next step.

tert-Butyl 4-(2-aminoisonicotinoyl)piperazine-1-carboxylate (17-2)

To a solution of tert-butyl 4-(2-chloroisonicotinoyl) piperazine-1-carboxylate (17-1, 524 mg) in dry toluene (10 mL) was added NaOtBu (216 mg, 2.25 mmole), racemic BINAP (150 mg, 0.24 mmole), $Pd_2(dba)_3$ (74 mg, 0.08 mmole), and benzophenone imine (0.32 mL, 1.93 mmole) then the mixture was heated to 80° C. After 18 hr the mixture was cooled to RT. A solution of 1N HCl:THF (1:1) was added and stirring continued. After 4 hr the mixture was neutralized with saturated $NaHCO_3$ and extracted with EtOAc (3×). The combined organic layers were dried ($MgSO_4$), filtered, and concentrated. Flash column chromatography (gradient, 50–100% EtOAc/hexanes then 0–10%MeOH/$CH_2Cl_2$) gave the titled compound as a yellow solid. $^1$H-NMR (500 MHz, $CDCl_3$) δ8.12 (d, 1H, J=5.13 Hz), 6.58 (d, 1H, J=5.13 Hz), 6.47 (s, 1H), 4.55 (bs, 2H), 3.72–3.36 (m, 4H), 1.47 (s, 9H); MS (ES) (M+H)$^+$307.

2-{[4-(Piperazin-1-ylcarbonyl)pyridin-2-yl]amino}-1,3-thiazole-5-carbonitrile (17-3)

To a suspension of tert-butyl 4-(2-aminoisonicotinoyl) piperazine-1-carboxylate (17-2, 89 mg, 0.29 mmole) in dry THF (3 mL) was added NaH (30 mg, 60% dispersion in mineral oil, 0.73 mmole). After gas evolution had ceased 2-chloro-5-cyano-1,3-thiazole (63 mg, 0.44 mmole) was added and the mixture heated to reflux. After 18 hr the mixture was concentrated to dryness. The residue was taken up in 4 M HCl in dioxane (10 mL). After 4 h the mixture was neutralized with saturated $NaHCO_3$ and extracted with $CH_2Cl_2$ (3×). The combined organic layers were dried ($MgSO_4$), filtered, and concentrated. Purification by reverse phase HPLC (5–100% $CH_3CN/H_2O$+0.1% TFA) gave the TFA salt of titled compound as a white solid. $^1$H-NMR (500 MHz, d$^6$-DMSO) δ12.45 (s, 1H), 8.85 (bs, 2H), 8.47 (m, 1H), 8.16 (s, 1H), 7.18 (m, 2H), 3.82 (bs, 2H), 3.55 (bs, 2H), 3.24 (bs, 2H), 3.15 (bs, 2H); MS (ES) (M+H)$^+$315.

4-(2-Ethoxy-vinyl)-2-methylsulfanyl-pyrimidine (18-2)

Ethyl ethynyl ether (2.50 g, 35.7 mmol) was dissolved in 50 mL anhydrous THF under $N_2$. The solution was cooled to 0° C. and $BH_3$-THF (1.0 M in THF, 11.9 mL, 11.9 mmol) was added drop-wise. The reaction was allowed to warm to RT and after 2 h the tris-(2-ethoxy-vinyl)borane that was generated was used in the next step. A flame dried flask under $N_2$ was charged with 4-chloro-2-(methylthio) pyrimidine (0.200 g, 1.25 mmol), $Pd(OAc)_2$ (0.003 g, 0.01 mmol), $PPh_3$ (0.010 g, 0.040 mmol), NaOH (0.149 g, 3.73 mmol). Anhydrous THF, 2 mL, was added followed by the addition of 0.700 mL (0.50 mmol) of the solution of tris-(2-ethoxy-vinyl)borane generated above. The reaction was heated at reflux for 16 h, then was cooled to RT and quenched with sat $NaHCO_3$ (aq). The mixture was extracted 3× with EtOAc and the combined organic extracts were dried over $Na_2SO_4$, filtered and concentrated. The product was purified to moderate purity by flash column chromatography and used in the next step.

4-(1-Bromo-2,2-diethoxy-ethyl)-2-methylsulfanyl-pyrimidine (18-3)

4-(2-Ethoxy-vinyl)-2-methylsulfanyl-pyrimidine (18-2, 0.236 g, 1.20 mmol) was dissolved in 5 mL EtOH and the resulting solution was cooled to 0° C. NBS (0.214 g, 1.20 mmol) was added in small portions. After 2 h the reaction was concentrated in vacuo. Purification by flash column chromatography (eluting with 98:2 DCM/MeOH) provided the titled compound. $^1$H NMR ($CDCl_3$) δ8.50 (d, 1H, J=5.0 Hz), 7.09 (d, 1H, J=5.1 Hz), 5.05 (d, 1H, J=6.8 Hz), 4.81 (d, 1H, J=6.9 Hz), 3.77 (m, 2H), 3.53 (m, 2H), 2.57 (s, 3H), 1.26 (t, 3H, J=7.0 Hz), 1.08 t, 3H, J=7.1 Hz).

[5-(2-Methylsulfanyl-pyrimidin-4-yl)-thiazol-2-yl]-pyridin-2-yl-amine (18-4)

4-(1-Bromo-2,2-diethoxy-ethyl)-2-methylsulfanyl-pyrimidine (18-3, 0.050 g, 0.156 mmol) and 2-pyridylthiourea (0.024 g, 0.16 mmol) were stirred in 1 mL EtOH and 0.10 mL water. p-Toluenesulfonic acid monohydrate (5 mg, 0.03 mmol) was added and the reaction was heated to reflux. After 8 h an addional 30 mg (0.156 mmol) p-toluenesulfonic acid monohydrate and the reaction was refluxed an additional 16 h. The reaction was concentrated and purified by flash column chromatography (elute with a gradient: 3–6% MeOH in DCM). $^1$H NMR (DMSO-$d_6$) δ11.75 (s, 1H), 8.50 (d, 1H, J=5.4 Hz), 8.49 (m, 2H), 7.77 (t, 1H, J=6.7 Hz), 7.60 d, 1H, J=5.5 Hz), 7.13 (d, 1H, 8.2 Hz), 7.02 (t, 1H, J=6.6 Hz), 2.55 (s, 3H).

SCHEME 19

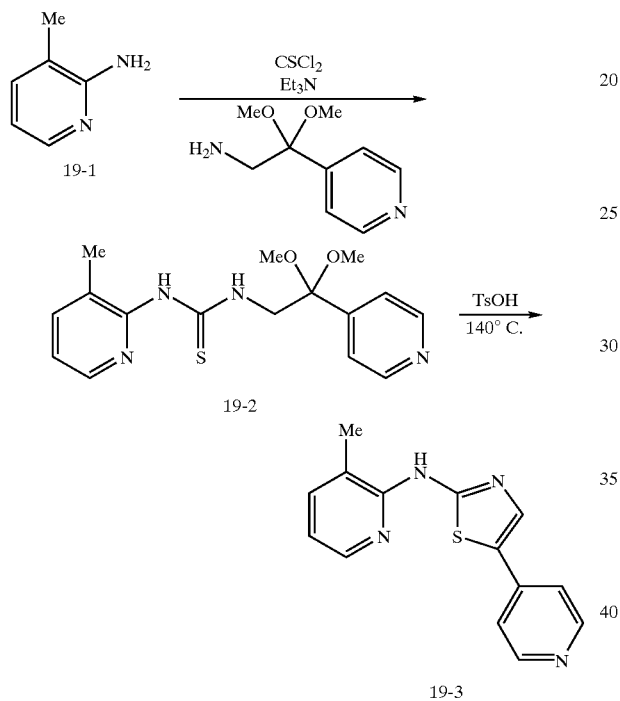

1-(2,2-Dimethoxy-2-pyridin-4-yl-ethyl)-3-(3-methyl-pyridin-2-yl)-thiourea (19-2)

2-Amino-3-methylpyridine (19-1, 0.281 g, 2.60 mmol) was stirred in 6 mL anhydrous DCM under $N_2$. Thiophosgene (0.198 mL, 2.60 mmol) was added followed by the addition of triethylamine (1.09 mL, 7.79 mmol) and an additional 4 mL anhydrous DCM. After 30 min 2,2-dimethoxy-2-pyridin-4-yl-ethylamine (0.430 g, 2.36 mmol, Ganellin, C. R.; Hosseini, S. K.; Khalaf, Y. S.; Tertiuk, W.; Arrang, J.-M.; et al. J.Med.Chem. 1995, 38, 3342–3350) was added as a solution in 2 mL anhydrous DCM. After 16 h the reaction was quenched with sat NaHCO3 (aq) and extracted 3× with DCM. The combined organic extracts were dried over $Na_2SO_4$, filtered, and concentrated to provide the pure titled compound as a tan solid. $^1$H NMR (CDCl$_3$) δ11.88 (s, 1H), 8.65 (d, 2H, J=6.0 Hz), 7.76 (m, 2H), 7.50 (d, 2H, J=6.2 Hz), 7.44 (m, 1H), 6.87 (dd, 1H, J=5.1, 7.3 Hz), 4.22 (d, 2H, J=5.0 Hz), 3.29 (s, 6H), 2.22 (s, 3H).

(3-Methyl-pyridin-2-yl)-(5-pyridin4-yl-thiazol-2-yl)-amine (19-3)

1-(2,2-Dimethoxy-2-pyridin-4-yl-ethyl)-3-(3-methyl-pyridin-2-yl)-thiourea (19-2, 0.050 g, 0. 16 mmol) and p-toluenesulfonic acid monohydrate (0.003 g, 0.02 mmol) were combined and heated to 140° C. The reaction was terminated at partial conversion and was purified by reverse phase HPLC to provide the titled compound. $^1$H NMR (CD$_3$OD) δ8.61 (d, 2H, J=7.1 Hz), 8.48 (s, 1H), 8.30 (dd, 1H, J=1.0, 4.8 Hz), 8.15 (d, 2H, J=7.3 Hz), 7.74 (dd, 1H, J=0.7, 7.3 Hz), 7.10 (dd, 1H, J=5.1, 7.3 Hz), 2.43 (s, 3H).

What is claimed is:
1. A compound of Formula I

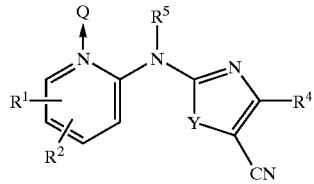

or a pharmaceutically acceptable salt or stereoisomer thereof, wherein

Y is S;

Q is O or absent;

$R^1$ is:
1) $O_r(C_1-C_6)$perfluoroalkyl,
2) OH,
3) CN,
4) halogen,
5) $(C=O)_rO_s(C_1-C_{10})$alkyl,
6) $(C=O)_rO_s(C_2-C_8)$cycloalkyl,
7) $(C=O)_rO_s(C_2-C_{10})$alkenyl,
8) $(C=O)_rO_s(C_2-C_{10})$alkynyl,
9) $(C=O)_rO_s$aryl,
10) $(C=O)_rO_s$heterocyclyl, or
11) $NR^aR^b$,
wherein r and s are independently 0 or 1, and said alkyl, cycloalkyl, alkenyl, alkynyl, aryl, and heterocyclyl is optionally substituted with one or more substituents selected from $R^7$;

$R^2$ is $R^1$ or H;

$R^4$ is H or $(C_1-C_6)$alkyl;

$R^5$ is:
1) H,
2) $SO_2R^c$,
3) $(C=O)_rR^c$, wherein r is 0 or 1, or
4) $CO_2R^c$;

$R^7$ is:
1) $O_r(C=O)_sNR^aR^b$,
2) $(C=O)_rO_s$aryl,
3) $(C=O)_rO_s$-heterocyclyl,
4) halogen,
5) OH,
6) oxo,
7) $O(C_1-C_3)$perfluoroalkyl,
8) $(C_1-C_3)$perfluoroalkyl,
9) $(C=O)_rO_s(C_1-C_{10})$alkyl,
10) CHO,
11) $C_2H$,
12) CN, or
13) $(C_3-C_8)$cycloalkyl,
wherein r and s are independently 0 or 1, and said aryl, heterocyclyl and cycloalkyl are optionally substituted with one or more substituents selected from $R^d$;

$R^a$ and $R^b$ are independently:
1) H,

2) $(C=O)_r(C_1-C_{10})$alkyl,
3) $(C=O)_r(C_3-C_6)$cycloalkyl,
4) $S(O)_2R^c$,
5) $(C=O)_r$heterocyclyl,
6) $(C=O)_r$aryl, or
7) $CO_2R^c$,
   wherein r is 0 or 1 and said alkyl, cycloalkyl, heterocyclyl, and aryl optionally substituted with one or more substituents selected from $R^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^d$;

$R^c$ is $(C_1-C_6)$alkyl, $(C_3-C_6)$cycloalkyl, aryl, or heterocyclyl;

$R^d$ is selected from:
   1) $(C=O)_rO_s(C_1-C_{10})$alkyl, wherein r and s are independently 0 or 1, optionally substituted with up to three substituents selected from OH, $(C_1-C_6)$alkoxy, halogen, CN, oxo, $N(R^e)_2$ and $S(O)_2R^c$,
   2) $O_r(C_1-C_3)$perfluoroalkyl,
   3) $(C_0-C_6)$alkylene-$S(O)_mR^c$, wherein m is 0, 1, or 2,
   4) oxo,
   5) OH,
   6) halo,
   7) CN,
   8) $(C_3-C_6)$cycloalkyl, optionally substituted with up to three substituents selected from OH, $(C_1-C_6)$alkoxy, halogen, CN, oxo, $N(R^e)_2$, and $S(O)_2R^c$,
   9) $(C_0-C_6)$alkylene-aryl), optionally substituted with up to three substituents selected from $R^e$,
   10) $(C_0-C_6)$alkylene-heterocyclyl, optionally substituted with up to three substituents selected from $R^e$,
   11) $(C_0-C_6)$alkylene-$N(R^e)_2$,
   12) $C(O)R^c$,
   13) $CO_2R^c$,
   14) $C(O)H$, and
   15) $CO_2H$; and $R^e$ is H, $(C_1-C_6)$alkyl, aryl, heterocyclyl, $(C_3-C_6)$cycloalkyl or $S(O)_2R^c$;

and as used herein, the term "heterocycle" or "heterocyclyl" is a 5- to 10-membered aromatic or nonaromatic, monocyclic or bicyclic, heterocycle, containing from 1 to 4 heteroatoms selected from the group consisting of O, N and S.

2. The compound of claim 1, wherein Y is S and Q is absent.

3. The compound of claim 2, wherein
$R^1$ is:
   1) $O_r(C_1-C_6)$perfluoroalkyl,
   2) OH,
   3) CN,
   4) halogen,
   5) $(C=O)_rO_s(C_1-C_6)$alkyl,
   6) $(C=O)_rO_s(C_2-C_6)$cycloalkyl,
   7) $(C=O)_rO_s(C_2-C_6)$alkenyl,
   8) $(C=O)_rO_s(C_2-C_6)$alkynyl,
   9) $(C=O)_rO_s$aryl,
   10) $(C=O)_rO_s$heterocyclyl, or
   11) $NR^aR^b$,
       wherein r and s are independently 0 or 1, and said alkyl, cycloalkyl, alkenyl, alkynyl, aryl, and heterocyclyl is optionally substituted, with one, two or three substituents selected from $R^7$;

$R^7$ is:
   1) $O_r(C=O)_sNR^aR^b$,
   2) $(C=O)_rO_s$aryl,
   3) $(C=O)_rO_s$-heterocyclyl,
   4) halogen,
   5) OH,
   6) oxo,
   7) $O(C_1-C_3)$perfluoroalkyl,
   8) $(C_1-C_3)$perfluoroalkyl,
   9) $(C=O)_rO_s(C_1C_6)$alkyl,
   10) CHO,
   11) $C_2H$,
   12) CN, or
   13) $(C_3-C_6)$cycloalkyl,
       wherein r and s are independently 0 or 1, and said aryl, heterocyclyl and cycloalkyl are optionally substituted with one, two or three substituents selected from $R^d$;

$R^a$ and $R^b$ are independently:
   1) H,
   2) $(C=O)_r(C_1-C_6)$alkyl,
   3) $(C=O)_r(C_3-C_6)$cycloalkyl,
   4) $S(O)_2R^c$,
   5) $(C=O)_r$heterocyclyl,
   6) $(C=O)_r$aryl, or
   7) $CO_2R^c$,
       wherein r is 0 or 1 and said alkyl, cycloalkyl, heterocyclyl, and aryl optionally substituted with one, two or three substituents selected from $R^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one, two or three substituents selected from $R^d$;

$R^c$ is $(C_1-C_6)$alkyl, $(C_3-C_6)$cycloalkyl, or aryl; and
$R^d$ is selected from:
   1) $(C=O)_rO_s(C_1-C_6)$alkyl, wherein r and s are independently 0 or 1, optionally substituted with up to three substituents selected from OH, $(C_1-C_6)$alkoxy, halogen, CN, oxo, $N(R^e)_2$ and $S(O)_2R^c$,
   2) $O_r(C_1-C_3)$perfluoroalkyl,
   3) $(C_0-C_6)$alkylene-$S(O)_mR^c$, wherein m is 0, 1, or 2,
   4) oxo,
   5) OH,
   6) halo,
   7) CN,
   8) $(C_3-C_6)$cycloalkyl, optionally substituted with up to three substituents selected from OH, $(C_1-C_6)$alkoxy, halogen, CN, oxo, $N(R^e)_2$, and $S(O)_2R^c$,
   9) $(C_0-C_6)$alkylene-aryl, optionally substituted with up to three substituents selected from $R^e$,
   10) $(C_0-C_6)$alkylene-heterocyclyl, optionally substituted with up to three substituents selected from $R^e$,
   11) $(C_0-C_6)$alkylene-$N(R^e)_2$, 12) C(O)R$^c$,
13) CO$_2$R$^c$,
14) C(O)H, and
15) CO$_2$H.

4. The compound of claim 2, wherein

R$^1$ is (C$_1$–C$_{10}$)alkylene-NR$^a$R$^b$, optionally substituted with one or two substituents selected from R$^7$;

R$^2$ is H, CN, halogen, (C$_1$–C$_6$)alkyl, or (C$_1$–C$_6$)alkyloxy;

R$^5$ is H, (C$_1$–C$_6$)alkyl, CO$_2$(C$_1$–C$_6$)alkyl, or,CO(C$_1$–C$_6$)alkyl;

R$^7$ is:
1) O$_r$(C=O)$_s$NR$^a$R$^b$,
2) (C=O)$_r$O$_s$aryl,
3) (C=O)$_r$O$_s$-heterocyclyl,
4) halogen,
5) OH,
6) oxo,
7) O(C$_1$–C$_3$)perfluoroalkyl,
8) (C$_1$–C$_3$)perfluoroalkyl,
9) (C=O)$_r$O$_s$(C$_1$–C$_6$)alkyl,
10) CHO,
11) CO$_2$H,
12) CN, or
13) (C$_3$–C$_6$)cycloalkyl,
    wherein r and s are independently 0 or 1, and said aryl, heterocyclyl and cycloalkyl are optionally substituted with one or two substituents selected from R$^d$;

R$^a$ and R$^b$ are independently selected from:
1) H,
2) (C=O)$_r$(C$_1$–C$_6$)alkyl,
3) (C=O)$_r$(C$_3$–C$_6$)cycloalkyl,
4) S(O)$_2$R$^c$,
5) (C=O)$_r$heterocyclyl,
6) (C=O)$_r$aryl, and
7) CO$_2$R$^c$,
    wherein r is 0 or 1 and said alkyl, cycloalkyl, heterocyclyl, and aryl optionally substituted with one to three substituents selected from R$^d$, or R$^a$ and R$^b$ are taken together with the nitrogen to which they are attached to form a monocyclic or bicyclic heterocycle with 5–7 members in each ring and optionally containing, in addition to the nitrogen, one additional heteroatom selected from N, O and S, said monocyclic or bicyclic heterocycle optionally substituted with one or two substituents selected from R$^d$;

R$^c$ is (C$_1$–C$_6$)alkyl, (C$_3$–C$_6$)cycloalkyl, or aryl; and

R$^d$ is selected from:
1) (C=O)$_r$O$_s$(C$_1$–C$_6$)alkyl, wherein r and s are independently 0 or 1,optionally substituted with up to three substituents selected from OH, (C$_1$–C$_6$)alkoxy, halogen, CN, oxo, N(R$^e$)$_2$ and S(O)$_2$R$^c$,
2) O$_r$(C$_1$–C$_3$)perfluoroalkyl,
3) (C$_0$–C$_6$)alkylene-S(O)$_m$R$^c$, wherein m is 0, 1, or 2,
4) oxo,
5) OH,
6) halo,
7) CN,
8) (C$_3$–C$_6$)cycloalkyl, optionally substituted with up to three substituents selected from OH, (C$_1$–C$_6$)alkoxy, halogen, CN, oxo, N(R$^e$)$_2$, and S(O)$_2$R$^c$,
9) (C$_0$–C$_6$)alkylene-aryl, optionally substituted with one or two substituents selected. from R$^e$,
10) (C$_0$–C$_6$)alkylene-heterocyclyl, optionally substituted with one or two substituents selected from R$^e$,
11) (C$_0$–C$_6$)alkylene-N(R$^e$)$_2$,
12) C(O)R$^c$,
13) C$_2$R$^c$,
14) C(O)H, and
15) CO$_2$H.

5. A compound selected from:

2-[4-(4-methyl-5-oxo-[1,4]diazepan-1-ylmethyl)-pyridin-2-ylamino]-thiazole-5-carbonitrile;

2-[4-(4-acetyl-piperazin-1-ylmethyl)-pyridin-2-ylamino]-thiazole-5-carbonitrile;

2-[4-(4-methanesulfonyl-piperazin-1-ylmethyl)-pyridin-2-ylamino]-thiazole-5-carbonitrile;

2-[4-(1,1-dioxo-thiomorpholin-4-ylmethyl)-pyridin-2-ylamino]-thiazole-5-carbonitrile;

2-{4-[4-(2-hydroxy-ethanoyl)-piperazin-1-ylmethyl]-pyridin-2-ylamino}-thiazole-5-carbonitrile;

N-{1-[2-(5-cyano-thiazol-2-ylamino)-pyridin-4-ylmethyl]-pyrrolidin-3-yl}-methanesulfonamide;

4-({2-[(5-cyano-1,3-thiazol-2-yl)amino]-4-pyridinyl}-methyl)-N,N-dimethyl-1-piperazinecarboxamide;

2-[(4-{[(5-oxo-3-pyrrolidinyl)amino]methyl}-2-pyridinyl)amino]-1,3-thiazole-5-carbonitrile;

4-({2-[(5-cyano-1,3-thiazol-2-yl)amino]-4-pyridinyl}-methyl)-1-piperazinecarboxamide;

2-[(4-{[3-(methylsulfonyl)-1-pyrrolidinyl]methyl}-2-pyridinyl)amino]-1,3-thiazole-5-carbonitrile;

2-[4-(4-methyl-3-oxo-piperazin-1-ylmethyl)-pyridin-2-ylamino]-thiazole-5-carbonitrile;

2-(4-morpholin-4-ylmethyl-pyridin-2-ylamino)-thiazole-5-carbonitrile;

2-(4-{[(piperidin-4-ylmethyl)-amino]-methyl}-pyridin-2-ylamino)-thiazole-5-carbonitrile; and 2-(4-piperazin-1-ylmethyl-pyridin-2-ylamino)-thiazole-5-carbonitrile, or a pharmaceutically acceptable salt or N-oxide thereof.

6. A pharmaceutical composition which is comprised of a compound in accordance with claim 1 and a pharmaceutically acceptable carrier.

7. A pharmaceutical composition made by combining the compound of claim 1 and a pharmaceutically acceptable carrier.

8. A process for making a pharmaceutical composition which comprises combining a compound of claim 1 with a pharmaceutically acceptable carrier.

\* \* \* \* \*

UNITED STATES PATENT AND TRADEMARK OFFICE
CERTIFICATE OF CORRECTION

PATENT NO. : 6,586,423 B2
DATED : July 1, 2003
INVENTOR(S) : Mark T. Bilodeau et al.

It is certified that error appears in the above-identified patent and that said Letters Patent is hereby corrected as shown below:

Column 108,
Line 59, delete "11) $C_2H$," and insert therefore -- 11) $CO_2H$ --

Column 110,
Line 17, delete "11) $C_2H$," and insert therefore -- 11) $CO_2H$ --

Signed and Sealed this

Tenth Day of August, 2004

JON W. DUDAS
*Acting Director of the United States Patent and Trademark Office*